(12) United States Patent
Beck

(10) Patent No.: US 10,004,564 B1
(45) Date of Patent: Jun. 26, 2018

(54) ACCURATE RADIOGRAPHIC CALIBRATION USING MULTIPLE IMAGES

(71) Applicant: Paul Beck, Atlanta, GA (US)

(72) Inventor: Paul Beck, Atlanta, GA (US)

( * ) Notice: Subject to any disclaimer, the term of this patent is extended or adjusted under 35 U.S.C. 154(b) by 280 days.

(21) Appl. No.: 14/989,437

(22) Filed: Jan. 6, 2016

(51) Int. Cl.
*A61B 6/00* (2006.01)
*A61B 34/10* (2016.01)
*A61B 90/00* (2016.01)

(52) U.S. Cl.
CPC ............ *A61B 34/10* (2016.02); *A61B 6/4452* (2013.01); *A61B 6/505* (2013.01); *A61B 6/547* (2013.01); *A61B 6/585* (2013.01); *A61B 2034/107* (2016.02); *A61B 2034/108* (2016.02); *A61B 2090/3966* (2016.02)

(58) Field of Classification Search
CPC ....... A61B 6/4452; A61B 6/505; A61B 6/547; A61B 6/585
See application file for complete search history.

(56) References Cited

U.S. PATENT DOCUMENTS

| | | | |
|---|---|---|---|
| 5,360,446 | A | 11/1994 | Kennedy |
| 5,400,513 | A | 3/1995 | Duffield |
| 5,682,886 | A | 11/1997 | Delp et al. |
| 5,769,092 | A | 6/1998 | Williamson, Jr. |
| 5,799,055 | A | 8/1998 | Peshkin et al. |
| 5,832,422 | A | 11/1998 | Wiedenhoefer |
| 6,205,411 | B1 | 3/2001 | DiGioia et al. |
| 6,229,869 | B1 * | 5/2001 | Hu .................. A61B 6/4447 378/15 |
| 6,272,247 | B1 | 8/2001 | Manickam et al. |
| 6,334,157 | B1 | 12/2001 | Oppermann et al. |
| 6,342,905 | B1 | 1/2002 | Diedrich et al. |
| 6,424,332 | B1 | 7/2002 | Powell |

(Continued)

FOREIGN PATENT DOCUMENTS

EP 2405336 11/2012

OTHER PUBLICATIONS

Anonymous, "Iconico Screen Calipers," Jan. 2, 2010, 16 pages, retrieved from the internet: URL: http://web.archiv.org/web/20100102043404/http://iconico.com/caliper/index.aspx[retrieved on Oct. 20, 2011].

(Continued)

*Primary Examiner* — Dani Fox
(74) *Attorney, Agent, or Firm* — McDonnell Boehnen Hulbert & Berghoff LLP

(57) ABSTRACT

A radiographic system may be configured to capture a first radiograph containing a first image of an object with the source and the receiver in a first orientation with respect to one another. The system may store the first radiograph and metadata representing vertical and horizontal positions of the first orientation. At least one of the source and the receiver may be moved so that the source and the receiver are in a second orientation with respect to one another. A second radiograph containing a second image of the object may be captured with the source and the receiver in the second orientation. The second radiograph may be stored in memory along with metadata representing vertical and horizontal positions of the second orientation. Based on the captured radiographs, a magnification of the object of interest, as represented by the first image or the second image, may be determined.

19 Claims, 28 Drawing Sheets

(56) References Cited

U.S. PATENT DOCUMENTS

| | | | |
|---|---|---|---|
| 6,459,948 | B1 | 10/2002 | Ateshian et al. |
| 6,573,915 | B1 | 6/2003 | Sivan et al. |
| 6,701,174 | B1 | 3/2004 | Krause et al. |
| 6,772,026 | B2 | 8/2004 | Bradbury et al. |
| 6,932,842 | B1 | 8/2005 | Litschko et al. |
| 7,158,692 | B2 | 1/2007 | Chalana et al. |
| 7,383,073 | B1 | 6/2008 | Abovitz et al. |
| 7,388,972 | B2 | 6/2008 | Kitson |
| 7,468,075 | B2 | 12/2008 | Lang et al. |
| 7,534,263 | B2 | 5/2009 | Burdulis, Jr. et al. |
| 7,981,158 | B2 | 7/2011 | Fitz et al. |
| 7,983,777 | B2 | 7/2011 | Melton et al. |
| 8,066,708 | B2 | 11/2011 | Lang et al. |
| 8,077,950 | B2 | 12/2011 | Tsougarakis et al. |
| 8,908,937 | B2 | 12/2014 | Beck |
| 8,917,290 | B2 | 12/2014 | Beck |
| 2002/0080913 | A1* | 6/2002 | Roder ............... G01N 23/04 378/22 |
| 2004/0151399 | A1 | 8/2004 | Skurdal et al. |
| 2005/0038338 | A1 | 2/2005 | Bono et al. |
| 2005/0059873 | A1 | 3/2005 | Glozman et al. |
| 2005/0162419 | A1 | 7/2005 | Kim et al. |
| 2006/0242159 | A1 | 10/2006 | Bishop et al. |
| 2006/0287733 | A1 | 12/2006 | Bonutti |
| 2007/0118055 | A1 | 5/2007 | McCombs |
| 2007/0118243 | A1 | 5/2007 | Schroeder et al. |
| 2007/0198022 | A1 | 8/2007 | Lang et al. |
| 2007/0226986 | A1 | 10/2007 | Park et al. |
| 2007/0272747 | A1 | 11/2007 | Woods et al. |
| 2008/0063302 | A1 | 3/2008 | Russak et al. |
| 2008/0063304 | A1 | 3/2008 | Russak et al. |
| 2008/0148167 | A1 | 6/2008 | Russak et al. |
| 2008/0180406 | A1 | 7/2008 | Han et al. |
| 2008/0189358 | A1 | 8/2008 | Charles |
| 2008/0319448 | A1 | 12/2008 | Lavallee et al. |
| 2009/0043556 | A1 | 2/2009 | Axelson et al. |
| 2009/0089081 | A1 | 4/2009 | Haddad |
| 2009/0222014 | A1 | 9/2009 | Bojarski et al. |
| 2009/0259967 | A1 | 10/2009 | Davidson et al. |
| 2009/0306676 | A1 | 12/2009 | Lang et al. |
| 2009/0312805 | A1 | 12/2009 | Lang et al. |
| 2010/0030231 | A1 | 2/2010 | Revie et al. |
| 2010/0080491 | A1 | 4/2010 | Ohnishi |
| 2010/0134425 | A1 | 6/2010 | Storrusten |
| 2010/0135467 | A1 | 6/2010 | King et al. |
| 2010/0217270 | A1 | 8/2010 | Polinski et al. |
| 2010/0274534 | A1 | 10/2010 | Steines et al. |
| 2010/0281678 | A1 | 11/2010 | Burdulis, Jr. et al. |
| 2010/0295803 | A1 | 11/2010 | Kim et al. |
| 2010/0303313 | A1 | 12/2010 | Lang et al. |
| 2010/0303317 | A1 | 12/2010 | Tsougarakis et al. |
| 2010/0303324 | A1 | 12/2010 | Lang et al. |
| 2010/0305907 | A1 | 12/2010 | Fitz et al. |
| 2010/0329530 | A1 | 12/2010 | Lang et al. |
| 2011/0029091 | A1 | 2/2011 | Bojarski et al. |
| 2012/0008848 | A1 | 1/2012 | Beck |
| 2012/0194505 | A1* | 8/2012 | Beck ............... G09G 5/363 345/419 |
| 2015/0216498 | A1* | 8/2015 | Schulze ............... A61B 6/4085 378/19 |

OTHER PUBLICATIONS

Brannigan et al., "A Framework for "Need to Know" Authorizations in Medical Computer Systems: Responding to the Constitutional Requirements," JAMIA, Proceedings of the 18th Annual Symposium on Computer Applications in Medical Care, 1994, pp. 396-396.

King, Richard et al., "A novel method of accurately calculating the radiographic magnification of the hip," Warwick Orthopaedics, 2009.

Kosashvili et al., "Digital versus conventional templating techniques in preoperative planning for total hip arthoplasty," Can J Surgery, 2009, pp. 6-11, vol. 52, No. 1.

Michalikova et al., "The Digital Pre-Operative Planning of Total Hip Arthroplasty," Acta Polytechnica Hungarica, 2010, vol. 7, No. 3.

Moscovich et al., "Multi-finger cursor techniques," Proc. GI'06, Toronto: CIPS, 2006, pp. 1-7.

Murzic et al., "Digital Templating in Total Hip Replacement," US Musculoskeletal Review, 2006.

OrthoView, "Joint Arthroplasty Digital Orthopaedic Templating & Planning," 7 pages accessed Jan. 7, 2016, http://www.orthoview.com/product/joint-replacement.

OrthoView, "OrthoView Digital Pre-operative Planning Tools & Wizards," 5 pages accessed Jan. 7, 2016, http://www.orthoview.com/about/planning-software/scaling.

OrthoView, "Scaling Orthopaedic Digital X-rays in OrthoView Templating Software," 7 pages, accessed Jan. 7, 2016, http://www.orthoview.com/about/planning-software/scaling.

OrthoView, Orthopaedic Digital Templates for Pre-operative Planning, http://www.orthoview.com/about/planning-software/orthopaedic-templates, 2016.

Project SIKULI, http://www.sikuli.org/, accessed on Jan. 7, 2016, 2 pages.

Screen Capture Software for Windows, Mac and Chrome—Snagit, 7 pages, accessed Jan. 7, 2016, https://www.techsmith.com/snagit.html.

Steinberg et al., "Preoperative planning of total hip replacement using the TraumaCad system," Archives of Orthopaedic and Trauma Surgery: Including Arthroscorpy and Sports Medicine, Jan. 13, 2010, pp. 1429-1432, vol. 130, No. 12.

"TraumaCad User's Guide Version 2.2," Voyant Health, A Voyant Helath Ltd. Documents, 2010, 206 pages.

TraumaCad Touch New! and Trauma Cad OrthoWeb, Voyant Health, Dec. 2009, 2 pages, MK200197_B.

TraumaCad Touch Guide, BrainLAB's Digital Lightbox, Orthocrat, www.orthocrat.com, 12 pages.

Wikipedia, "Screenshot," May 22, 2009.

Wikipedia, "Distributed Computing," Jan. 5, 2009.

Wikipedia, "Metadata," May 29, 2009.

Wikipedia, "HUD (video gaming)," Dec. 6, 2009.

Wikipedia, "Photogrammerty," Jul. 7, 2010.

Yusof et al., "Devolpement of Total Knee Replacement Digital Tempmlating Software," Visual Infomatics: Bridging Research and Practice, Springer Berlin Heidelberg, Berlin, Heidelberg, Nov. 11, 2009, pp. 180-190.

European Patent Office, European Search Report dated Nov. 10, 2011, issued in connection with EP Application No. 11172626.

International Searching Authority, International Search Report and Written Opinion dated Mar. 31, 2017, issued in connection with International Application No. PCT/US2017/012012, filed on Jan. 3, 2017, 12 pages.

* cited by examiner

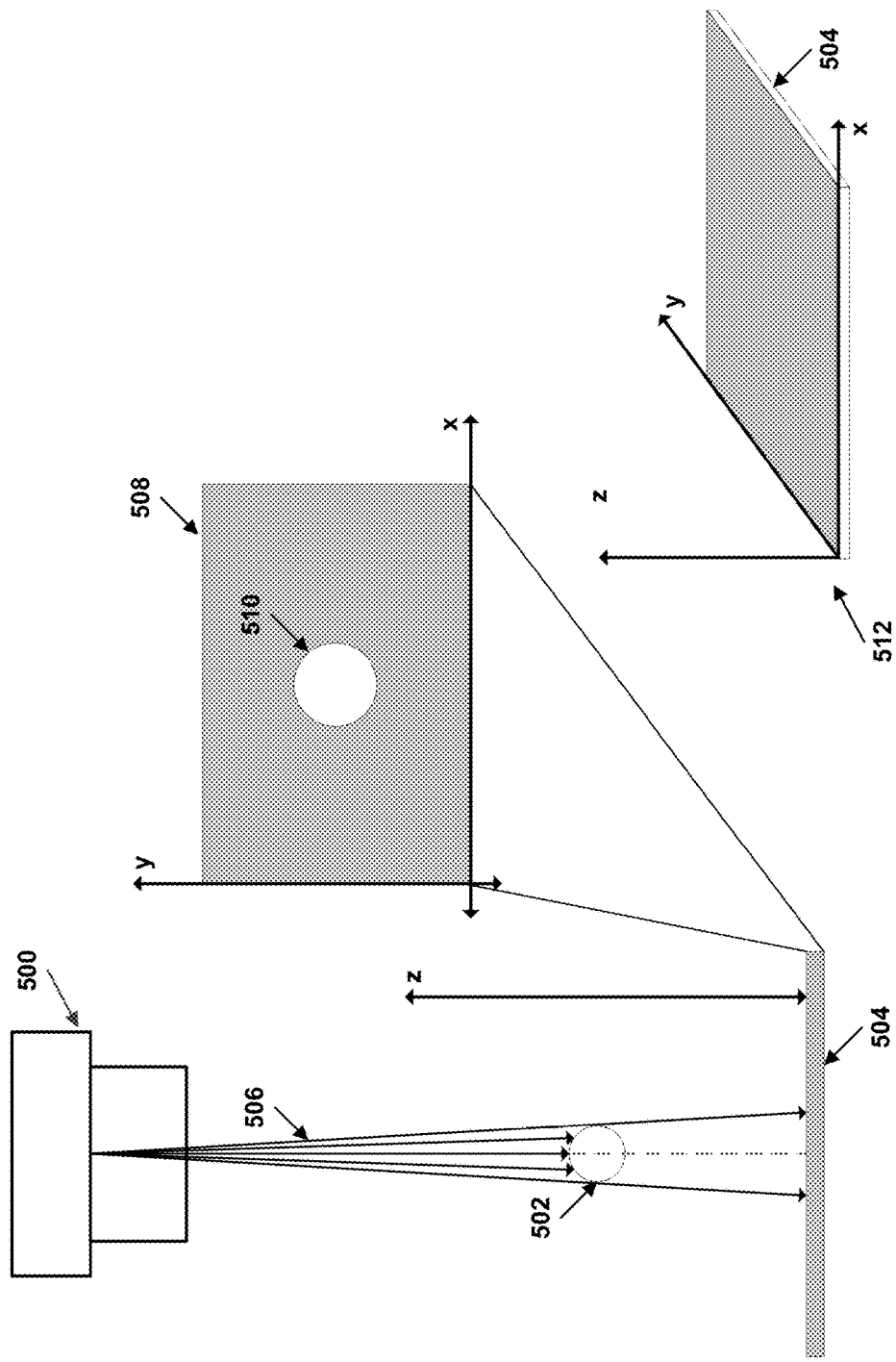

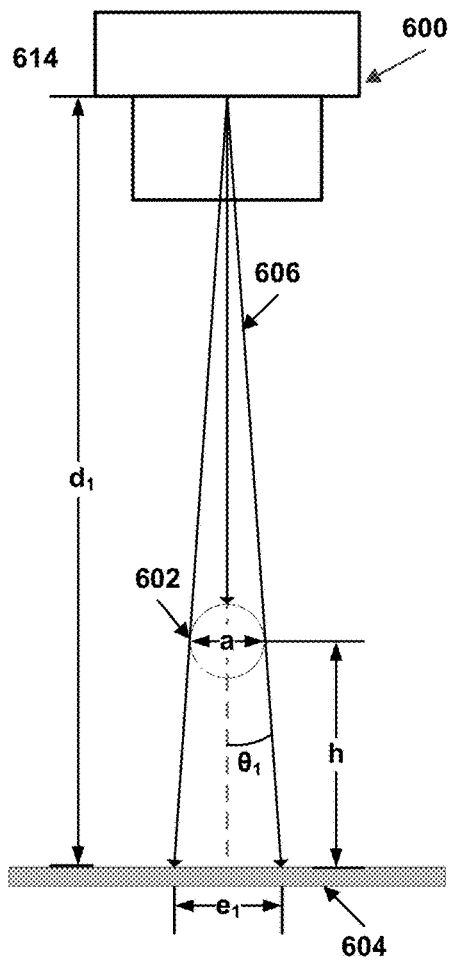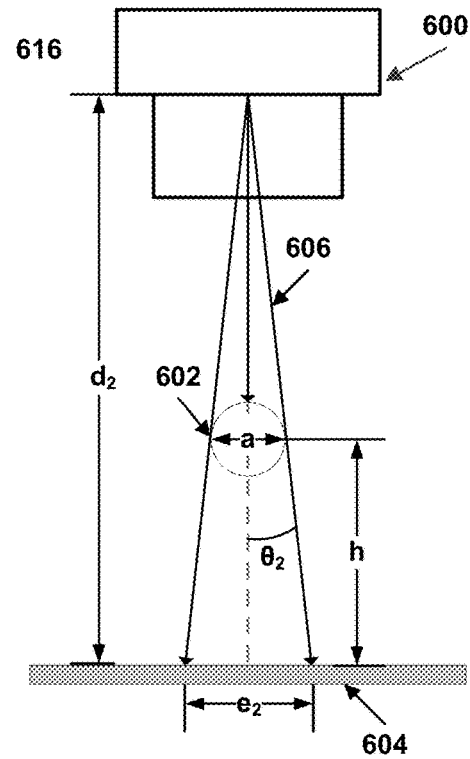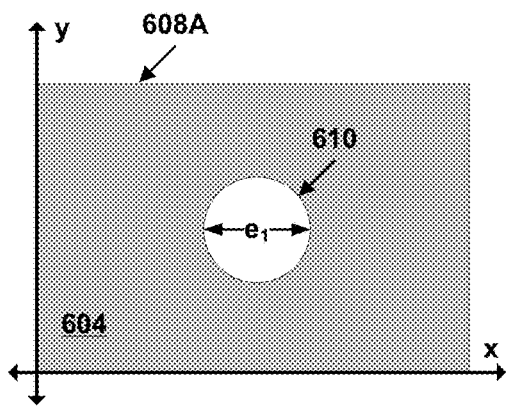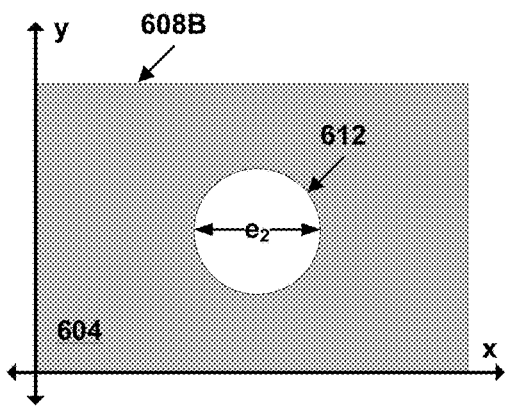
Fig. 6A  Fig. 6B

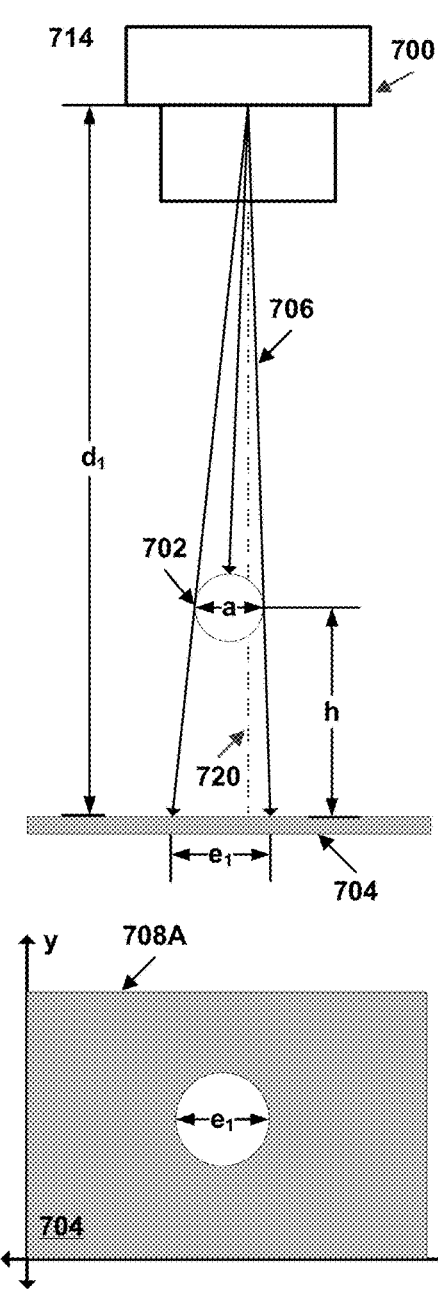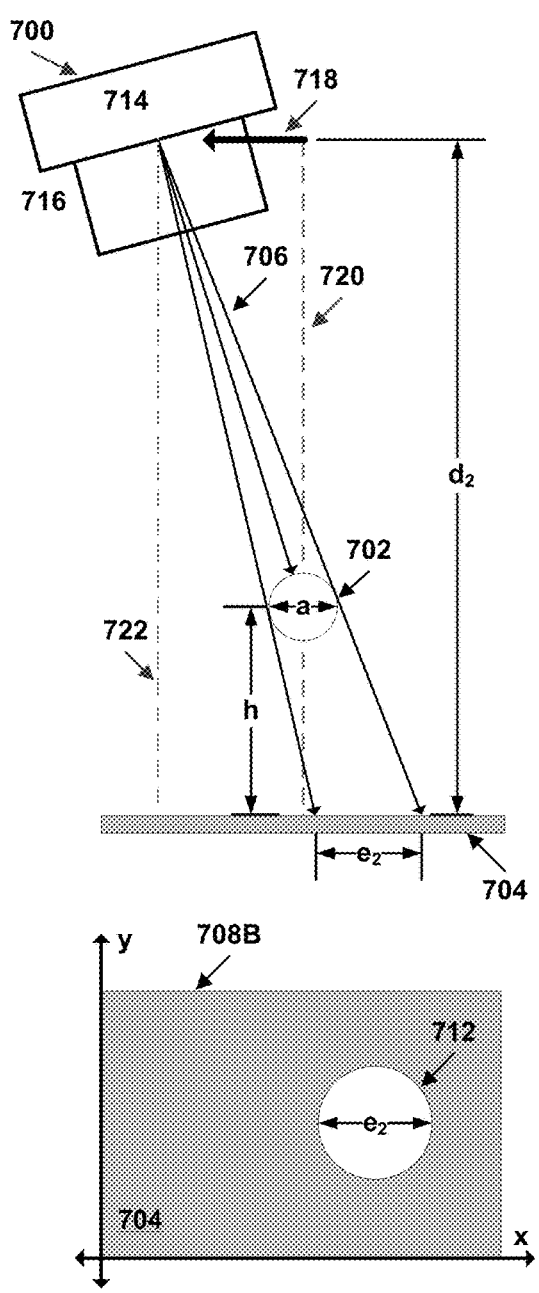
Fig. 7A
Fig. 7B

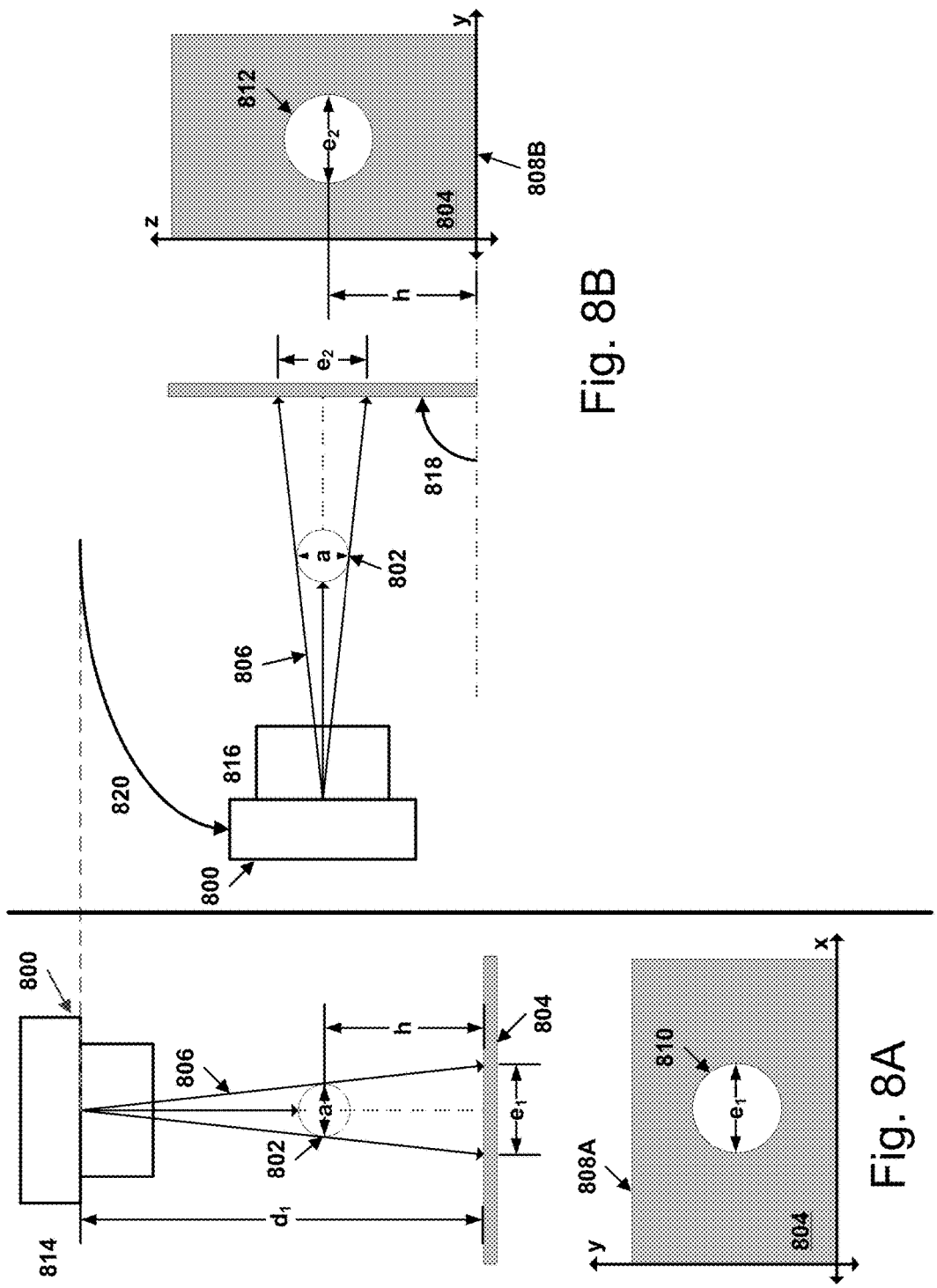

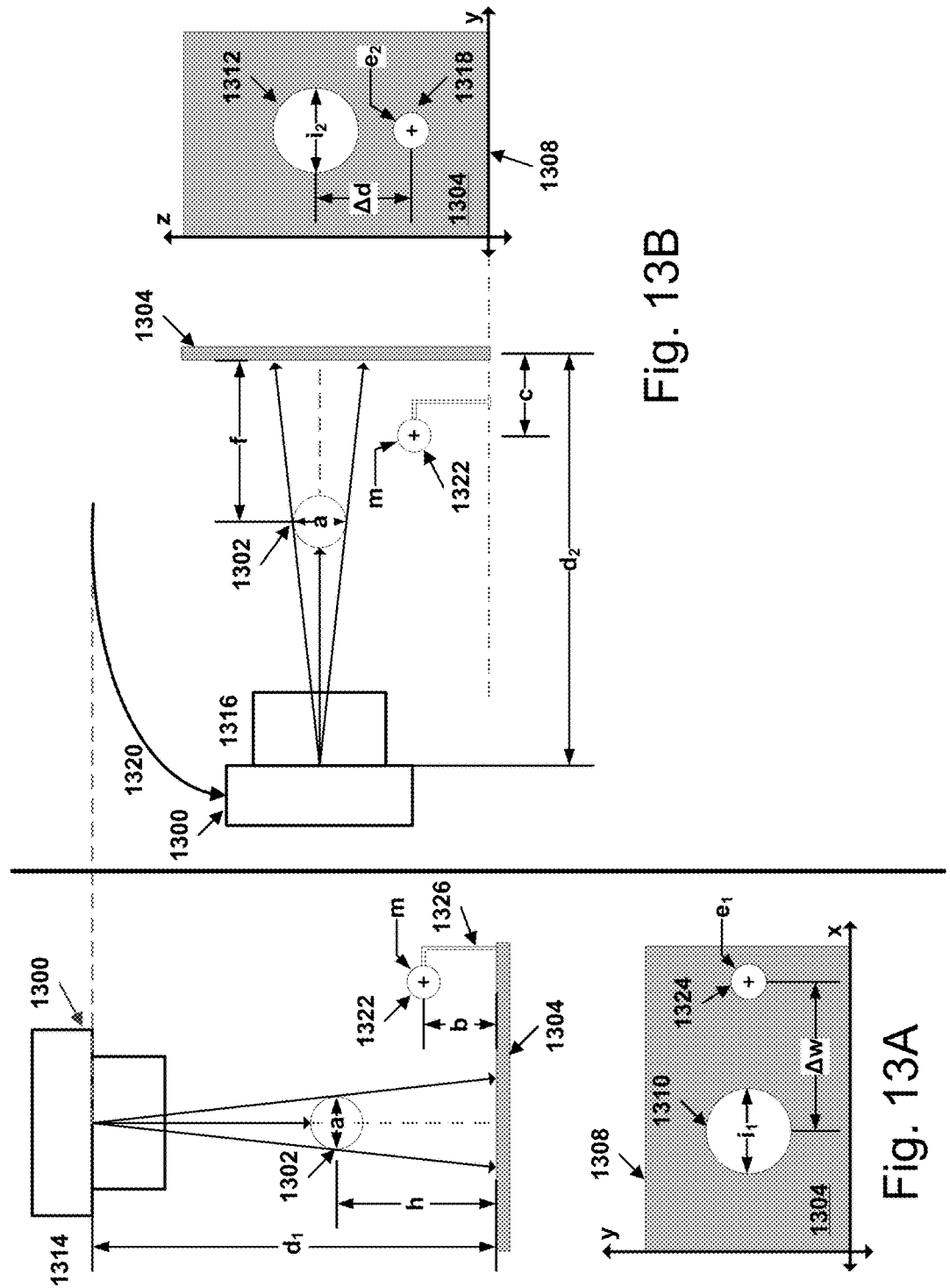

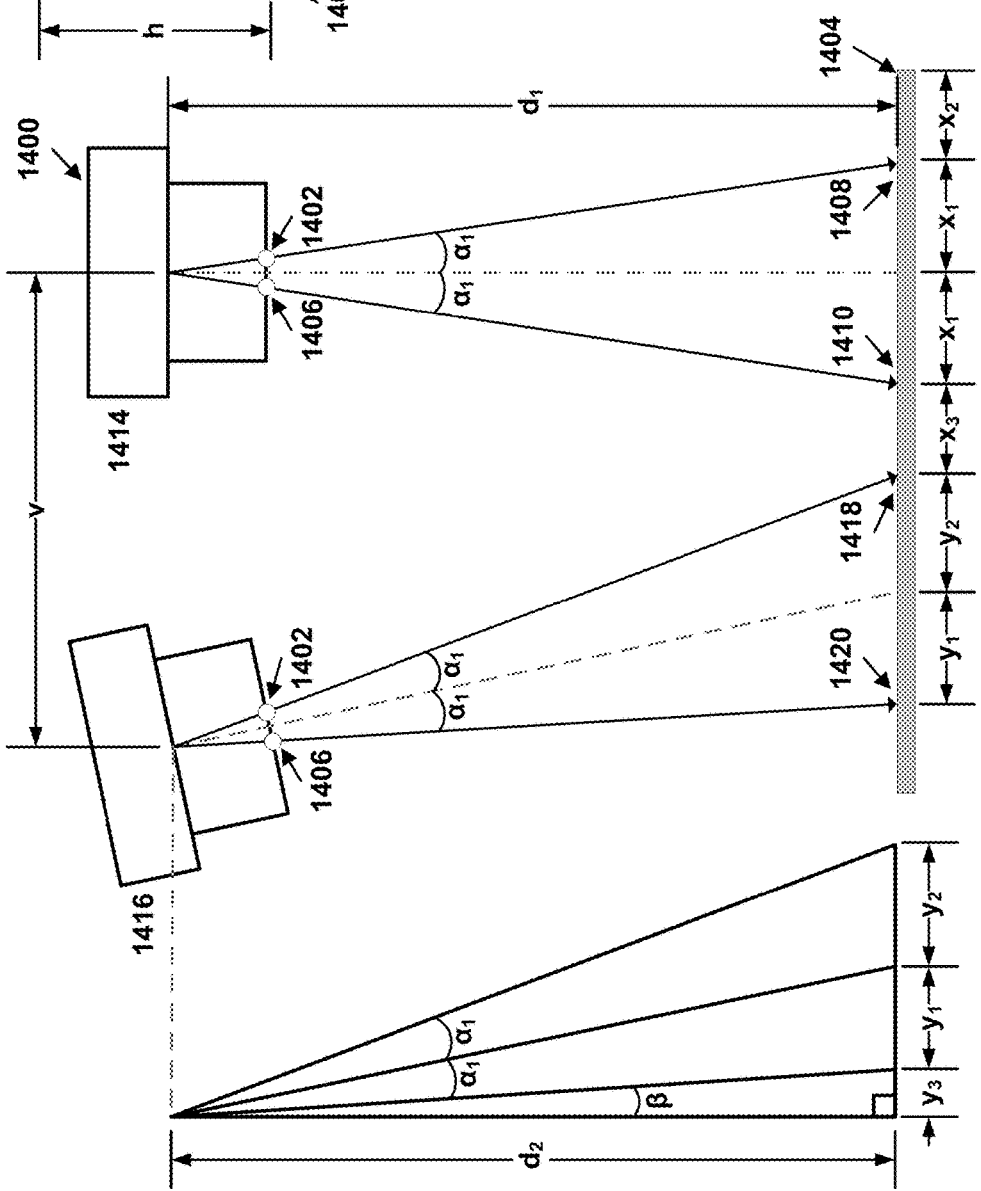

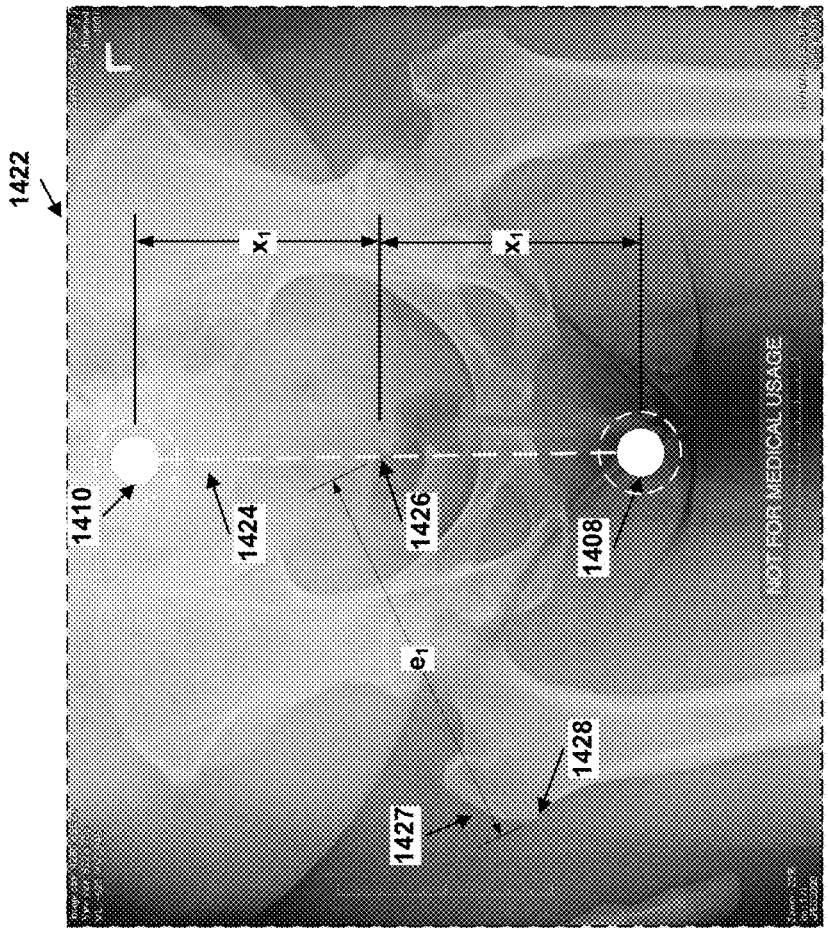
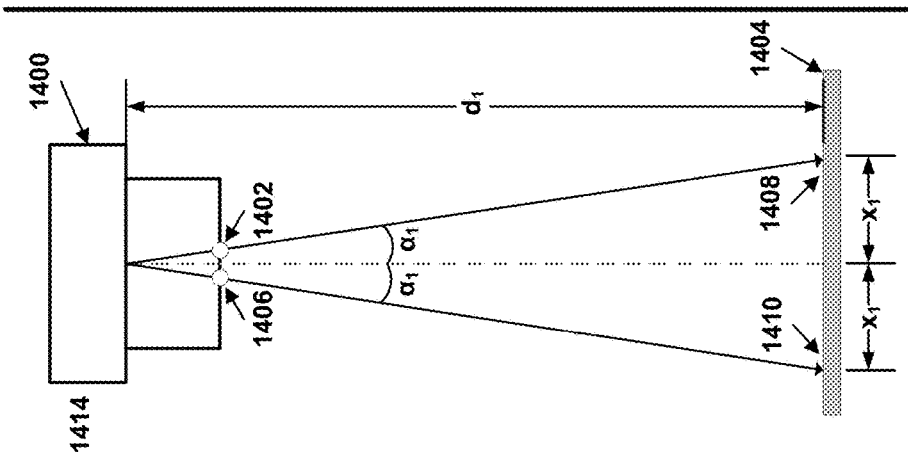
Fig. 14D
Fig. 14C

ACCURATE RADIOGRAPHIC CALIBRATION USING MULTIPLE IMAGES

BACKGROUND

Orthopedic joint replacement surgeries such as hip replacement and knee replacement typically involve replacing a damaged bone or joint with a prosthetic implant. Similarly, orthopedic stabilization surgeries involve bracing or fixating an injured bone so that it heals properly. The prosthetic implant or brace is shaped in a way that allows movement similar to that of a healthy joint.

In order for an orthopedic replacement procedure to be successful, a physician anticipates both the size and shape of the prosthetic implant that will most closely match the anatomy of the patient. This is often done based on radiographic (i.e., X-ray) images of the patient's joint and the associated bone structure. If the size and shape are estimated incorrectly, the necessary prosthetic implant might be unavailable during surgery. A prosthesis of incorrect size might be implanted, leading to complications.

SUMMARY

In the field of medicine, it is often useful to identify the magnification of an object or objects (e.g., blood vessels, tumors, bones, hardware implants) within a radiograph or a representation of a radiograph. Knowing the magnification of different body parts within a radiograph enables medical professionals to determine their actual physical size.

For example, in orthopedic surgery, medical professionals often measure the size of multiple objects including hardware implants, bones, joints and bone lesions. This enables the medical professional to determine: 1) if a bone lesion has changed in size, 2) a fracture has significantly displaced, or 3) what type and size of hardware is required to reconstruct a joint, a bone, or stabilize a fracture.

In order for an orthopedic replacement procedure to be successful, a physician may need to anticipate both the size and shape of the prosthetic implant that will most closely match the anatomy of a patient. Traditionally, the physician may manually size implants based on radiographs of the patient's joint and the associated bone structure. The physician may place a clear sheet, called a template, containing an outline in the size and shape of the prosthetic implant over the radiograph. The template may include anatomical reference markings. Given that radiographs and the images contained therein are typically magnified by approximately 10% to 25%, the template is also typically magnified to account for the anticipated magnification of the patient's bone structure when a radiograph is taken.

Using multiple templates in a trial-and-error fashion, the physician may eventually select a size for the prosthetic implant. However, as different anatomical features of a joint are located at different heights, they are magnified to a different extent. Additionally, radiographic magnification also varies among people with different body habitus (e.g., obese, very muscular). Unfortunately, the traditional templating process only approximates the magnification for the radiograph and assumes that this approximation applies equally to all anatomical features depicted in the radiograph. As a result, the traditional approach may result in the selection of a prosthetic implant of the wrong size.

In order to overcome this problem, some physicians place a sizing marker on the radiograph that enables them to more accurately determine the magnification of the radiograph and the images contained therein. Once the radiograph has been templated, the physician then adjusts the selected prosthesis size by the determined magnification. However, since the template is not resized to the correct magnification prior to being placed over the radiograph, the incorrectly sized template can be placed in the incorrect position. Accordingly, using a sizing marker does not improve the accuracy of the templating process.

With the introduction of digital imaging, traditional templating is being replaced by digital templating. With digital templating, the physician views a representation of the radiograph on a computer and uses a digital representation of the template to select a replacement prosthesis closest in size and shape to the anatomical features of the patient. Digital templating has a significant advantage over traditional methods in that digital templates are not limited to one size magnification. Templating software enables either the templates or the radiograph to be adjusted to the correct magnification prior to placement of the template. However, digital templating still has one major weakness. Namely, it does not have a reliable and reproducible method of determining the magnification of an object image or object images within a radiograph. As a result, despite the advantages of software, it is often just as inaccurate as templating using traditional template overlays.

To determine the magnification of an object image within a radiograph, a calibration process is required that precisely determines the height of that object above a radiographic receiver at the time when the radiograph was obtained. Unfortunately, as described below, existing methods are not reliable as some of them depend on marker placement by a medical professional at an estimated height of an object deep within the human body. Not only is this method fraught with human error, the error is not readily identifiable while a user is templating the object image within the radiograph. Thus, the user might not know if the templating results are accurate.

Additional weaknesses exist with current methods of calibration. Present methods of calibration apply the same scaling factor to all object images within a radiograph as they do not have a way of determining the height of different objects of interest depicted within a radiograph. As a result, multiple objects cannot be templated accurately as they are often at different heights than the calibration marker.

Finally, when only a single magnification factor is applied across the entire radiograph, additional information such as the rotational position of an object depicted within the radiograph cannot be determined. Since joint and bone rotation often determine the shape of template chosen, without knowing the rotation of the joint at the time the radiograph was taken, the selected prosthetic implant often does not accurately reflect the anatomy of the patient's joint.

Health care providers (e.g., hardware manufacturers, hospital systems, and medical professionals) have attempted to leverage the preoperative measurement capabilities of digital templating to reduce the cost of care and improve patient outcomes. In particular, accurately determining the size of a bone or joint prior to surgery may improve patient outcomes and reduce the cost of supplying medical hardware to the operating room by narrowing the range of hardware that needs to be available on-hand during surgery. Manufacturers of the medical hardware may consequently produce, transport, and store less hardware. Likewise, hospital systems may keep fewer products on the shelf and may reduce surgical cost associated with preoperative hardware management and operative time. Additionally, accurate preoperative measurements may reduce surgical time and facilitate a significant reduction in operative complications by providing hardware that most closely matches the size and shape of a patent's anatomical features.

Determining the actual physical size of a patient's anatomical features (e.g., bones and bone features) may be of notable importance in a cost-conscious medical environment for additional reasons. In particular, as hospital systems attempt to reduce costs by decreasing the hardware and accessories available off the shelf in the operating room, the correct hardware may be unavailable intraoperatively if the size and shape of the patient's anatomical features were not accurately determined prior to surgery. Similarly, if a patient has abnormally sized joints or is an unusual variant with respect to body composition, off-the-shelf hardware may not match the patient's anatomy and the patient may require customized replacement hardware. If the size of the patient's anatomical features is not determined accurately, the customized hardware may not be a good fit.

Inaccurate preoperative templating may prolong surgery and may cause a surgeon to place incorrectly sized hardware on the patient, leading to complications. Complications may include, but are not limited to, non-healing, chronic pain, deformity, instability, nonvascular injury, deep venous thrombosis, pulmonary embolus, infection, and/or cardiac/respiratory compromise. Additionally, surgically implanting an oversized prosthesis in a patient may result in an increased incidence of femoral fracture, excess leg length, or nerve palsy. Conversely, hardware loosening, shortened leg length, or hip dislocation may result from implanting undersized hardware.

The embodiments described herein are generally directed to determining the magnification of an image of an object of interest in a radiograph by using at least two different radiographs, each radiograph captured from a different orientation. In contrast to existing digital templating solutions, the example embodiments described herein are not limited to applying the same level of magnification to images corresponding to different objects of interest contained within the same radiograph. Example embodiments may determine a plurality of levels of magnification, each corresponding to a different anatomical feature or object of interest, the images of which may be contained within a radiograph.

Additionally, example embodiments are also directed at determining the position and orientation of multiple objects based on at least two different radiographs. For example, the embodiments described herein may be used to determine the degree of femoral anteversion or retroversion based on at least two different radiographs, each acquired from a different perspective. While prior methods might not accurately account for femoral rotation, the embodiments described herein enable accurate measurement by placing templates at a rotation that substantially matches the determined rotation of the femur at the time of capturing the radiograph. As a result, no special patient positioning is required. The methods described herein are not limited to the hip and femur but may also be used for any body part of interest.

In one example, an embodiment is provided that includes obtaining, by a computing device, a representation of a first radiograph containing a first image of an object of interest. The first radiograph may be captured by a radiographic device with a radiation source and a radiation receiver in a first orientation. The embodiment also includes obtaining, by the computing device, a representation of a second radiograph containing a second image of the object of interest. The second radiograph may be captured by the radiographic device with the radiation source and the radiation receiver in a second orientation. The embodiment additionally includes, based on a first width of the first image and a second width of the second image, determining a vertical distance of the object of interest above the radiation receiver. Based on the vertical distance of the object of interest above the radiation receiver, the embodiment further includes determining a magnification of the object of interest in one of the first radiograph and/or the second radiograph. The determined magnification may be used to scale the image of the object of interest contained in one of the first radiograph and/or the second radiograph in order to represent a physical size of the object of interest. The scaled image may be used to select, from a plurality of surgical templates of different sizes, a surgical template closest in size to the physical size of the object of interest.

In another example, a radiographic system is disclosed that includes a radiation source and a radiation receiver. At least one of the radiation source and the radiation receiver is movable with respect to one another. The radiographic system also includes a processor, a memory, and program instructions stored in memory. The program instructions, when executed by the processor, cause the radiographic system to perform operations that include capturing a first radiograph containing a first image of an object of interest with the radiation source and the radiation receiver in a first orientation with respect to one another. The operations further include storing, in the memory, the first radiograph and metadata representing vertical and horizontal positions of the radiation source and the radiation receiver in the first orientation. The operations additionally include moving at least one of the radiation source and the radiation receiver so that the radiation source and the radiation receiver are in a second orientation with respect to one another. The operations further include capturing a second radiograph containing a second image of the object of interest with the radiation source and the radiation receiver in the second orientation. The operations also include storing, in the memory, the second radiograph and metadata representing vertical and horizontal positions of the radiation source and the radiation receiver in the second orientation. Based on the captured radiographs and one or more of the vertical and horizontal positions of the first and second orientations, the operations additionally include determining a magnification of the object of interest as represented by the first image or the second image.

A further example discloses a non-transitory computer readable medium having stored thereon instructions that, when executed by a processor, cause the processor to perform operations. The operations include obtaining a representation of a first radiograph containing a first image of an object of interest. The first radiograph may be captured by a radiographic device with a radiation source and a radiation receiver in a first orientation. The operations also include obtaining a representation of a second radiograph containing a second image of the object of interest. The second radiograph may be captured by a radiographic device with a radiation source and a radiation receiver in a second orientation. The operations further include, based on a first width of the first image, and a second width of the second image, determining a vertical distance of the object of interest above the radiation receiver. The operations yet further include determining a magnification of the object of interest in one of the first radiograph or the second radiograph based on the vertical distance of the object of interest above the radiation receiver. Based on the determined magnification, the operations may also include selecting, from a plurality of template objects of different sizes, a template object closest in size to a physical size of the object of interest.

Another example embodiment may include a means for obtaining a representation of a first radiograph containing a first image of an object of interest, where the first radiograph was captured by a radiographic device with a radiation source and a radiation receiver in a first orientation. The example embodiment may also include means for obtaining a representation of a second radiograph containing a second image of the object of interest, wherein the second radiograph was captured by the radiographic device with the radiation source and the radiation receiver in a second orientation. The embodiment may additionally include means for determining, based on a first width of the first image of the object of interest in the first radiograph, and a second width of the second image of the object of interest in the second radiograph, a vertical distance of the object of interest above the radiation receiver. The embodiment may further include means for determining, based on the vertical distance of the object of interest above the radiation receiver, a magnification of the object of interest in one of the first radiograph or the second radiograph.

In a different example, an embodiment is provided that include obtaining, by a computing device, a representation of a first radiograph containing a first image of an object of interest. The first radiograph may be captured by a radiographic device with a radiation source and a radiation receiver in a first orientation. The operations also include obtaining a representation of a second radiograph containing a second image of the object of interest. The second radiograph may captured by a radiographic device with a radiation source and a radiation receiver in a second orientation. The embodiment additionally includes determining a first distance between the first image and a reference point in the representation of the first radiograph based on the representation of the first radiograph. The embodiment further includes determining a second distance between the second image and the reference point in the representation of the second radiograph based on the representation of the second radiograph. The embodiment yet further includes determining a vertical distance of the object of interest above the radiation receiver based on the first distance and the second distance. The embodiment also includes, based on the vertical distance of the object of interest above the radiation receiver, determining a magnification of the object of interest in one of the first radiograph or the second radiograph. The determined magnification may be used to scale the image of the object of interest contained in one of the first radiograph and/or the second radiograph in order to represent a physical size of the object of interest. The scaled image can be used to select, from a plurality of surgical templates of different sizes, a surgical template closest in size to the physical size of the object of interest.

In another example, a radiographic system is disclosed that includes a radiation source and a radiation receiver. At least one of the radiation source and the radiation receiver is movable with respect to one another. The radiographic system also includes a processor, a memory, and program instructions stored in memory. The program instructions, when executed by the processor, cause the radiographic system to perform operations that include capturing a first radiograph containing a first image of an object of interest with the radiation source and the radiation receiver in a first orientation with respect to one another. The operations further include storing, in the memory, a representation of the first radiograph and metadata representing vertical and horizontal positions of the radiation source and the radiation receiver in the first orientation. The operations additionally include moving at least one of the radiation source and the radiation receiver so that the radiation source and the radiation receiver are in a second orientation with respect to one another. The operations further include capturing a second radiograph containing a second image of the object of interest with the radiation source and the radiation receiver in the second orientation. The operations also include storing, in the memory, a representation of the second radiograph and metadata representing vertical and horizontal positions of the radiation source and the radiation receiver in the second orientation. The operations additionally include determining, based on the representation of the first radiograph, a first distance between the first image and a reference point in the representation of the first radiograph. The operations further include determining, based on the representation of the second radiograph, a second distance between the second image and the reference point in the representation of the second radiograph. Based on the first distance, the second distance, and one or more of the vertical and horizontal positions of the first and second orientations, the operations additionally include determining a magnification of the object of interest as represented by the first image or the second image.

A further example discloses a non-transitory computer readable medium having stored thereon instructions that, when executed by a processor, cause the processor to perform operations. The operations include obtaining a representation of a first radiograph containing a first image of an object of interest. The first radiograph may be captured by a radiographic device with a radiation source and a radiation receiver in a first orientation. The operations also include obtaining a representation of a second radiograph containing a second image of the object of interest. The second radiograph may be captured by a radiographic device with a radiation source and a radiation receiver in a second orientation. The operations further include determining a first distance between the first image and a reference point in the representation of the first radiograph based on the representation of the first radiograph. The operations also include determining a second distance between the second image and the reference point in the representation of the second radiograph based on the representation of the second radiograph. The operations further include determining a vertical distance of the object of interest above the radiation receiver based on the first distance and the second distance. The operations yet further include, based on the vertical distance of the object of interest above the radiation receiver, determining a magnification of the object of interest in one of the first radiograph or the second radiograph. Based on the determined magnification, the operations may also include selecting, from a plurality of template objects of different sizes, a template object closest in size to a physical size of the object of interest.

Another example embodiment includes a means for obtaining a representation of a first radiograph containing a first image of an object of interest. The first radiograph may be captured by a radiographic device with a radiation source and a radiation receiver in a first orientation. The example embodiment may also include means for obtaining a representation of a second radiograph containing a second image of the object of interest. The second radiograph may captured by a radiographic device with a radiation source and a radiation receiver in a second orientation. The example embodiment may additionally include means for determining a first distance between the first image and a reference point in the representation of the first radiograph based on the representation of the first radiograph. The example embodiment may further include means for determining a second distance between the second image and the reference point in the representation of the second radiograph based on the representation of the second radiograph. The example embodiment may yet further include means for determining a vertical distance of the object of interest above the radiation receiver based on the first distance and the second distance. The example embodiment may also include, means for determining, based on the vertical distance of the object of interest above the radiation receiver, a magnification of the object of interest in one of the first radiograph or the second radiograph. The example embodiment may include means for scaling, based on the determined magnification, the image of the object of interest contained in one of the first radiograph and/or the second radiograph in order to represent a physical size of the object of interest. The example embodiment may include means for selecting, based on the scaled image of the object of interest, a surgical template closest in size to the physical size of the object of interest, where the surgical template is selected from a plurality of surgical templates of different sizes.

BRIEF DESCRIPTION OF THE DRAWINGS

FIG. 5A illustrates a radiation source positioned above a receiver, according to an example embodiment.

FIG. 5B illustrates a coordinate system attached to a receiver, according to an example embodiment.

FIGS. 6A and 6B illustrate the acquisition of radiographs from different vertical radiation source positions, according to an example embodiment.

FIGS. 7A and 7B illustrate the acquisition of radiographs from different vertical and horizontal radiation source positions and angular orientations, according to an example embodiment.

FIGS. 8A and 8B illustrate the acquisition of radiographs involving a rotation of the radiation receiver, according to an example embodiment.

FIGS. 13A and 13B illustrate a calibration marker being used to determine a height of an object, according to an example embodiment.

FIGS. 14A and 14B illustrate a calibration marker attached to a radiation source, according to an example embodiment.

FIGS. 14C-14E illustrate an alternative approach of determining a height of an object of interest, according to an example embodiment.

DETAILED DESCRIPTION

Figure 1:
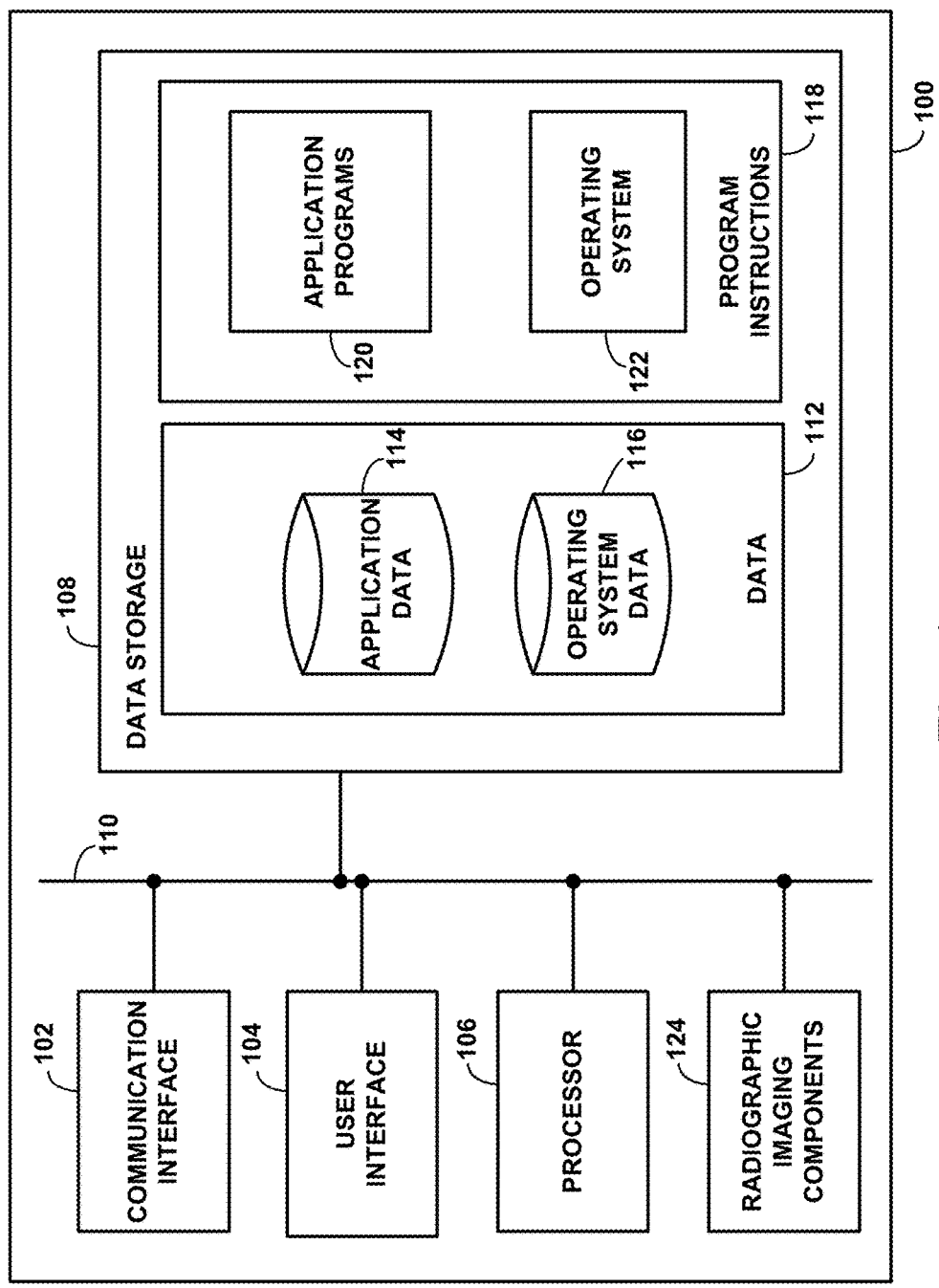
FIG. 1 illustrates a block diagram of a computing device; according to an example embodiment.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. Aspects of the present disclosure, as generally described herein, and illustrated in the figures, can be arranged, substituted, combined, separated, and designed in a wide variety of different configurations, all of which are contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

I. OVERVIEW

The embodiments described herein are generally directed at determining the magnification of an image of an object on a radiograph based on at least two different radiographs. Example embodiments are also directed at determining the position and orientation of multiple objects based on at least two different radiographs. In an example embodiment, a first radiograph of an object of interest may be obtained. A second radiograph of the object of interest may be subsequently obtained from a different position, perspective, viewpoint, and/or orientation between a radiation source and a radiation receiver than the first radiograph. Information from the two radiographs may be used in combination in order to determine a size (e.g., width, diameter), position, orientation, and/or magnification of the object of interest. While the first and second radiographs are two-dimensional (2D), the methods described herein may enable the determination of three-dimensional (3D) information such as position and orientation of an object of interest based on a combination of the information contained in the two radiographs. The embodiments described herein may be used with templating techniques in order to determine a template object closest in size to the object of interest.

For example, the embodiments herein may be used to accurately template a replacement prosthesis for a human hip joint using manual or digital templating methods. A first radiograph of the hip may be obtained. A second radiograph of the hip may subsequently be obtained from a different position, perspective, viewpoint, and/or orientation between a radiation source and a radiation receiver than the first radiograph. The two radiographs may be used in combination to determine the heights and levels of magnification corresponding to different anatomical features of the hip. Portions of at least one of the two radiographs (wherein the portions are parts of images representing the different anatomical features) may be scaled according to the corresponding levels of magnification. The scaled portions may accurately represent the physical size and/or dimensions of the corresponding anatomical features. Additionally, based at least on the determined heights of the different anatomical features, an orientation of at least portions of the hip may be determined. For example, the rotation of the femur with respect to the pelvis may be determined based on the heights of the femoral head and the femoral calcar. The scaled portions of the radiograph and the determined orientation of at least portions of the hip may be used in combination with digital templating to find a prosthesis that most closely matches the anatomical dimensions of the hip.

In the examples that follow, the different perspective of the second radiograph relative to the first radiograph may be achieved by moving a source of radiation (e.g., an X-ray emitter) relative to a radiation receiver (e.g. film, cassette, digital detector array) while keeping the receiver stationary. Alternatively, the different perspective may be achieved by moving the receiver relative to the radiation source while keeping the source stationary. It may also be possible to move both the source and receiver in combination, provided that the relative change in position and orientation of the radiation source relative to the receiver between the first radiograph and second radiograph is known, measured, determined, and/or accounted for in any relevant calculations. Moving the source and/or receiver may include horizontal translation, vertical translation, angular rotation, and/or any combination thereof.

II. EXAMPLE COMPUTING DEVICE

The methods, operations, and/or example embodiments described herein may be integrated into and/or performed by a computing device. The computing device may be, for example, a wireless computing device, tablet computer, desktop computer, laptop computer and/or a specialized computer integrated with a radiographic imaging device. For purposes of example, FIG. 1 is a simplified block diagram showing some of the components of an example computing device 100 that may include radiographic imaging components 124. However, computing device 100 does not require radiographic imaging components 124 in the embodiments described herein.

By way of example and without limitation, computing device 100 may be a cellular mobile telephone (e.g., a smartphone), a computer (such as a desktop, notebook, tablet, handheld computer, or a specialized, purpose-built computer integrated with a radiographic imaging device), a medical device, a personal digital assistant (PDA), a home or business automation component, a digital television, or some other type of device capable of operating in accordance with the example embodiments described herein. It should be understood that computing device 100 may represent a physical radiographic imaging device such as an X-ray imaging device, a particular physical hardware platform programmed to carry out and/or provide instructions to a radiographic imaging device to carry out the operations described herein, or other combinations of hardware and software that are configured to carry out the disclosed functions and operations.

As shown in FIG. 1, computing device 100 may include a communication interface 102, a user interface 104, a processor 106, data storage 108, and radiographic imaging components 124, all of which may be communicatively linked together by a system bus, network, or other connection mechanism 110.

Communication interface 102 may allow computing device 100 to communicate, using analog or digital modulation, with other devices, access networks, and/or transport networks. Thus, communication interface 102 may facilitate circuit-switched and/or packet-switched communication, such as plain old telephone service (POTS) communication and/or Internet protocol (IP) or other packetized communication. For instance, communication interface 102 may include a chipset and antenna arranged for wireless communication with a radio access network or an access point. Also, communication interface 102 may take the form of or include a wireline interface, such as an Ethernet, Universal Serial Bus (USB), or High-Definition Multimedia Interface (HDMI) port. Communication interface 102 may also take the form of or include a wireless interface, such as a Wifi, BLUETOOTH®, global positioning system (GPS), or wide-area wireless interface (e.g., WiMAX or 3GPP Long-Term Evolution (LTE)). However, other forms of physical layer interfaces and other types of standard or proprietary communication protocols may be used over communication interface 102. Furthermore, communication interface 102 may comprise multiple physical communication interfaces (e.g., a Wifi interface, a BLUETOOTH® interface, and a wide-area wireless interface).

User interface 104 may function to allow computing device 100 to interact with a human or non-human user, such as to receive input from a user and to provide output to the user. Thus, user interface 104 may include input components such as a keypad, keyboard, touch-sensitive or presence-sensitive panel, computer mouse, trackball, joystick, microphone, and so on. User interface 104 may also include one or more output components such as a display screen that, for example, may be combined with a presence-sensitive panel. The display screen may be based on cathode ray tube (CRT), liquid-crystal display (LCD), and/or light-emitting diode (LED) technologies, or other technologies now known or later developed. User interface 104 may also be configured to generate audible output(s), via a speaker, speaker jack, audio output port, audio output device, earphones, and/or other similar devices.

In some embodiments, user interface 104 may include one or more buttons, switches, knobs, and/or dials that facilitate the configuration of a radiographic imaging device and the capturing or acquiring of radiographs and/or representations of radiographs. It may be possible that some or all of these buttons, switches, knobs, and/or dials are implemented by way of a presence-sensitive panel.

Processor 106 may comprise one or more general purpose processors—e.g., microprocessors—and/or one or more special purpose processors—e.g., digital signal processors (DSPs), graphics processing units (GPUs), floating point units (FPUs), network processors, or application-specific integrated circuits (ASICs). In some instances, special purpose processors may be capable of image processing, image alignment, merging images, and feature detection (e.g. geometric feature such as a square, circle, or an approximation thereof) among other possibilities. Data storage 108 may include one or more volatile and/or non-volatile storage components, such as magnetic, optical, flash, or organic storage, and may be integrated in whole or in part with processor 106. Data storage 108 may include removable and/or non-removable components.

Processor 106 may be capable of executing program instructions 118 (e.g., compiled or non-compiled program logic and/or machine code) stored in data storage 108 to carry out the various functions described herein. Therefore, data storage 108 may include a non-transitory computer-readable medium, having stored thereon program instructions that, upon execution by computing device 100, cause the computing device 100 to carry out any of the methods, processes, or operations disclosed in this specification and/or the accompanying drawings. The execution of program instructions 118 by processor 106 may result in processor 106 using data 112.

By way of example, program instructions 118 may include an operating system 122 (e.g., an operating system kernel, device driver(s), and/or other modules) and one or more application programs 120 (e.g., camera functions, image processing functions, address book, email, web browsing, social networking, and/or gaming applications) installed on computing device 100. Similarly, data 112 may include operating system data 116 and application data 114. Operating system data 116 may be accessible primarily to operating system 122, and application data 114 may be accessible primarily to one or more of application programs 120. Application data 114 may be arranged in a file system that is visible to or hidden from a user of computing device 100.

Application programs 120 may communicate with operating system 122 through one or more application programming interfaces (APIs). These APIs may facilitate, for instance, application programs 120 reading and/or writing application data 114, transmitting or receiving information via communication interface 102, receiving and/or displaying information on user interface 104, and so on.

In some vernaculars, application programs 120 may be referred to as "apps" for short. Additionally, application programs 120 may be downloadable to computing device 100 through one or more online application stores or application markets. However, application programs can also be installed on computing device 100 in other ways, such as via a web browser or through a physical interface (e.g., a USB port) on computing device 100.

Radiographic imaging components 124 may include, but are not limited to, a radiation source, a radiation receiver, position feedback mechanisms configured to track the relative position between the radiation source and the radiation receiver, and/or any other components required for or intended to improve the function of a radiation imaging system or apparatus as described herein or otherwise known in the art. Radiation imaging components 124 may be controlled at least in part by software instructions executed by processor 106. Radiation imaging components 124 may also provide information to processor 106, user interface 104, communication interface 102, and/or data storage 108 indicating the relative spatial positioning of at least some of the radiographic imaging components 124.

It should be understood that the components of the computing device may be distributed, logically or physically, over multiple devices of the same or of a different type. Additionally, multiple computing devices may work in combination to perform the operations described herein. For example, a specialized computing device local to a radiographic imaging apparatus may be used to capture, store, and send at least one radiograph or representation of a radiograph to a remote computing device. The remote computing device may process the radiographs or representations of radiographs according to the example embodiments described herein. Other arrangements are possible.

III. TEMPLATING AND DIGITAL TEMPLATING

While many radiographic digital templating solutions are available and aim to provide accurate preoperative measurement of body parts, they have significant flaws. Specifically, existing solutions rely on an inaccurate and limited method of scaling radiographs and, as a result, only provide a gross estimation of the actual size of objects within a radiograph. Consequently, the existing solutions have limited to no use in reducing the cost of providing medical care and reducing surgical complications.

Existing digital templating solutions (e.g., plain radiographic templating solutions such as X-ray based templating) use one of two known methods of scaling radiographs. In one method, an object of known size, such as, for example, a coin, may be placed on a radiographic receiver (cassette) at the time of imaging a body part of interest. With all other factors kept constant, the magnification of the image of the body part increases as the distance between the body part and the radiographic receiver increases. Accordingly, the image of the object of known size (e.g., the coin) is measured and the entire radiograph may be scaled according to the size of the image in relation to the actual, known size of the object. The scaling further assumes or estimates, based on the particular body part being measured, the average distance between the body part and the radiographic receiver based on standardized anthropometric data of the average person from several decades ago.

However, this method has serious flaws in that it does not account for anthropometric and physiologic (e.g., obesity, muscularity, etc.) variations among humans. Consequently, the actual height of the object or objects of interest is not truly known. Accordingly, the determined level of magnification of the object or objects of interest may be inaccurate since the actual height of the object or objects of interest is needed in order to determine the level of magnification. Additionally, this method incorrectly assumes that all objects within the radiograph are at the same distance from the radiographic receiver. As a result, this method does not accurately determine the magnification of different objects within radiographs for each individual patient. This method only provides an estimate for the average sized person and does not account for the fact that anatomical features of the human body are at different distances to the radiation receiver when the radiographs are captured. Consequently, this method cannot be used to accurately and reproducibly template bone features or bone lesions.

The second method relied upon by existing digital templating solutions requires the placement of an object of known size (e.g., a calibration marker) at the same height as the object of interest at the time of capturing the radiograph. By measuring the relative size between the calibration marker and the image of the calibration marker contained in the radiograph, the magnification of the image of the calibration marker in the radiographic image may be accurately determined. Accordingly, since the calibration marker is placed at the same height as the object of interest, the magnification of the object of interest is equal to the magnification of the marker. Theoretically, this second method is more accurate than the first method. However, in practice, even this second method faces significant limitations.

First, the second calibration marker method requires consistent and accurate placement of the calibration marker at the same height as the object of interest. The accuracy and consistency with which the marker is placed may vary between radiography technicians and medical professionals having different levels of experience, education, understanding of the importance of and interest in the accurate and consistent placement of the marker. As a result, significant human error may result in inaccurate determination of the magnification of the object of interest. Additionally, many large and obese patients may be larger than the radiation receiver used to capture the radiograph. As a result, if, while acquiring a hip radiograph, the marker is placed in the traditional position next to the greater trochanter of the femur, the marker may not appear in the image. The marker may need to be placed between the patient's legs, against the genitals, at approximately the same height as the greater trochanter and acetabulum. The marker may not visibly appear in the radiograph due to excess soft tissue obstructions or placement beyond the radiographic receiver. Consequently, the marker may need to be repositioned and multiple images may need to be captured to get the marker on a radiograph. This may lead to discomfort of the technician and the patient, and may result in inaccurate marker placement as well as an increased risk of disease transmission.

Second, even if a medical professional with impeccable understanding and grasp of the marker placement technique is used to place the marker, the medical professional still cannot accurately place the marker in all patients. In order to accurately place the marker, the medical professional must palpitate (feel) an anatomical feature or landmark (e.g. a bone feature) deep under the skin in order to determine the height of the object of interest. However, in very muscular or obese patients, the anatomical feature may not be palpable due to interposed soft tissue. As a result, the marker may only be placed at an approximate height of the object of interest.

Third, many deep anatomical features cannot be palpitated. In such cases, marker placement is decided by referencing another anatomical feature that can be palpitated. However, once again, this method requires that the referenced anatomical feature be at the same height as the object of interest and that the anatomical feature be palpable. For example, when templating hips for a total hip replacement, the magnification of the acetabulum may be determined. However, due to its location within the body, the acetabulum cannot be palpitated. Accordingly, the radiography technician or medical professional may have the patient internally rotate the hip by 15 degrees to account for femoral anteversion and place the greater trochanter of the femur, which can be palpitated, at approximately the same height as the acetabulum.

However, a technician may fail to internally rotate the hips by the prescribed amount. Additionally, many patients may not be able to internally rotate their hips by 15 degrees due to arthritis, stiffness, or mechanical obstructions. Furthermore, recent studies indicate that not all hips are anteverted 15 degrees, and that there is actually large variation in the degree of anteversion between individuals, often affected by the sex and race of the patient. In one study, it has been shown that up to 10% of African American males may have femoral retroversion. As a result, internally rotating the hips an average of 15 degrees may not only be inaccurate for the general population, but may actually worsen the accuracy of measurement in some individuals. As a result, even if the technologist internally rotated the hip with each patient and the patient is able to physically perform this maneuver, the marker placement often may not be at the same height as the acetabulum. Therefore, the magnification for the acetabulum might not be accurately determined. Worse, since this method is unable to measure femoral anteversion, the medical professional is unaware of any error in the process and will often use an incorrect measurement in planning and performing surgery.

Finally, just like the first calibration marker method, this approach assumes that all objects represented by the radiograph are located at the same height above the radiation receiver. The magnification of objects whose height is not equal to the height of the calibration marker is incorrect. Additionally, neither method provides any information about the rotational position of the object of interest. For example, neither method provides any information about the degree of rotation of the femur with respect to the pelvis. As a result, templating may be inaccurate, as the template used to size the femur cannot be rotated into the correct degree of rotation.

While more advanced methods such as magnetic resonance imaging (MRI) and computer tomography (CT) have been used to determine the size of anatomical features within a human body, these methods have several limitations of their own. First, MRI and CT scan devices may not be readily accessible, particularly in rural locations. Second, MRI and CT scans are costly and may not be covered by insurance. Third, CT scans may expose individuals to large doses of radiation, leading to malignancy. Finally, MRI and CT scans often require the individual to go to a different facility and are often not performed on the same day.

Figure 2A:
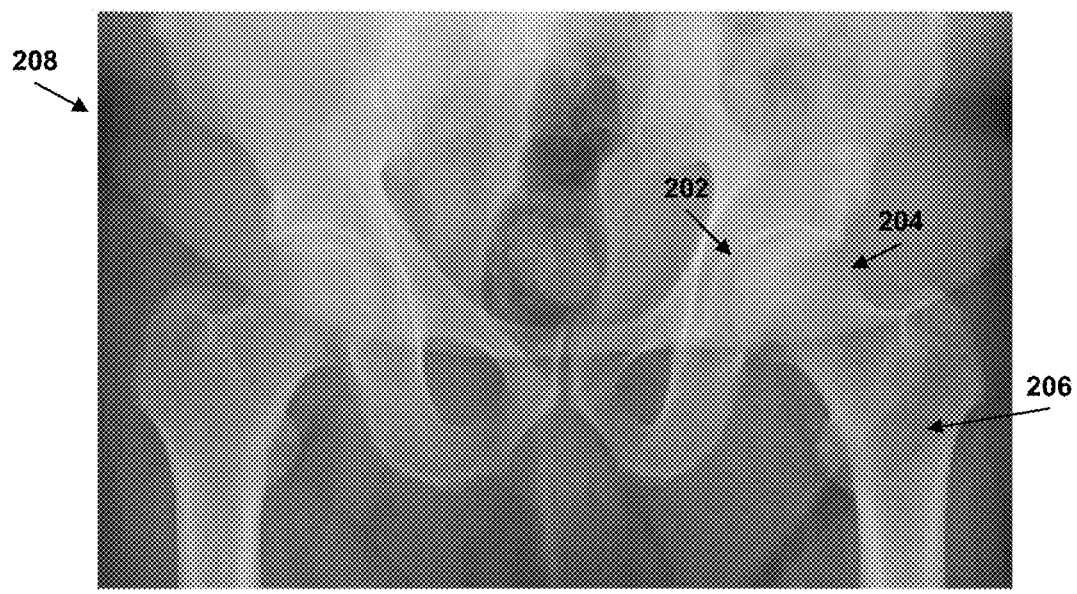
FIG. 2A represents a radiograph of a hip, according to an example embodiment.
Figure 2B:
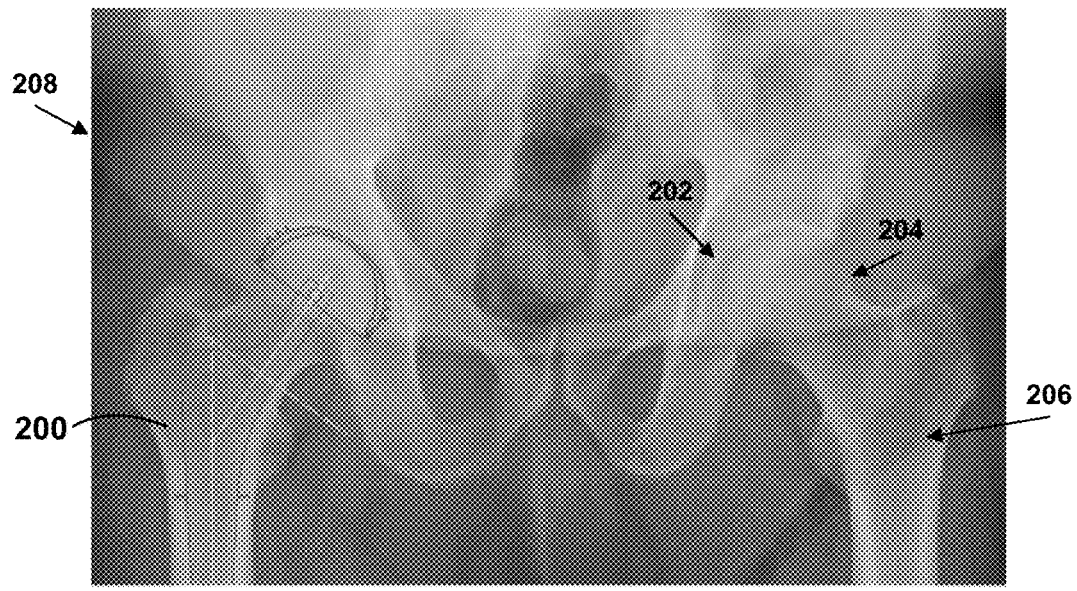
FIG. 2B represents a template object overlaid on the radiograph of FIG. 2A, according to an example embodiment.
Figure 4:
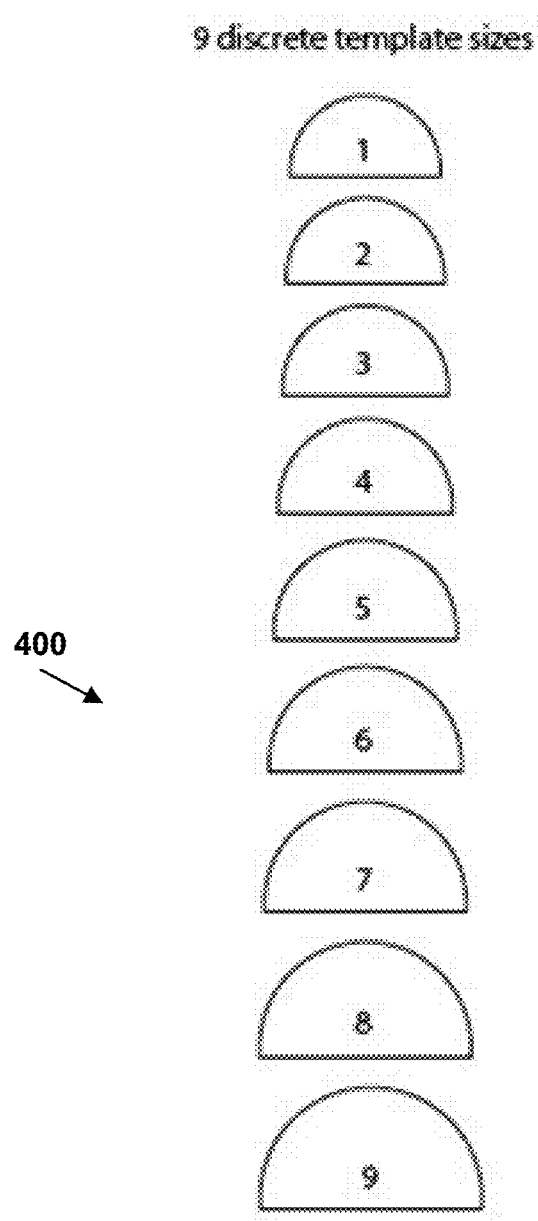
FIG. 4 represents a range of discrete template sizes, according to an example embodiment.

FIGS. 2A and 2B illustrate an example templating procedure. Specifically, FIG. 2A illustrates an anteroposterior (AP) radiograph 208 of a human hip. The radiograph 208 shows acetabulum image 202, femoral head image 204, and femoral calcar image 206. FIG. 2B illustrates a template object 200 overlaid atop the radiograph 208. The template 200 may be selected from a plurality of available templates, as shown in FIG. 4. The plurality of templates may represent a range of available sizes and shapes of replacement prostheses corresponding to the body part of interest (i.e. the body part shown on the radiograph being templated). In the present example, the replacement prostheses may be a hip replacement prosthesis. Alternatively, the replacement prostheses may be intended to replace anatomical features of the knee, elbow, shoulder, or any other jointed or non-jointed portions of bone or soft tissue.

An object of the templating process is to select a template object 200 that most closely matches or resembles the anatomy of the particular body part represented by radiograph 208. However, as previously discussed, in some existing templating and digital templating solutions, the images of the different anatomical features (e.g. acetabulum image 202, femoral head image 204, and femoral calcar image 206) contained in the radiograph 208 may be magnified to different, unknown extents and may be positioned in unknown or uncertain spatial orientations, leading to errors and inaccuracies in the selection of template 200. In contrast to existing solutions, the example embodiments disclosed herein allow for accurate determination of individual magnification levels where each individual magnification level is determined specifically for a particular object of interest or anatomical feature contained within the radiograph 208.

The radiograph 208 used in the templating process may be a radiographic film, a photocopy of the radiographic film, or a digital representation of the radiograph stored in a non-transitory computer readable medium of a computing device. Likewise, the template object 200, as well as the plurality of template objects from which template 200 is selected, may be a clear plastic film having printed thereon a one-to-one scale image of the template object. Templates representing different sizes of prostheses may be placed over the radiograph 208 until a template closest in size to the anatomical features represented by radiograph 208 is found. Alternatively, the template objects may be represented digitally on a computing device. The digital representation of the template may be overlaid on top of the digital representation of radiograph 208 using a computing device. The overlay may be visually displayed or illustrated on a display or user interface controlled by the computing device. As will be later discussed, portions of the radiograph 208 or the template objects may be scaled to accurately represent the physical size of the anatomical features of interest.

Figure 3:
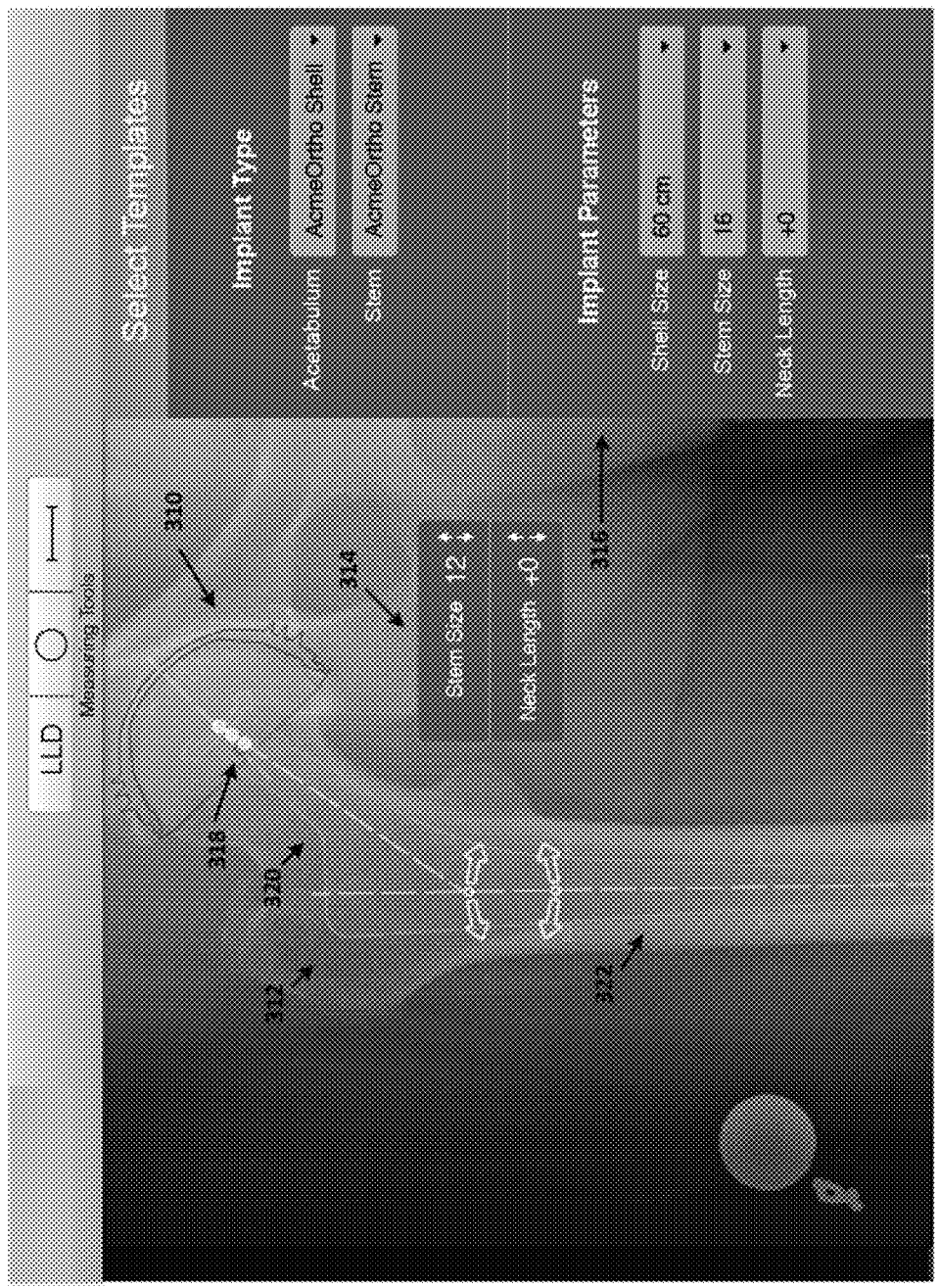
FIG. 3 represents a digital templating user interface, according to an example embodiment.

FIG. 3 represents an example graphical user interface that may be used with a digital templating process. Specifically, FIG. 3 illustrates a portion of an AP hip radiograph with template objects 310 and 322 overlaid thereon. The template objects 310 and 312 may represent a ball-and-socket joint of a prosthesis intended to replace the proximal aspect of the femur and the acetabular socket of the pelvis. The template object 310, also called a shell template, may be used to evaluate the replacement of the acetabular socket. The template object 312, also called a stem template, may be use to evaluate the replacement of the proximal aspect of the femur. The proximal aspect of the femur may include at least the femoral head and femoral neck. The template object 312 may represent a stem portion 322 and a neck portion 320 coupled to the ball portion of the stem template 312 at connection point 318.

The user interface of FIG. 3 may enable a user to manipulate a plurality of properties corresponding to template objects 310 and 312. For example, the user may specify a shell size of the template object 310. Likewise, the user may select a length of the neck portion 320, a size of the stem portion 322, as well as any other factors related to the sizing and positioning of the templates 310 and 312 over the radiograph. The plurality of properties corresponding to the template objects 310 and 312 may be selected from and correspond to a plurality of replacement prostheses available for purchase from different manufacturers.

Heads up display 314 and a series of drop-down menus 316 may be used to manipulate the properties of templates 310 and 312. For example, drop-down menus 316 may be used to select a prosthesis vendor, a particular prosthesis model offered by the vendor, a size for the shell prosthesis template 310, a size for stem 322, and a length for neck 320, among others. Heads up display 314 may be used to, for example, select a stem size and neck length of the template object 312. A computing device may execute program instructions causing the computing device to automatically select a template object closest in size, shape, and/or orientation to the anatomical features contained in a radiograph.

FIG. 4 illustrates an example range of nine discrete template sizes 400 corresponding to replacement prostheses. These templates may represent, for instance, the socket component of a ball-and-socket hip replacement prosthesis. Each of the nine discrete template sizes 400 is of a different size, and numbered from 1 to 9 in order of increasing size. Thus, template size 1 is smaller than template size 2, template size 2 is smaller than template size 3, and so on. In some embodiments, more or fewer that nine template sizes may be available. Templates may alternatively or additionally have different shapes in order to more closely match a given patient's anatomy. During the templating process, it may be possible to scale either the image of the particular object of interest (anatomical feature) contained in a radiograph or the template object based on the level of magnification determined to correspond to the particular object. Alternatively, a custom template object may be created and used in the templating process. A custom prosthesis may be manufactured based on the custom template object.

As will be described in further detail to follow, the example embodiments described herein also enable a new feature of templating plain radiographs. Namely, the embodiments described herein describe a determination of a plurality of different heights corresponding to different objects of interest contained within a radiograph. Based on the multiple heights, object rotation may be accurately determined and, as a result, a template may be rotated into an orientation that matches the rotation of the object or objects of interest. Thus, the embodiments described herein allow for selecting a template object substantially matching the shape of the object or objects of interest and improving the accuracy of measurement of the object of interest.

Alternatively, the example embodiments described herein may be used without templating or digital templating processes. For example, the example embodiments may be used in meniscal transplant surgery to determine the size of a replacement allograft. Similarly, the example embodiments may be used to, for example, determine the actual physical size of a tumor or growth.

In another example, a bone, bone feature, bone fracture, and/or soft tissue may be monitored or observed over time. For example, the object of interest may be a bone fracture. The bone fracture may be monitored over time in order to determine whether the fracture is healing properly. Multiple radiographs of the bone fracture may be captured over time, for example, every week, every two weeks, every month, or some other period of time. During each instance of capturing the radiographs, at least two images of the object of interest may be captured according to the example embodiments described herein in order to determine the magnification of the object of interest in at least one of the radiographs. The level of magnification in each of the multiple radiographs captured over time may be different due to, for example, variations in the positioning of the patient on the radiographic apparatus or due to changes in body composition of the patient.

When the level of magnification is not determined and accounted for in accordance with the example embodiments described herein, the radiographs may be incorrectly interpreted. For example, immediately after setting the fracture (placing and/or anchoring a broken (fractured) bone into the correct position for healing), an initial radiograph may be taken in order to ensure the bone is properly set (reduced) for healing. The image of the bone fracture may be magnified by a first level of magnification. Subsequently, for example, a week later, a follow-up radiograph may be captured of the bone fracture in order to ensure that the bone fracture is properly healing. The image of the bone fracture may be magnified by a second level of magnification. The second level of magnification may be different due to, for example, patient positioning on the radiography apparatus. If the second magnification is different from the first magnification, the change in magnification may create an appearance that the gap between the bones at the fracture site has become larger, that bone overlap at the fracture site has increased, or that the bone angular alignment has changed in the follow-up radiograph compared to the initial radiograph. This may incorrectly indicate or be interpreted as indicating that the fracture is not healing or is healing in an undesirable position. In fact, the fracture may be properly healing and may only appear to be changing due to the level of magnification of the fracture in the follow-up radiograph being different from the level of magnification of the fracture in the initial radiograph.

In contrast, when the initial and follow-up radiographs are acquired and processed according to the example embodiments described herein, this problem may be reduced or eliminated. Determining the level of magnification corresponding to each object of interest in each radiograph may allow the images of the object of interest contained in these radiographs to be scaled to accurately represent the actual physical size of the objects of interest. For example, two initial radiographs of the bone fracture may be taken in order to determine the magnification of the image of the bone fracture in at least one of the two initial radiographs, according to the example embodiments described herein. The image of the bone fracture contained in at least one of the two initial radiographs may be scaled according to the determined magnification in order to accurately represent the actual physical size of the bone fracture. This process may be repeated for the follow-up radiograph. The initial and follow-up radiograph may be accurately compared in order to determine whether the bone fracture is properly healing. Accordingly, the effect of any variations in magnification across the multiple radiographs taken over time may be reduced or eliminated.

Furthermore, the example embodiments described herein may be performed before, during, and/or after surgery. Additionally, the embodiments are not limited to use with humans and may be used, for example, in veterinary medical procedures. Yet further, the example embodiments described herein may be used outside of the medical field in order to accurately determine the respective sizes of objects of interest, as described herein.

IV. RADIOGRAPHIC DEVICES

FIG. 5A depicts an example arrangement of a radiation source 500 positioned above a radiation receiver 504. The object of interest 502 is shown positioned between the radiation source 500 and receiver 504. A radiograph 510 of the object of interest is shown in the top view 508 of receiver 504. The object 502 may be a part of a human body, such as the head of a femur or the head of a humerus. In general, the object 502 may be any physical structure not limited to bones or parts of the human body. The receiver 504 may be any type of film, material, or device that, when exposed to radiation 506 from source 500, results in the creation of an image 510 of object 502. The receiver 504 may also be referred to as a cassette or detector.

The diameter of image 510 is larger than the diameter of object 502. In other words, the image 510 is a magnified (enlarged) representation of the object 502. The embodiments described herein are directed at determining the level of magnification of the image 510 of object 502 so that the image 510 can be used to accurately represent the actual physical size of object 502.

FIG. 5B illustrates an example coordinate system 512 attached to receiver 504. The coordinate system 512 is a Cartesian coordinate system comprising an x-axis corresponding to a width of image 510, a y-axis corresponding to a length of image 510, and a z-axis corresponding to a height of objects (e.g., object 502) above the receiver 504. Some embodiments may alternatively utilize a polar coordinate system, a cylindrical coordinate system, a spherical coordinate system, or any combination thereof. Other choices of coordinate systems are possible. Some embodiments may chose a coordinate system that simplifies the computation required to determine the magnification of image 510.

In general, the embodiments described herein involve knowing, measuring, and/or determining the relative position between the radiation source 500 and the receiver 504, the object 502 and the receiver 504, the radiation source 500 and the object 502, and/or the image 510 and the receiver 504. Radiographic imaging systems may be automated such that the relative position between the source 500 and receiver 504 may be known based on position feedback mechanisms. For example, the radiographic system may be programmed, based on the body part of interest, to automatically move into a particular position, acquire a first image, move to a second position, and acquire a second image, and so on. Moving to a particular position may comprise movement of the radiation source 500, the receiver 504, or a combination of both. Alternatively or additionally, a holder or housing containing the radiation receiver 504 may be moved. For example, the holder or housing may be a radiography table on which a patient or a body part of the patient is disposed. Moving to the particular position may involve moving the radiography table along with the patient or body part of the patient without changing the relative position between the patient or the body part of the patient and the radiography table. Other variations may be possible.

The radiographic imaging system may associate corresponding spatial position data with each radiograph. For example, when the radiograph is captured, stored as a digital file, and/or represented on a display of a computing device, the spatial position data (based on an output of the position feedback mechanism) may be stored and/or represented as metadata associated with the digital file. The metadata may be a part of the digital radiograph image file or may be another file linked to the digital radiograph image file. Alternatively, the metadata may be included directly on a physical radiograph. The metadata may be printed in the corner of the radiograph such that it does not obstruct any of the images of anatomical features contained in the radiograph. The metadata may be retrieved automatically from a radiographic device by a computing device or may be provided to the computing device by a technician.

The spatial position data contained in the metadata may comprise 3D spatial position coordinates (e.g., (x,y,z) Cartesian coordinates, (θ,φ,r) polar coordinates) and angular orientation information of the radiation source 500 and the receiver 504. The spatial position data may include coordinates of the radiation source 500 in relation to (in a frame of reference attached to) the radiation receiver 504. Alternative embodiments may represent the spatial position data as coordinates of the radiation receiver 504 in relation to the radiation source 500. Some embodiments may alternatively represent the spatial position data as coordinates of the radiation source 500 and the radiation receiver 504 relative to an absolute reference frame. The radiograph and the associated spatial position data may subsequently be utilized by the embodiments described herein to determine the magnification, position, and spatial orientation of the object of interest.

In radiographic systems without automated position feedback, determination of the relative spatial position between the radiation source 500 and the receiver 504 may rely on a radiography technician. The radiographic system may include a light source projecting a reference light point onto a ruler located on a radiographic table housing the radiation receiver. The position of the radiation source 500 in relation to receiver 504 may be manually determined and recorded by the radiography technician. For example, using the reference light and the ruler, the radiation source 500 may first be centered above receiver 504, the relative vertical, horizontal, and angular positions may be recorded, and the first radiograph may be captured. The technician may subsequently change the angle of the radiation source 500 (using an inclinometer present and/or attached to the radiographic system) to a desired angle. The radiation source 500 may then be translated horizontally and vertically such that the reference light is again centered on the receiver 504. The technician may record the relative vertical, horizontal, and angular positions and may subsequently capture the second radiograph. Other procedures, both automated and manual, may be possible provided that the relative spatial position and orientation of the radiation source 500 and receiver 504 are known or may be measured or determined and provided that the spatial position and orientation information may be associated with the corresponding image.

V. DETERMINING OBJECT HEIGHT AND MAGNIFICATION

FIGS. 6A and 6B illustrate an example embodiment wherein the first image 610 and the second image 612 are captured at different distances between the radiation source 600 and the receiver 604. These and other figures are shown adjacent to each other to more clearly illustrate aspects of the embodiments. A vertical line is shown in these and other figures to clearly separate elements of the adjacent figures. In FIGS. 6A and 6B, the source 600 is assumed to be centered above the object 602. Additionally, the height (vertical distance) h of the object 602 above the receiver 604 as well as the diameter of the object a are assumed to be unchanged between when the two images are captured. Furthermore, object 602 is shown as a 2D cross-section of a sphere. However, alternative embodiments may model object 602 as different shapes (e.g., disk or cylinder) and may perform the corresponding calculations based on the particular shape of object 602.

In FIG. 6A, the radiation source 600 is located a distance $d_1$ above the receiver 604 at position 614. The radiation source 600 emits radiation 606 which creates an image 610, as illustrated in the top view 608A of receiver 604. The top view 608A may also represent the radiograph produced when object 602 is exposed to radiation 606 from radiation source 600 when radiation source 600 is at position 614. The image 610 has a measurable diameter $e_1$. After acquisition of image 610, the radiation source 600 may be moved from position 614 to position 616 as shown in FIG. 6B.

In FIG. 6B, the radiation source 600 is located a distance $d_2$ above the receiver 604 at position 616. The radiation source 600 emits radiation 606 which creates an image 612, as illustrated in the top view 608B of receiver 604. The top view 608B may also represent the radiograph produced when object 602 is exposed to radiation 606 from radiation source 600 when radiation source 600 is at position 616. The image 612 has a measurable diameter $e_2$. The image 612, produced when the radiation source is at position 616, has a greater degree of magnification than the image 610, produced when the source is at position 614. This is due to the position 616 being closer to receiver 604 than position 614. Accordingly, the diameter $e_2$ of image 612 is greater than the diameter $e_1$ of image 610. The order in which the images 610 and 612 are acquired is not important. For example, image 610 may be acquired after acquiring image 612 by moving the radiation source from position 616 to position 614. Similarly, the distances $d_1$ and $d_2$ can be varied provided that they are not equal.

It can be observed from FIGS. 6A and 6B that, due to magnification, the diameters of the images 610 and 612 ($e_1$ and $e_2$ respectively) are greater than the diameter a of the object of interest 602. The images 610 and 612 may be scaled by the corresponding level of magnification in order to accurately represent the actual physical size (diameter) a of object 602. The magnification $M_1$ of image 610 may be expressed by the ratio of the size of image $e_1$ to the actual physical size of the object a as in Equation (1). The magnification $M_2$ of image 612 can likewise be computed as Equation (2).

$$M_1 = e_1/a \quad (1)$$

$$M_2 = e_2/a \quad (2)$$

While $e_1$ and $e_2$ can be measured directly from the corresponding radiographs, the diameter a may be computed using trigonometric properties. Similarly, $d_1$ and $d_2$ may be obtained directly from the radiation source hardware or software. For example, a radiography system may utilize a position feedback mechanism to monitor the relative position between the radiation source 600 and receiver 604. Alternatively, the distances may be measured manually, using physical measuring devices, and may subsequently be provided to the software or hardware executing the embodiments described herein.

In general, the images 610 and 612 may be contained on two different radiographs or on a single radiograph acquired using a double exposure. For example, image 610 may be captured on a first radiographic film. Image 612 may subsequently be captured on a second radiographic film. Alternatively, both images 610 and 612 may be captured on the same film, potentially resulting in some overlap between the images 610 and 612. Similarly, representations of the images 610 and 612 and/or representations of the respective radiographs containing the images 610 and 612 may be displayed separately or as image overlays. For example, a representation of the radiograph containing image 610 may be overlaid on top of a display of a representation of the radiograph containing image 612.

Figure 6D:
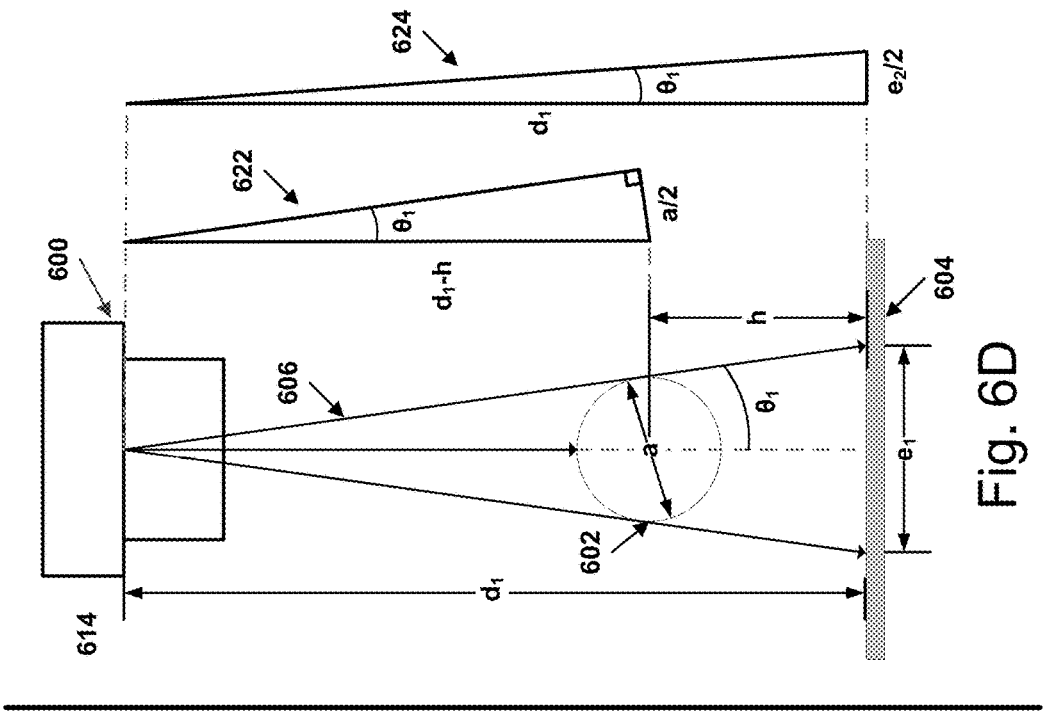
FIGS. 6C and 6D illustrate geometric models of FIGS. 6A and 6B, according to an example embodiment.
Figure 6C:
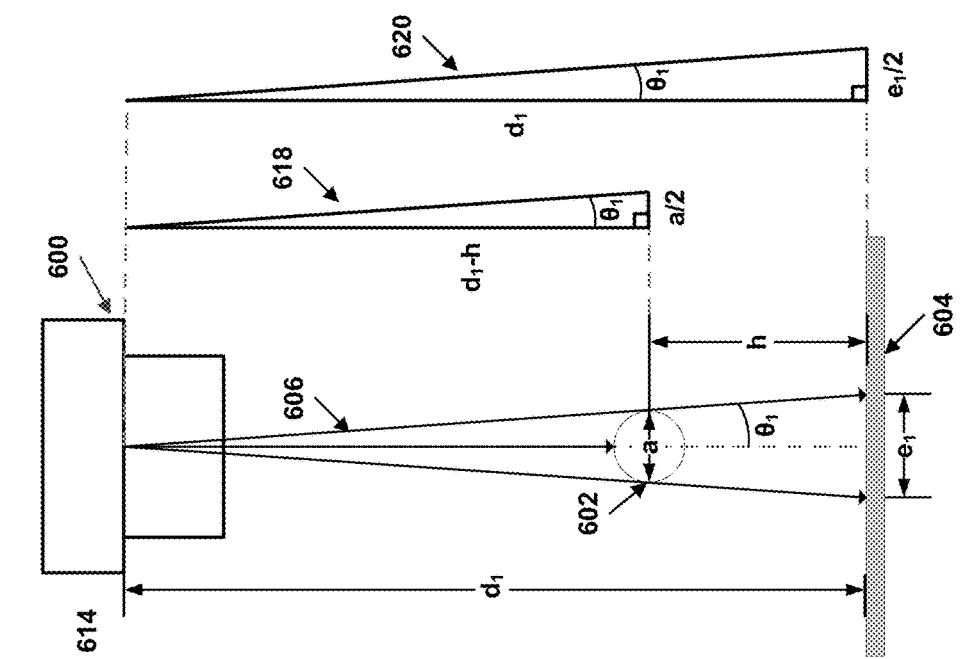

FIG. 6C shows an example way of modeling the geometry of the radiation source 600 located at position 614, the object 602, and the receiver 604. Specifically, based on triangles 618 and 620, the tangent of the angle $\theta_1$ may be expressed as Equations (3) and (4) respectively.

$$\tan(\theta_1) = \frac{a/2}{d_1 - h} \quad (3)$$

$$\tan(\theta_1) = \frac{e_1/2}{d_1} \quad (4)$$

Equations (3) and (4) may be combined into Equation (5) to solve for a.

$$\frac{a/2}{d_1 - h} = \frac{e_1/2}{d_1} \quad (5)$$
$$a = \frac{e_1(d_1 - h)}{d_1}$$

Plugging Equation (5) back into Equation (1) yields Equation (6).

$$M_1 = \frac{d_1}{d_1 - h} \quad (6)$$

An equivalent procedure may be carried out for the image 612 acquired with the radiation source at position 616. The size (diameter) a of object 602 may be expressed by Equation (7) and the magnification $M_2$ of the image 612 may be expressed by Equation (8).

$$a = \frac{e_2(d_2 - h)}{d_2} \quad (7)$$

$$M_2 = \frac{d_2}{d_2 - h} \quad (8)$$

In order to determine the magnification of either image 610 or 612, example embodiments may determine the height h of the object 602 by combining Equations (5) and (7), resulting in Equation (9).

$$\frac{e_1(d_1 - h)}{d_1} = \frac{e_2(d_2 - h)}{d_2} \quad (9)$$
$$e_1 d_2(d_1 - h) = e_2 d_1(d_2 - h)$$
$$h = \frac{d_1 d_2(e_2 - e_1)}{d_1 e_2 - d_2 e_1}$$

It may be apparent from Equation (9) that at least two images are needed in order to determine the height h of object 602. Additionally, in this particular embodiment, the images must be taken from two different heights. Namely, the distances $d_1$ and $d_2$ cannot be equal in order to obtain a non-trivial solution for h. The height h may now be used with Equations (6) and (8) to determine the magnifications $M_1$ and $M_2$. Either or both of images 610 and 612 may be scaled according to the corresponding level of magnification ($M_1$ and $M_2$ respectively) to determine and display the actual size a of the object of interest 602.

The determined actual size may be used to select a template closest in shape and size to the object of interest. For example, the object of interest may be a femur or the corresponding acetabulum (femoral socket). The templates may represent a plurality of available replacement femoral stem prosthesis and/or corresponding acetabular prostheses. Selecting a replacement prosthesis closest in size and shape to the actual anatomical size of a patient's femur and acetabulum prior to a hip replacement surgery may ensure that the replacement prosthesis will properly fit the patient's anatomy.

A computing device may be programmed or configured to carry out the operations and/or the embodiments described herein. For example, the computing device may obtain two radiographs or digital representations of the two radiographs (e.g., image files of the radiographs). A first radiograph may contain image 610. The first radiograph may be associated with first metadata indicating the distance $d_1$. Alternatively, the first metadata may contain the spatial coordinates of the radiation source 600 and radiation receiver 604. The distance $d_1$ may be determined from the spatial coordinates using arithmetic operations. Similarly, a second radiograph may contain image 612. Likewise, the second radiograph may be associated with a second metadata indicating, either directly or indirectly, the distance $d_2$.

The computing device may subsequently scan or search the first radiograph or digital representation thereof to locate the image 610. Similarly, the second radiograph or digital representation thereof may be scanned or searched to locate the image 612. For example, the computing device may be programmed to search for geometric shapes or features such as circles in order to identify the images 610 and 612. Alternatively, a user may identify the images 610 and 612 using a graphical user interface that the computing device is programmed or configured to implement. After locating images 610 and 612 in the respective radiographs, the diameters $e_1$ and $e_2$ of images 610 and 612, respectively, may be determined by, for example, counting the number of pixels along a line that defines the diameter of each circular image 610 and 612.

The computing device may use the determined values of $d_1$, $d_2$, $e_1$, and $e_2$ to implement Equations (1) to (9), as detailed above, in order to determine the magnifications $M_1$ and $M_2$ of images 610 and 612, respectively. The diameters $e_1$ and $e_2$ of images 610 and 612 may be modified according to the corresponding levels of magnification $M_1$ and $M_2$ to represent the actual physical size of object 602. The modification may comprise temporarily adjusting the visual display of the digital representations of images 610 and 612. Alternatively, the modification may comprise permanently storing the adjusted size of images 610 and 612 in a file containing the respective images and/or the corresponding metadata. Other variations are possible. The computing device may also be programmed or configured to perform or interface with a device configured to perform templating and/or digital templating as described with respect to FIGS. 2-4.

FIG. 6D illustrates an alternative way of modeling the geometry of the radiation source 600 located at position 614, the object 602, and the receiver 604. This alternative embodiment more accurately accounts for the spherical shape of the object of interest 602. The size (diameter) a of object 602 is exaggerated in FIG. 6D in order to more clearly point out the geometric basis for the following calculations. Specifically, a tangent to a circle is always perpendicular to the radius of the circle. Consequently, triangle 622 more accurately models the geometry of this particular embodiment (where object 602 is spherical) than triangle 618. Based on triangle 622, the sine of the angle $\theta_1$ may be expressed as in Equation (10).

$$\sin(\theta_1) = \frac{a/2}{d_1 - h} \quad (10)$$

Likewise, Equation (11) may be written based on triangle 624.

$$\tan(\theta_1) = \frac{e_1/2}{d_1} \quad (11)$$

However, the calculations presented with respect to FIG. 6C are accurate for spherical object 602 when the angle $\theta_1$ is small since $\sin(\theta_1) \approx \tan(\theta_1)$ for small $\theta_1$.

Example embodiments may utilize either the geometric model of FIG. 6C or 6D provided that the assumptions behind the utilized model are taken into consideration. For example, Equation (3), based on the model of FIG. 6C, is accurate when $\theta_1$ is small enough such that $\sin(\theta_1) \approx \tan(\theta_1)$. Under such conditions, both Equations (3) and (10) may produce accurate results that can reliably be used in subsequent calculations. When the assumption of small $\theta_1$ is no longer true, then Equation (10) may be used because using Equation (3) may lead to inaccurate calculation results. Accordingly, either model may be used provided that the assumptions of the model hold true under the specific use conditions.

The distances $e_1$ and $d_1$, illustrated in FIG. 6D, are known or may be measured directly. Consequently, the angle $\theta_1$ can be expressed by Equation (12).

$$\theta_1 = \tan^{-1}\left(\frac{e_1/2}{d_1}\right) \quad (12)$$

A second image may be taken at a distance $d_2$, producing an image with diameter $e_2$ in a manner similar to that described with respect to FIGS. 6A and 6B. The angle $\theta_2$ may be analogously modeled according to Equations (13), (14), and (15).

$$\sin(\theta_2) = \frac{a/2}{d_2 - h} \quad (13)$$

$$\tan(\theta_2) = \frac{e_2/2}{d_2} \quad (14)$$

$$\theta_2 = \tan^{-1}\left(\frac{e_2/2}{d_2}\right) \quad (15)$$

Based on the first image, the size a of object 602 may be expressed by Equation (16), derived from Equation (10).

$$a = 2(\sin(\theta_1))(d_1 - h) \quad (16)$$

Based on the second image, the size a of the object 602 may be expressed by Equation (17), derived from Equation (13).

$$a = 2(\sin(\theta_2))(d_2 - h) \quad (17)$$

Equations (16) and (17) may be combined and solved for h as shown by Equation (18), where $\theta_1$ and $\theta_2$ are given by Equations (12) and (15), respectively.

$$2(\sin(\theta_1))(d_1 - h) = 2(\sin(\theta_2))(d_2 - h) \quad (18)$$

$$h = \frac{d_2 \sin(\theta_2) - d_1 \sin(\theta_1)}{\sin(\theta_2) - \sin(\theta_1)}$$

The height expressed by Equation (18) may now be used to compute the levels of magnification expressed by Equations (6) and (8). The computed magnifications $M_1$ and $M_2$ may be used to appropriately scale at least one of the corresponding image 610 and 612, as described with respect to FIGS. 6A and 6B. The scaled image may be used to determine a template (representing a replacement part for the object of interest 602) closest in shape and size to the object of interest 602.

As with FIG. 6C, a computing device may be programmed or configured to implement the operations described with respect to FIG. 6D. For example, the computing device may obtain, acquire, or capture two radiographs or digital representations thereof. A first radiograph may contain image 610 and be associated with metadata indicating or used to determine the distance $d_1$. Likewise, a second radiograph may contain image 612 and be associated with metadata indicating or used to determine the distance $d_2$. The computing device may be programmed to determine the distances $e_1$ and $e_2$ using image recognition and/or feature detection algorithms. The computing device may also be programmed to implement Equations (6), (8), and (10) to (18), as detailed above, in order to determine the magnifications $M_1$ and $M_2$ or images 610 and 612, respectively. The images 610 and 612 may be scaled according to magnifications $M_1$ and $M_2$ and may be used in templating and/or digital templating, as described with respect to FIGS. 2-4.

In general, although the distances $e_1$ and $e_2$ used to determine the corresponding level of magnification may be, in some embodiments, diameters of the object of interest, the distances $e_1$ and $e_2$ may alternatively be measured in a different manner. For example, the distances $e_1$ and $e_2$ may be distances of a particular object of interest or feature thereof measured in relation to a reference point (anchor point) in a radiograph, as described in detail with respect to the embodiments depicted in FIGS. 14C-14E.

FIGS. 7A and 7B illustrate an alternative embodiment wherein the second image 712 is captured while the vertical and horizontal positions of the radiation source 700 are different from the vertical and horizontal positions of the radiation source 700 used to capture the first image 710. FIG. 7B additionally shows the radiation source 700 rotated relative to its original position in FIG. 7A. The radiation source 700 may be rotated in order to ensure that the emitted radiation 706, or at least a portion thereof, is aimed at the object of interest 702. However, the radiation source 700 may also be rotated in order to take a second image 712 from a different perspective than image 710. While FIG. 7B shows the radiation source 700 in a rotated position relative to the position illustrated in FIG. 7A, alternative embodiments may be practiced without rotating the radiation source 700.

In general, although FIG. 7B illustrates the radiation source 700 translated vertically, translated horizontally, and rotated relative to the position 714 in FIG. 7A, alternative embodiments may function by performing only one of the described movements. For example, some embodiments may involve only horizontal translation of the radiation source 700 or both horizontal translation and rotation of the radiation source 700. In alternative embodiments, the radiation receiver 704 may be moved while the radiation source 700 is held in a fixed position. The embodiment illustrated by FIGS. 7A and 7B includes all three movement types (horizontal translation, vertical translation, and rotation) for the purpose of providing a generalized example geometric model.

Furthermore, although the example diagrams are two-dimensional, the embodiments described herein are equally applicable to three dimensions. For example, a different perspective of the object of interest may be achieved via horizontal translation in the x-direction, horizontal translation in the y-direction, vertical translation in the z-direction, rotation along the pitch-axis, rotation along the roll-axis, or any combination thereof, provided that the geometry of the changed perspective is properly accounted for, as demonstrated herein.

FIG. 7A illustrates radiation source 700 located a distance $d_1$ above the receiver 704. The radiation source 700 emits radiation 706, which creates an image 710, as illustrated in the top view 708A of receiver 704. The top view 708A may also represent the radiograph produced when object 702 is exposed to radiation 706 from radiation source 700 when radiation source 700 is at position 714. The image 710 has a diameter $e_1$. Line 720 illustrates the x-position of the radiation source 700 above receiver 704. After acquisition of image 710, the radiation source 700 may be moved from position 714 to position 716 as shown in FIG. 7B. In FIG. 7B, the radiation source 700 is located a distance $d_2$ above the receiver 704 at position 716. Additionally, the radiation source 700 has been translated horizontally to the left as indicated by arrow 718. The difference in x-position of line 720 and line 722 illustrates the extent of horizontal translation.

In FIG. 7B, radiation source 700 emits radiation 706 which creates an image 712, as illustrated in the top view 708B of receiver 704. The top view 708B may also represent the radiograph produced when object 702 is exposed to radiation 706 from radiation source 700 when radiation source 700 is at position 716. The image 712 has a diameter $e_2$. The image 712 produced by the radiation source at position 716 has a greater degree of magnification than the image 710 produced when the source is at position 714. This is due to position 716 being vertically closer to receiver 704 than position 714. Accordingly, the diameter $e_2$ of image 712 is greater than the diameter $e_1$ of image 710. Additionally, as the source is translated to the left from position 714 to position 716, the projected image 712 translates to the right of the position of projected image 710.

As with the embodiment of FIGS. 6A and 6B, the order in which the images 710 and 712 are acquired is not important. For example, image 710 may be acquired after acquiring image 712 by moving the radiation source from position 716 to position 714. Similarly, the distances $d_1$ and $d_2$ may be varied provided that they are known (through automated methods or explicit measurements) and enable the acquisition of images of sufficient quality for analysis. The distances $d_1$ and $d_2$ may be equal in some embodiments.

In some embodiments, the resulting images of the object of interest may be elongated due to the geometric relationship of the radiation source, the object of interest, and the receiver. For example, the example embodiment illustrated by FIG. 7B may result in the spherical object 702 producing an elliptical image (not depicted) as opposed to the circular image 712. Specifically, the extent of image elongation will depend on the degree of rotation of the radiation source 700, the difference in horizontal (lateral) position between the object of interest 702 and the radiation source 700, and the size (diameter) a of the object 702. For example, the embodiment illustrated in FIGS. 6A and 6B produces no elongation because the object of interest 602 is positioned directly beneath the radiation source 600.

The example embodiments described herein may be operated in a manner that does not result in a significant degree of image elongation. For example, in FIG. 7B, the difference in x-position between lines 720 and 722, corresponding to the horizontal translation of radiation source 700 from position 714 to position 716, may be kept small such that the extent of image elongation may be ignored without compromising the mathematical accuracy of subsequent computations. Alternative embodiments may remove, adjust, and/or account for any elongation present in the images using software algorithms or specialized hardware performing similar functions. Removal or adjustment of elongation may be based on any known or calculated quantities pertaining to the geometric relationship between the radiation source, the object of interest, and the receiver. In some embodiments, elongation may be removed regardless of the extent of elongation present in the image. Alternative embodiments may remove or account for elongation only when it is determined that the extent of elongation present in a particular image is above a threshold value. Example methods of accounting for image elongation are illustrated in and described in detail with respect to FIG. 7E.

Similar to FIGS. 6A and 6B, it can be observed from FIGS. 7A and 7B that due to magnification, the sizes (diameters) of the images 710 and 712 ($e_1$ and $e_2$ respectively) are greater than the size (diameter) a of the object of interest 702. In order to accurately represent the actual physical size (diameter) a of object 702, the images 710 and 712 may be scaled by the corresponding level of magnification. When the extent of image elongation is small (alternatively, when image elongation is removed altogether using software algorithms), the magnification $M_1$ of image 710 may be expressed according to Equations (1) and (6). Likewise, the magnification $M_2$ of image 712 can be expressed according to Equations (2) and (8).

Figure 7C:
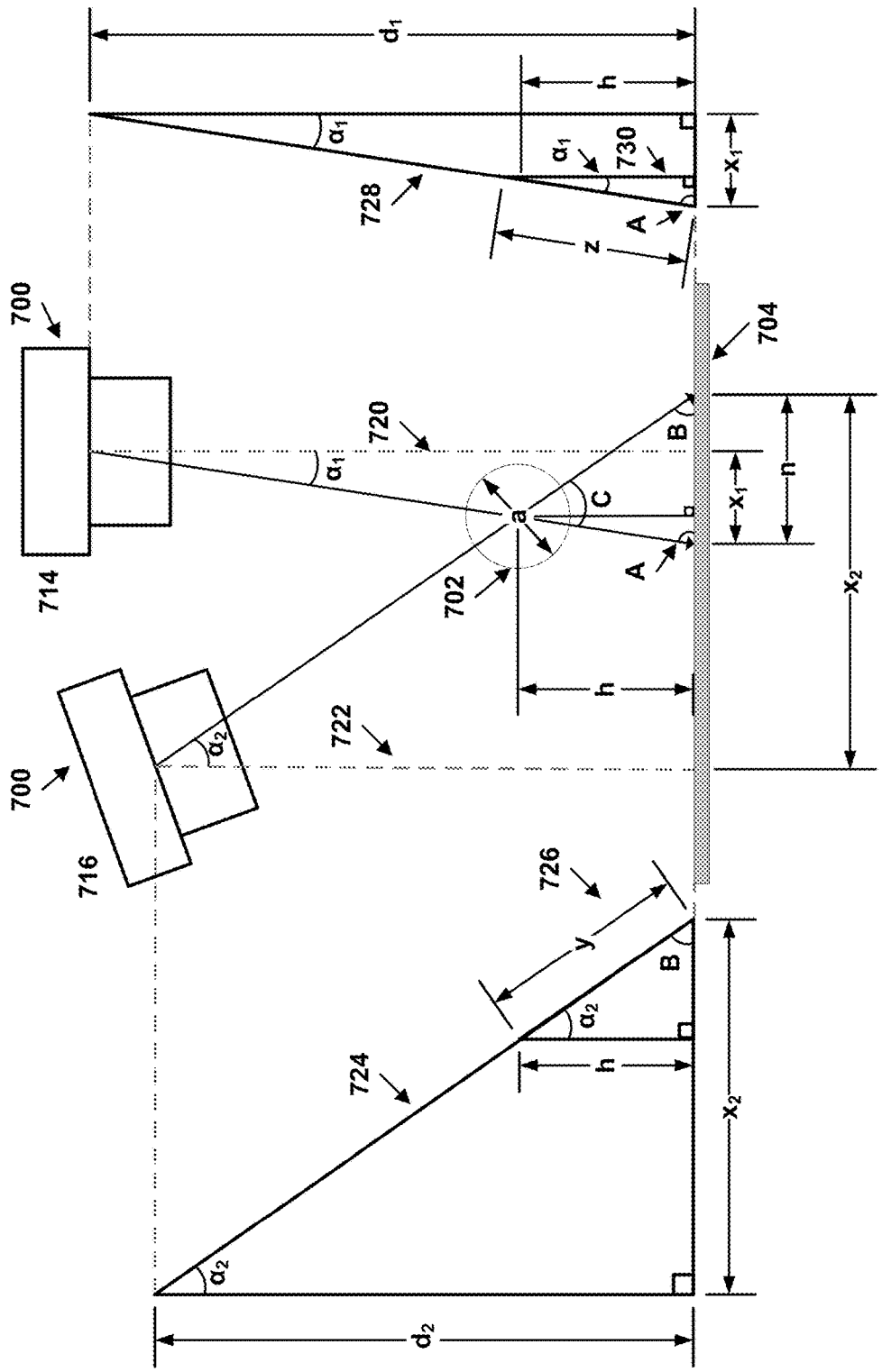
FIGS. 7C and 7D illustrate geometric models of FIGS. 7A and 7B, according to an example embodiment.

FIG. 7C shows an example way of modeling the geometry of the embodiment illustrated in FIGS. 7A and 7B. The size (diameter) a of object 702 is exaggerated to more clearly illustrate the relevant geometry. As with the embodiment illustrated in FIGS. 6A and 6B, the present embodiment determines the level of magnification of images 710 and 712 to scale at least one of the images by the corresponding level of magnification in order to determine the actual size (diameter) a of object 702.

The length $x_2$ is the horizontal distance (difference in the x-coordinate of position) between the radiation source 700 at position 716 and the center of the corresponding image (the image 712 taken from position 716). The length $x_1$ represents an analogous relationship between the radiation source 700 at position 714 and the corresponding image 710. The horizontal positions 720 and 722 corresponding to radiation source 700 locations 714 and 716, respectively, may be determined from position feedback mechanisms of the radiography system or may alternatively be determined by a radiography technician. The centers of images 710 and 712 may be determined manually, based on user input, or automatically in software using image processing algorithms. For example, when images 710 and 712 are or are expected to be circles or approximately circular, the centers may be found using, for example, the Hough Circle Transform. The centers of images 710 and 712 may also be determined by any of the methods described later with respect to FIG. 7E. The distances $x_1$ and $x_2$ may be determined manually, via user input, or automatically, by a computing device executing specialized software, based on the parameters described above.

In embodiments that acquire images with minimal or no elongation, the x-coordinate of the image corresponding to the center of the object of interest may be the center of the produced image. For example, in the present embodiment, the object 702 is spherical and produces circular images 710 and 712. The x-coordinates of images 710 and 712 corresponding to the center of object 702 are the x-coordinates of the midpoints (centers) of the respective images. Objects of interest may have different shapes and may be modeled according to the methods described herein by accounting for the geometric shape of the object of interest in the relevant calculations. Alternative embodiments may acquire images having a non-negligible amount of elongation. The point in the image corresponding to the center of the object of interest may be determined by accounting for the amount of image elongation as illustrated in and described in detail below with respect to FIG. 7E.

In the case of a fully automated radiography system, the position (x, y, and z) of the radiation source 700 can be determined in relation to receiver 704 and images 710 and/or 712 based on position feedback associated with radiation source 700 and receiver 704. Alternative embodiments may function with a system without automated position feedback. Specifically, a technician operating the radiation source 700 may keep track of the position of radiation source 700 and may subsequently input the information into hardware or software to associate the coordinates of the radiation source 700 at position 716 with image 712. Example embodiments may determine the position of the center of the image 712 using software or specialized hardware. Alternatively, the position of the center of image 712 may be determined manually by a technician. The determined position may subsequently be entered into computing software or hardware. Automation of the methods described herein may result in more accurate measurements and computation.

Based on triangle 724 of FIG. 7C, the tangent of the angle B may be expressed by Equation (19), where the distance $d_2$ is the height of radiation source 700 above receiver 704 at position 716.

$$\tan(B) = \frac{d_2}{x_2} \tag{19}$$

Accordingly, angle B may be determined according to Equation (20).

$$B = \tan^{-1}\left(\frac{d_2}{x_2}\right) \tag{20}$$

Similarly, based on triangle 724, the angle $\alpha_2$ may be computed according to Equation (21).

$$\alpha_2 = 90° - B \tag{21}$$

Based on triangle 728 of FIG. 7C, the tangent of angle A may be computed according to Equation (22) where the distance $d_1$ is the height of radiation source 700 above receiver 704 at position 714.

$$\tan(A) = \frac{d_1}{x_1} \tag{22}$$

Accordingly, angle A may be determined according to Equation (23).

$$A = \tan^{-1}\left(\frac{d_1}{x_1}\right) \tag{23}$$

Similarly, based on triangle 728, the angle $\alpha_1$ may be computed according to Equation (24).

$$\alpha_2 = 90° - A \tag{24}$$

Based on triangle 726, of FIG. 7C, the height h of the object of interest 702 may be expressed according to Equation (25).

$$h = (y)\sin(B) \tag{25}$$

Likewise, based on triangle 730, the height of h of the object of interest 702 may be expressed according to Equation (26).

$$h = (z)\sin(A) \tag{26}$$

Figure 7D:
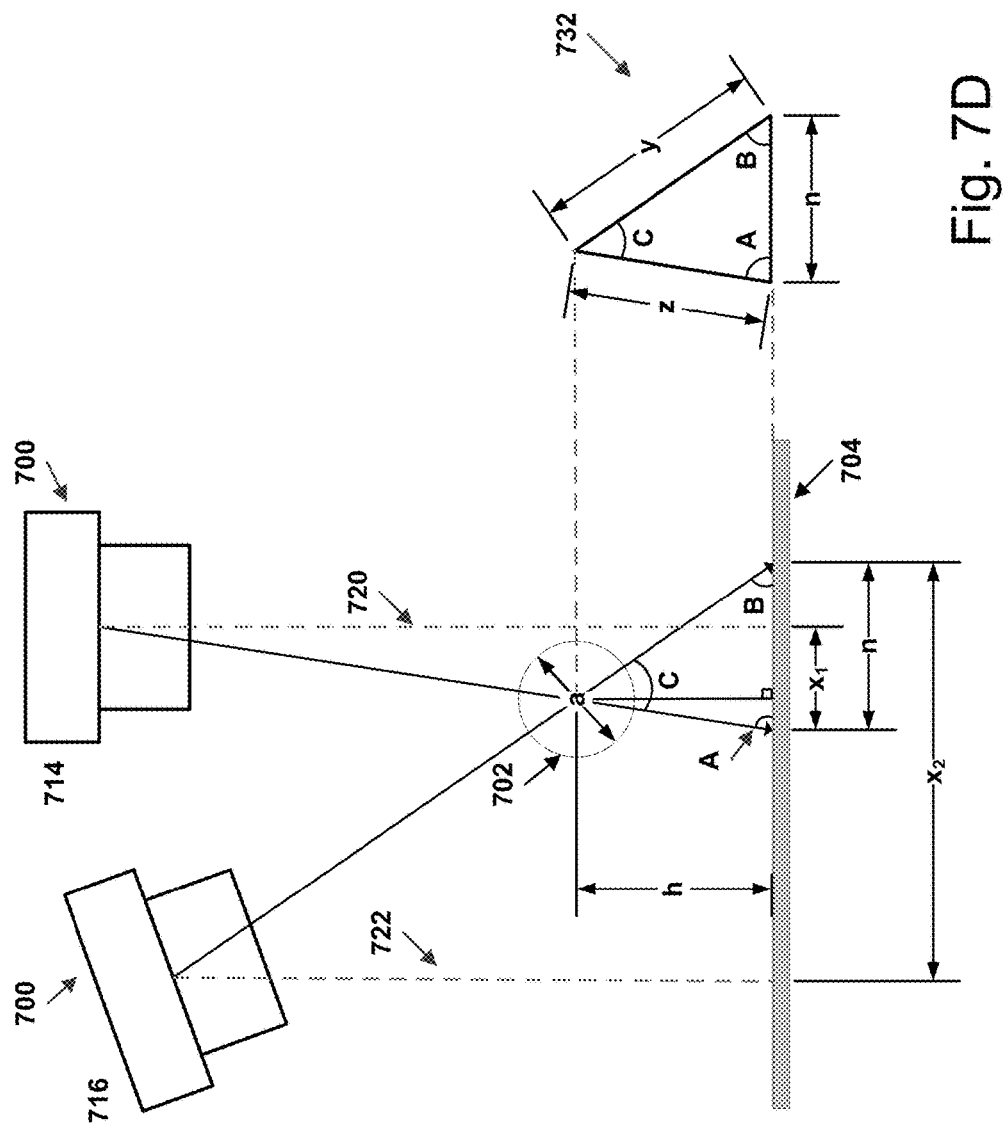

Based on triangle 732 shown in FIG. 7D, hypotenuse y of triangle 726 and hypotenuse z of triangle 730 may be determined using the law of sines according to Equation (27), where n is the distance between the center of image 710 and image 712.

$$\frac{\sin(A)}{y} = \frac{\sin(B)}{z} = \frac{\sin(C)}{n} \tag{27}$$

The distance n is a measurable quantity that may be determined directly from the radiographs using software and/or hardware image processing methods. Alternatively, n may be determined using the methods described with respect to FIG. 7E.

Based on FIG. 7C, the angle C may be determined according to Equation (28).

$$C = \alpha_1 + \alpha_2 \tag{28}$$

Accordingly, by combining Equations (20) or (28) with Equation (27), hypotenuse y may be expressed according to Equation (29).

$$y = \frac{(n)\sin(A)}{\sin(C)} \tag{29}$$

Analogously, by combining Equations (23) or (28) with Equation (27), hypotenuse z may be expressed according to Equation (30).

$$z = \frac{(n)\sin(B)}{\sin(C)} \quad (30)$$

Finally, by combining Equations (25) and (29) or Equations (26) and (30), the height h of the object of interest 702 may be determined according to Equation (31).

$$h = \frac{(n)\sin(A)\sin(B)}{\sin(C)} \quad (31)$$

With the height h known, the magnification can be computed for image 710 and/or image 712 according to Equations (6) and (8), respectively. The images may be scaled according to the corresponding level of magnification in order to determine and display the actual physical size (diameter) a of the object of interest 702.

Figure 7E:
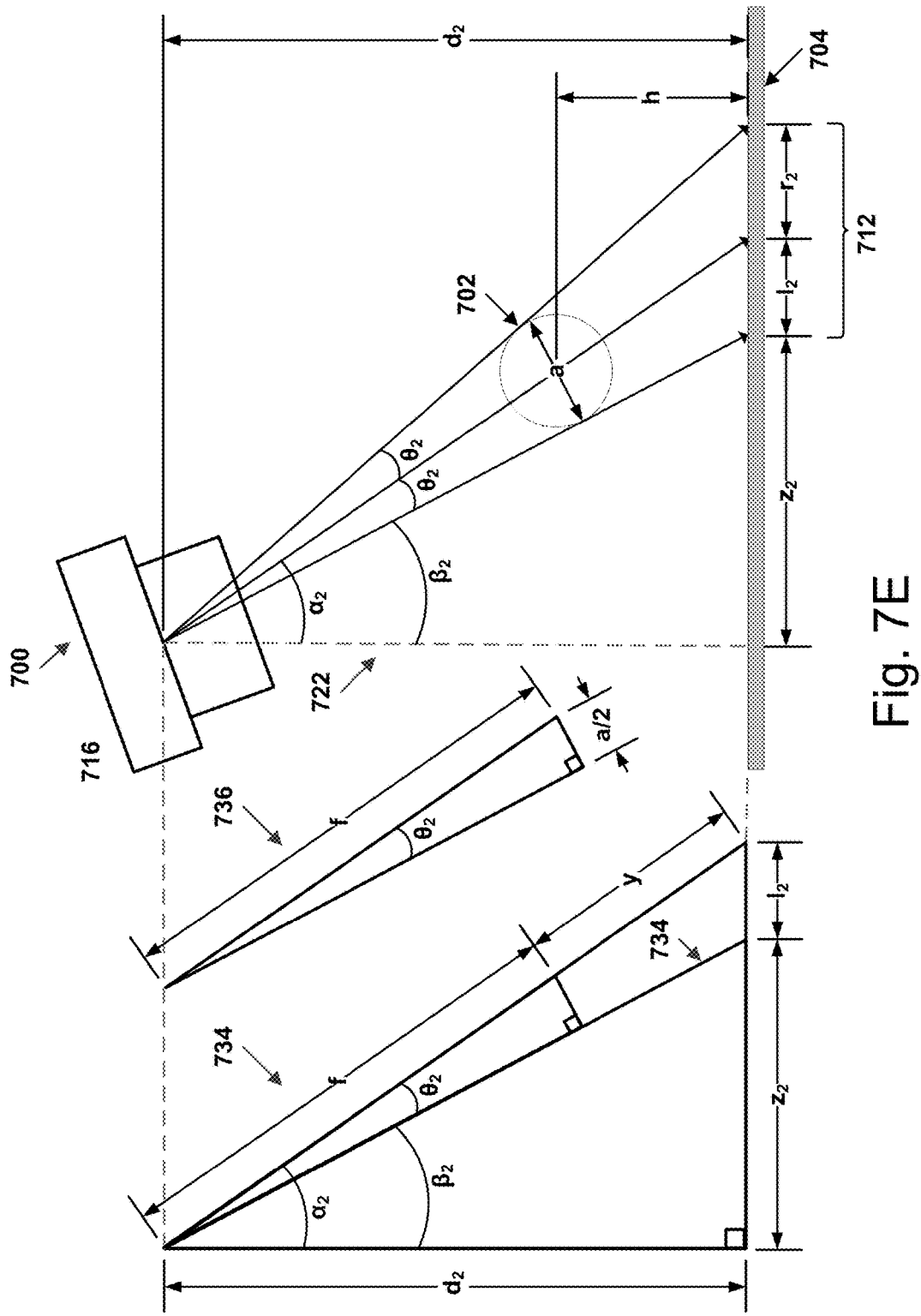
FIG. 7E illustrates a geometric model of FIG. 7B accounting for image elongation, according to an example embodiment.

As previously mentioned, alternative embodiments may determine the magnification of the object of interest 702 by considering the extent of image elongation. FIG. 7E illustrates another example geometric model of the embodiment described with respect to FIGS. 7A and 7B. The magnification $M_2$ of the image 712 produced when the radiation source 700 is at position 716 can be expressed according to Equation (32). The size $l_2+r_2$ of the image 712, labeled as $e_2$ in FIG. 7B, may be determined directly from the radiograph containing image 712. Based on triangle 736, the size a of the object 702 may be expressed according to Equation (33).

$$M_2 = \frac{l_2 + r_2}{a} \quad (32)$$

$$a = 2f\sin(\theta_2) \quad (33)$$

The distance $l_2$, corresponding to the left image portion of image 712, and the distance $r_2$, corresponding to the right image portion of image 712, may be determined explicitly in order to accurately locate the point in the image 712 corresponding to the center of object 702. Specifically, based on triangle 734, the angle $\beta_2$ may be derived from Equation (34) and expressed according to Equation (35), where $z_2$ is a known, measurable quantity corresponding to the distance between the x-coordinate of position 716 (represented by line 722) and the left edge of image 712.

$$\tan(\beta_2) = \frac{z_2}{d_2} \quad (34)$$

$$\beta_2 = \tan^{-1}\left(\frac{z_2}{d_2}\right) \quad (35)$$

Similarly, the sum $z_2+l_2+r_2$ is a known, measurable quantity corresponding to the distance between the x-coordinate of position 716 and the right edge of image 712. Furthermore, the distance $z_2+l_2$ corresponds to the distance $x_2$ from FIGS. 7C and 7D.

The angle $\theta_2$ may be derived, based on triangle 734, using Equation (36) and may be expressed according to Equation (37).

$$\tan(\beta_2 + 2\theta_2) = \frac{z_2 + l_2 + r_2}{d_2} \quad (36)$$

$$\theta_2 = \frac{1}{2}\tan^{-1}\left(\frac{z_2 + l_2 + r_2}{d_2}\right) - \frac{\beta_2}{2} \quad (37)$$

With angle $\theta_2$ and $\beta_2$ known, the distance $l_2$ may be derived based on Equation (38) and expressed according to Equation (39).

$$\tan(\beta_2 + \theta_2) = \frac{z_2 + l_2}{d_2} \quad (38)$$

$$l_2 = d_2\tan(\beta_2 + \theta_2) - z_2 \quad (39)$$

The distance $r_2$ may likewise be expressed according to Equation (40). Alternatively, since the sum $z_2+l_2+r_2$ is known, $r_2$ may be determined arithmetically.

$$r_2 = d_2\tan(\beta_2 + 2\theta_2) - z_2 - l_2 \quad (40)$$

The angle $\alpha_2$, as shown in FIGS. 7C and 7E, may be expressed according to Equation (41).

$$\alpha_2 = \beta_2 + \theta_2 \quad (41)$$

This method of determining the angle $\alpha_2$ may be used in combination with or in place of any of the methods described with respect to FIGS. 7C and 7D.

The length f may be derived based on triangle 734 using Equation (42), where y is determined according to Equation (29).

$$\cos(\alpha_2) = \frac{d_2}{f + y} \quad (42)$$

The length f may be expressed according to Equation (43).

$$f = \frac{d_2}{\cos(\alpha_2)} - y \quad (43)$$

Consequently, the size a of object 702 may be expressed according to Equation (44) by combining Equations (33), (37), and (43).

$$a = \left(\frac{2d_2}{\cos(\alpha_2)} - y\right)\sin\left(\alpha_2 - \tan^{-1}\left(\frac{z_2}{d_2}\right)\right) \quad (44)$$

At this point, the size a may be computed numerically based on the known or measurable quantities, according to Equation (44). The size a may be used to compute the magnification $M_2$ according to Equation (32). Alternatively or additionally, some embodiments may determine the level of magnification for each half of the object of interest. Specifically, magnification of the left side $M_{2l}$ of image 712 may be expressed as according to Equation (45).

$$M_{2l} = \frac{l_2}{a/2} \quad (45)$$

Likewise, the magnification of the right side $M_{2r}$ of image 712 may be expressed according to Equation (46).

$$M_{2r} = \frac{r_2}{a/2} \quad (46)$$

The magnification $M_2$ may be used to scale the image 712 in order to accurately and proportionately represent the actual physical size a of object 702. Alternatively or additionally, the magnification $M_{2l}$ may be used to scale the left side of image 712, having length $l_2$, and the magnification $M_{2r}$ may be used to scale the right side of image 712, having length $r_2$, in order to more accurately account for any elongation of image 712. The above procedure may also or instead be carried out for image 710 corresponding to radiation source 700 at position 714.

FIGS. 8A and 8B illustrate yet another example embodiment for determining 3D information based on at least two 2D images acquired from different perspectives. FIG. 8A illustrates radiation source 800 positioned above receiver 804 at position 814. The radiation source 800 emits radiation 806, producing an image 810 of object 802 shown in the top view 808A of receiver 804. An x-y coordinate frame attached to the top view 808A indicates the spatial relationship between the receive 804 and the object 802 at the moment that image 810 was captured. The image 810 has a diameter $e_1$.

The radiation source is subsequently translated and rotated 90 degrees counterclockwise from position 814 to position 816, as indicated by arrow 820 in FIG. 8B. Similarly, the receiver 804 is rotated 90 degrees clockwise, as indicated by arrow 818, in order to receive the radiation 806 from the rotated radiation source 800. The radiation 806 in FIG. 8B is now directed perpendicular to the radiation 806 in FIG. 8A.

The bottom of the receiver 804 is positioned at the same height (along the z-axis) in both FIG. 8A and FIG. 8B. Namely, the receiver 804 is rotated, but not translated, between FIGS. 8A and 8B. A y-z coordinate frame attached to the top view 808B indicates the spatial relationship between the receiver 804 and the object 802 at the moment that image 812 was captured. The object 802 remains in the same position and at the same height h in both FIGS. 8A and 8B. Accordingly, the height of the center of the object of interest h is equal to the height of the center of projected image 812. This holds true when the radiation source 800 at position 816 is at approximately the same height h as object 802. The case when radiation source 800 and object 802 are not aligned at the same height h is discussed below. The height h can be determined explicitly based on image 812 using a computing device. The computing device may execute program instructions that cause the computing device to determine the center of image 812 and determine the distance between the center of image 812 and the bottom (along the z-axis) of the radiograph containing image 812.

The height h may be used to determine the magnification $M_1$ of image 810 according to Equation (6). The image 810 may be scaled according to the determined magnification $M_1$ so as to accurately represent the actual, physical size of object 802. Although FIGS. 8A and 8B depict the radiation source 800 centered with the object 802, alternative embodiments may function when the radiation source 800 and object 802 are not centered or aligned. When radiation source 800 and object 802 are not aligned and centered, embodiments may determine the height h of object 802 by accounting for the exact geometric relationship between the object 802, the radiation source 800, and receiver 804. Accounting for the exact geometric relationship may comprise calculations similar to those presented with respect for FIGS. 7A-7E. Additionally, any resulting image elongation may be accounted for or corrected using any of the embodiments described with respect to FIGS. 7A-7E. In some embodiments, the impact of any misalignment between object 802 and radiation source 800 may be negligible and may be ignored.

VI. DETERMINING OBJECT SPATIAL ORIENTATION

Figure 9B:
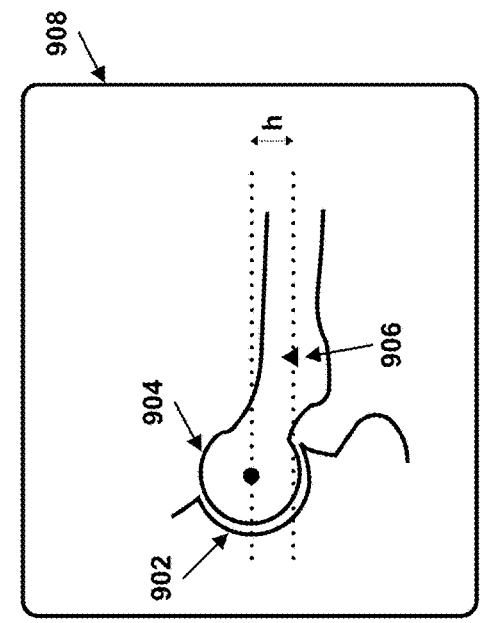
FIG. 9B illustrates a lateral radiograph of the human hip, according to an example embodiment.
Figure 9D:
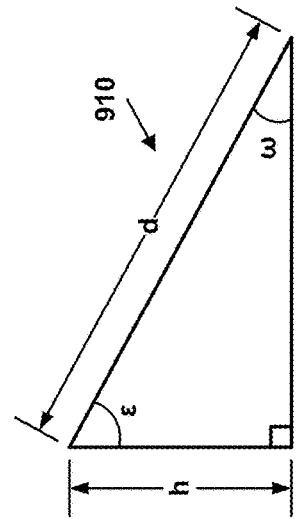
FIG. 9D illustrates a geometric model of the rotated human hip, according to an example embodiment.
Figure 9A:
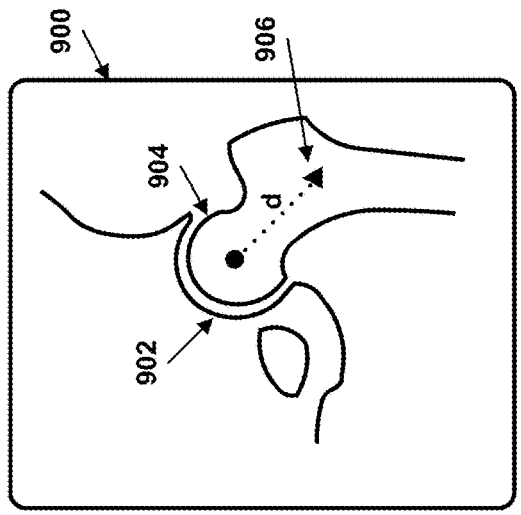
FIG. 9A illustrates an anteroposterior radiograph of a human hip, according to an example embodiment.

FIGS. 9A-9D illustrate an example embodiment enabling the determination of the orientation of an object of interest. Specifically, FIG. 9A illustrates an AP radiograph 900 of a human hip. The hip radiograph comprises images of acetabulum 902, femoral head 904, and femoral calcar 906. The center of the acetabulum image 902 and the center of the femoral head image 904 are indicated by a circular marker. The femoral calcar image 906 is indicated by a triangular marker. The two markers are separated by a distance d. The distance d may be determined in the plane of the radiograph 900. A computing device may be programmed or configured to automatically detect the images 902, 904, and 906 and place the markers in the appropriate position. Alternatively, a user may manually place the markers at the appropriate location of the radiograph 900 or a digital representation thereof using a graphical user interface. The computing device may determine the distance d based on the positions of the markers by, for example, counting the number of pixels separating the markers.

FIG. 9B illustrates a cross table lateral hip radiograph 908 of the same human hip. The center of the acetabulum image 902 and the femoral calcar image 906 are located at different heights, separated by a vertical distance h, above the radiographic receiver. In FIG. 9A, the vertical distance h (not illustrated) is coming out of the page. As a result, the femoral calcar image 906 and the acetabulum image 902 have two different magnifications on the AP radiograph 900. A computing device may likewise be programmed or configured to determine the distance h based on the positions of the circular and triangular markers in radiograph 908 as described above.

According to the methods described herein, the image of each object of interest may be scaled based on the level of magnification corresponding to the particular image. For example, the magnification of the acetabulum image 902 may be determined based on the height of the acetabulum above the radiographic receiver, using any of the embodiments described with respect to FIGS. 6A-8B. Similarly, the magnification of the femoral calcar image 906 may be determined based on the height of the femoral calcar above the radiographic receiver. For example, radiograph 900 may be a first of two AP hip radiographs. Radiograph 900 may be used with a second AP hip radiograph (not illustrated) according to the embodiments described with respect to FIGS. 6A-7E to determine the magnification of acetabulum image 902 by determining the height of the acetabulum and determine the magnification of the femoral calcar 906 by determining the height of the femoral calcar.

Alternatively, radiographs 900 and 908 may be used together according to the embodiment described with respect to FIGS. 8A and 8B to determine the magnification of acetabulum image 902 and femoral calcar image 906. The height difference h may be determined based on any of the embodiments of FIGS. 6A-8B.

The acetabulum image 902 may be scaled based on its determined magnification to display the actual physical size of the acetabulum. Likewise, femoral calcar image 906 and femoral head image 904 may be scaled based on the determined, corresponding magnifications to display the actual physical size of femoral calcar and femoral head. Accordingly, the templating process may account for the different magnifications of the different anatomical features of the hip. For example, two or more templates may be used, each with a scaling factor accurate for the specific object being measured (e.g. femoral calcar, femoral head, acetabulum). Some embodiments may apply the same scaling factor to every object of interest determined to be at a particular height. Some embodiments may comprise a computing device causing a display to show an object scaled according to its determined magnification, along with an unscaled template overlaid thereon.

Figure 9C:
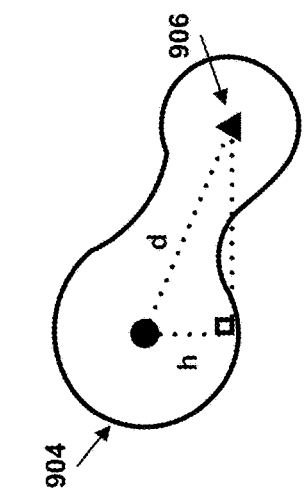
FIG. 9C illustrates an axial view of the human hip, according to an example embodiment.

Additionally, the methods described herein may allow the spatial orientation of an object to be determined based on the height of two or more different points on or features of the object. For example, by determining the height of the femur head corresponding to image 904 and the height of the femoral calcar corresponding to image 906, the rotation of the femur may be determined. FIG. 9C illustrates an axial view (the transverse cross-sectional plane of the human body) of the human hip depicted in radiograph 900 of FIG. 9A and radiograph 908 of FIG. 9B. The overlaid geometry illustrates how the measured distance d and the determined height difference h form a right triangle. The height difference h may be determined by calculating the difference between the height of the femur head and the femoral calcar as previously described. FIG. 9D shows the overlaid geometry of FIG. 9C enlarged and modeled as triangle 910 labeled with the corresponding dimensions. Based on triangle 910, angle ω may be expressed according to Equation (47) and angle ε may be expressed according to Equation (48) or, equivalently, according to Equation (49).

$$w = \sin^{-1}(h/d) \quad (47)$$

$$\varepsilon = 90 - \omega \quad (48)$$

$$\varepsilon = \cos^{-1}(h/d) \quad (49)$$

In the present example embodiment, the angles ω and ε may represent the extent of hip rotation. For example, angle ω may represent the extent of femoral anteversion. Angle ε may be an alternative way of representing femoral version (twist). Alternative embodiments may determine the spatial orientation of other body parts or objects using the methods described herein. Some embodiments may acquire more than two images in order to determine the spatial orientation in multiple reference planes. Example embodiments may determine the spatial orientation of multiple objects present in the same image. For example, the degree of rotation of both hips may be determined at the same time, provided that the radiograph encompasses both hips.

The determined degree of hip rotation, or more generally, the determined three-dimensional spatial orientation of an object of interest, may be used in combination with templating techniques. Specifically, the object of interest may be templated using templates that reflect the 3D spatial orientation of the object being measured. The templates may be three-dimensional representations of prostheses and may be rotated into that same 3D spatial orientation as the object in order to select a prosthesis closest in size and shape to the object. Alternatively, the templates may be two-dimensional and may comprise a plurality of images of the prostheses representing different spatial orientations of the prostheses.

Figure 10C:
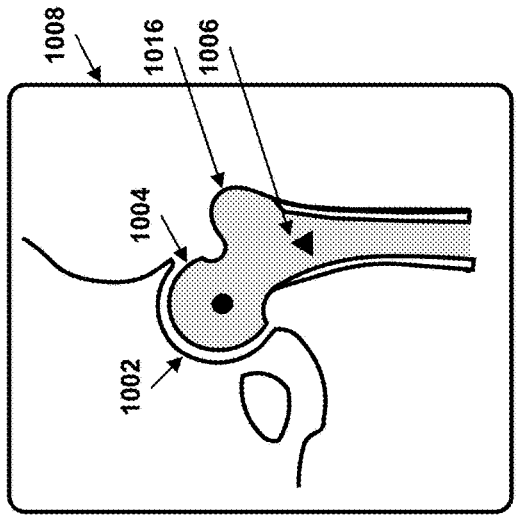
FIG. 10C illustrates an anteroposterior radiograph of the human hip in a rotated position, according to an example embodiment.
Figure 10D:
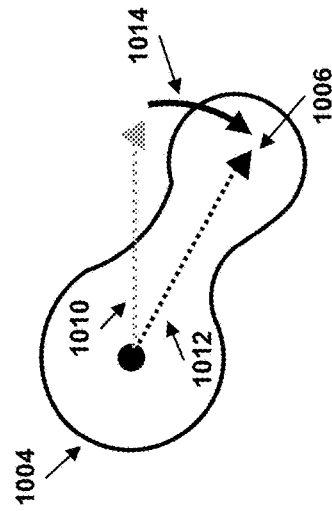
FIG. 10D illustrates an axial view of the human hip in the rotated position of FIG. 10C, according to an example embodiment.
Figure 10A:
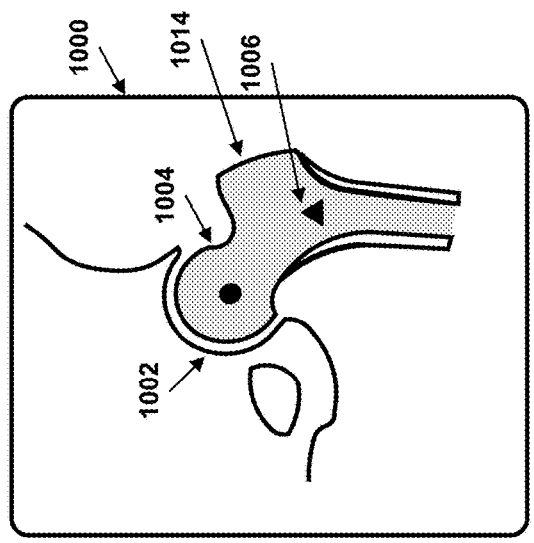
FIG. 10A illustrates an anteroposterior radiograph of a human hip in a neutral position, according to an example embodiment.
Figure 10B:
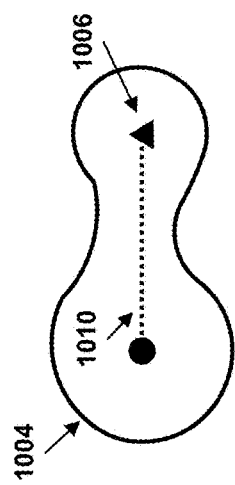
FIG. 10B illustrates an axial view of the human hip in the neutral position of FIG. 10B, according to an example embodiment.

In contrast, using a template that does not correspond to the spatial orientation of the object of interest may result in measurement error because the shape of the image of the object may be significantly different depending on the spatial orienting of the object during image acquisition. For example, the shape of the image of the hip changes significantly as the hip is rotated, as illustrated in FIGS. 10A-10D. FIG. 10A illustrates a radiograph 1000 of a human hip comprising acetabulum image 1002, femoral head image 1004, and femoral calcar image 1006. The radiograph 1000 is taken when the hip is at a neutral position as illustrated by the axial view of the hip in FIG. 10B. Specifically, the line 1010, connecting the circular marker indicating the center of the head of the femur and the triangle indicating the femoral calcar, is horizontal (parallel to the coronal plane of the human body). FIG. 10C illustrates a second radiograph 1008 of the same human hip taken when the hip is rotated. The degree of rotation is illustrated in FIG. 10D by line 1014, showing the change from the original alignment of the circular marker indicating the center of the head of the femur and the triangle indicating the femoral calcar along line 1010 to the new alignment along line 1012. It may be observed that the anatomical feature image 1014 of the femur in radiograph 1000 looks different than anatomical feature image 1016 in radiograph 1008 due to the femur being oriented (rotated) differently in the two images.

Consequently, using a template that does not reflect the same degree of rotation as does the image of the hip may result in selection of a hip replacement prosthesis that does not accurately match the anatomy of a given patient. Determining the degree of hip rotation, as described above, allows for the selection of a template that corresponds to the image of the hip at the given orientation. As a result, the process of selecting a replacement hip prosthesis may be based on templates that accurately reflect the orientation of the hip at the time of image acquisition. Furthermore, the advantages of rotational template adjustment, as described above, are not limited to hip and may be extended to any body part of interest. The techniques described herein may also be applied during radiographic imaging without the templating process in order to produce a more accurate representation of the anatomical proportions of the objects of interest.

VII. EXAMPLE IMPLEMENTATIONS USING A CALIBRATION MARKER

Existing approaches for determining image magnification require that a medical professional (e.g., a radiography technician) place a marker of known size at the same height as the object of interest. Such methods rely on only one image of the object of interest. Since the marker and the object of interest are at the same height, the magnification of the object of interest should be the same as the magnification of the marker. Additionally, since the size of the marker is known, the magnification may be determined based on the ratio of the size of the image to the actual size of the marker.

This method assumes that the marker was correctly placed at the height of the object of interest, using proper technique by the medical professional. When the marker is not placed correctly, the size of the object of interest may be incorrectly determined, leading to complications. For example, in the case where the hip is being sized for a replacement prosthesis, determining the size incorrectly may lead to the medical professional ordering incorrectly sized hardware and/or attempting to insert the incorrectly sized hardware during surgery. The embodiments described herein eliminate the need for positioning a calibration marker at the same height as the object of interest. Instead, the marker may be placed at any height reasonably close to that of the object of interest.

In automated radiography systems, human error associated with positioning the radiation source and receiver is eliminated. The embodiments described herein may accurately determine the size and orientation of the object of interest based an accurate record of the relative position between a radiation source and a radiation receiver at the moment that a corresponding radiograph is captured. However, in radiography systems without automated position feedback systems, a technician may manually determine and record the relative position of the radiation source and the receiver. Human error in positioning the radiation source and receiver, determining the relative position between the radiation source and receiver, and/or recording the relative position between the radiation source and receiver may result in errors in the determined image magnification which may in turn lead to surgical complications.

The example embodiments that follow, in combination with the methods described above, may allow for the reduction or elimination of human error by using a calibration marker to determine the relative position of the radiation source and the radiation receiver. Contrary to other methods, the calibration marker may not need to be placed at the same height as the object of interest. Instead, the marker may be attached to the radiation source or placed on the radiation receiver or radiation receiver holder (e.g., patient table). The calibration marker method does not require special equipment (aside from the marker itself). Additionally, the calibration marker approach described herein does not require additional staff training and/or testing and may be used with any radiation imaging apparatus.

In general, the calibration marker method may be used whenever consistent placement of the radiation source in relation to the radiation receiver is important. The marker itself may be made of any material such that, under commonly used radiation intensities and exposure times, a clear image of the marker is produced on the radiation receiver (otherwise called a radio dense material). The calibration marker may be used to identify and correct for errors in the placement of the radiation source and other human error. Specifically, the calibration marker method may be used to accurately determine the position of the radiation source relative to the radiation receiver in systems where that position is not automatically determined or where manual determination of the position may be subject to errors. Alternatively or additionally, the calibration marker may be used to determine the difference between the known height of the calibration marker and an unknown height of the object of interest.

In general, the marker may have a known size and may be positioned at a known position, vertical and/or horizontal, in relation to either the source or receiver. Mathematically, the number of known variables with respect to the size and/or position of the calibration marker may be equal to or greater than the number of independent equations describing the position of the radiation source in relation to the receiver in a particular geometric arrangement. As a result, the position of the radiation source in relation to the receiver may be determined based on the known properties of the calibration marker. Specifically, the known variables may be any two of the set including the height of the marker above the receiver or below the source, the horizontal position of the marker with respect to the receiver or the source, and the size of the marker.

Figure 11:
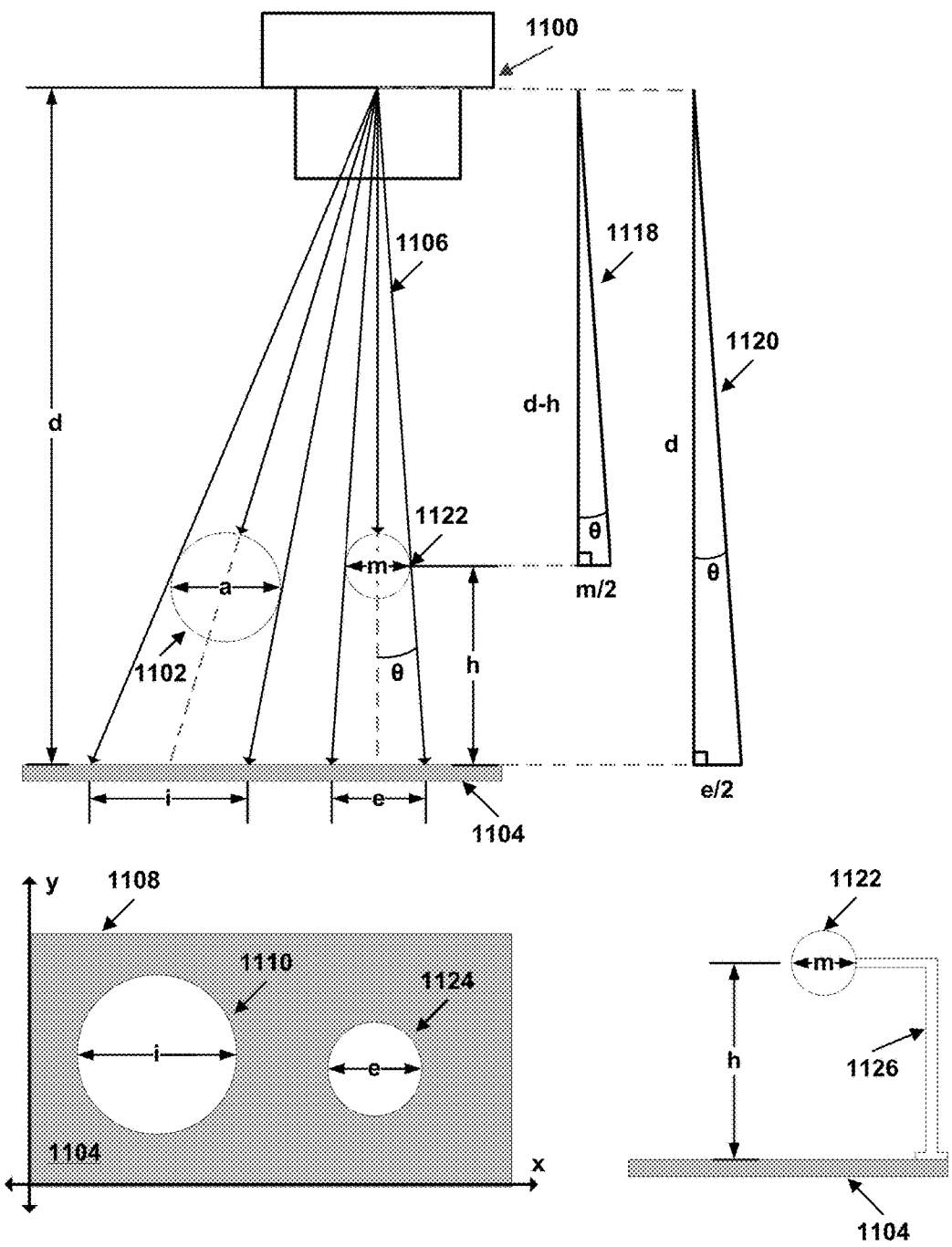
FIG. 11 illustrates a calibration marker being used to determine the position of a radiation source, according to an example embodiment.

FIG. 11 illustrates an example embodiment in which a calibration marker is used to determine the height of the radiation source. Radiation source 1100 is positioned an unknown distance d above receiver 1104 and emits radiation 1106. The distance d may be unknown due to a lack of means for measuring the distance accurately. Alternatively, the distance may be uncertain in that it may have been inaccurately or erroneously measured by a radiography technician. The calibration marker may be used to determine, verify, and/or validate the position of the radiation source 1100 in relation to receiver 1104.

Object of interest 1102, having an unknown size (diameter) a, and calibration marker 1122, having a known size (diameter) m and positioned a known height h above the radiation receiver 1104, are exposed to radiation 1106. The calibration marker produces image 1124, having a measurable size e, and the object 1102 produces image 1110, having a measurable size i, as illustrated in the top view 1108 of receiver 1104. The calibration marker may be held at the fixed height h by a support 1126 placed on the receiver 1104 or a receiver holder.

Using triangles 1118 and 1120, height d of radiation source 1100 may be derived by combining Equations (50) and (51), resulting in Equation (52).

$$\tan(\theta) = \frac{m/2}{d-h} \quad (50)$$

$$\tan(\theta) = \frac{e/2}{d} \quad (51)$$

$$d = \frac{eh}{e-m} \quad (52)$$

With the height of the radiation source 1100 now known, the magnification of image 1110 of the object of interest 1102 may be determined according to any of the embodiments previously described. Alternative embodiments may use different spatial arrangements and/or geometric models of the spatial arrangements of the source 1100, marker 1122, and receiver 1104 in order to determine the position of the radiation source 1100 in relation to the receiver 1104.

Figure 12A:
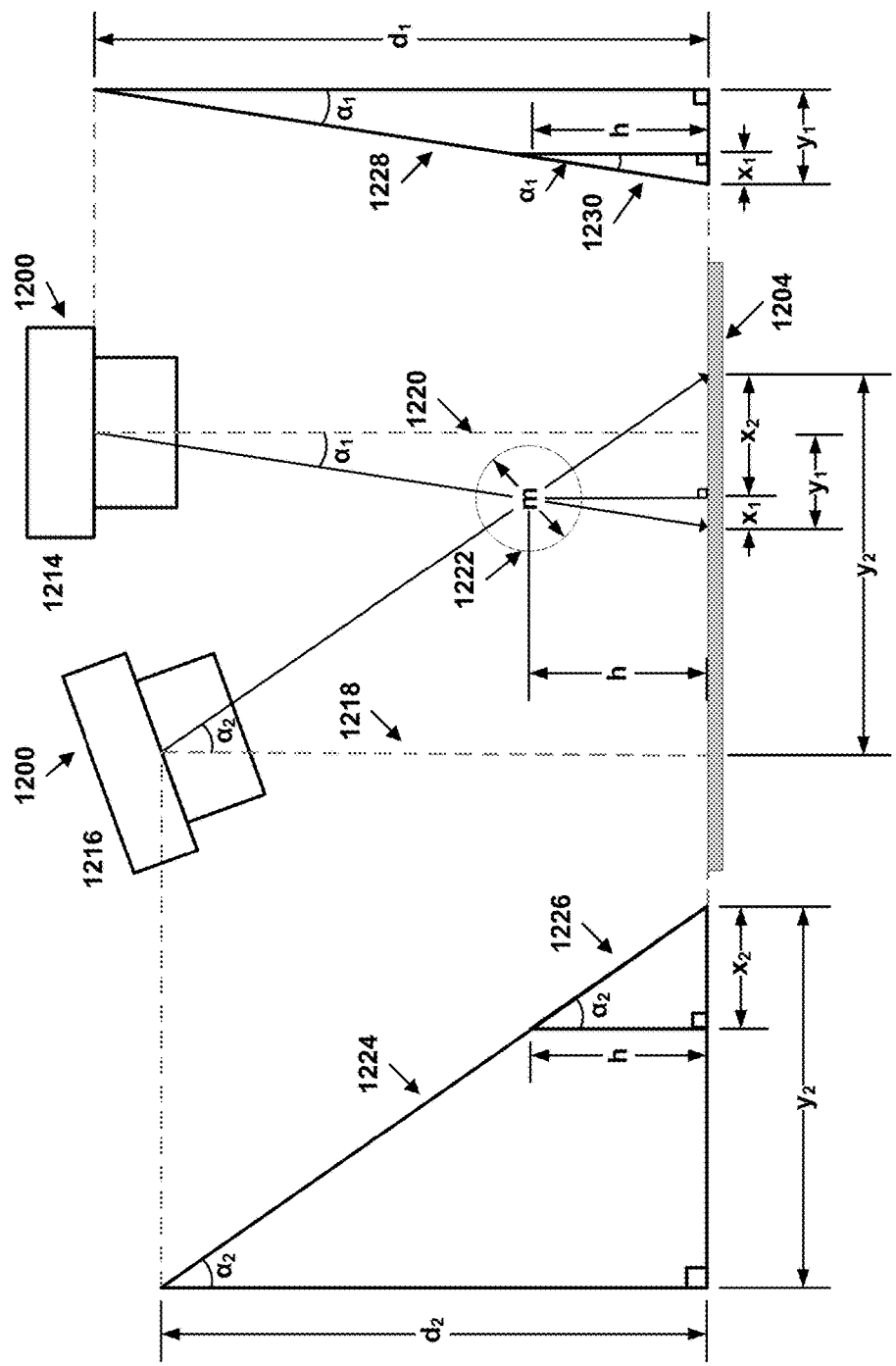
FIG. 12A illustrates another example of a calibration marker being used to determine the position of a radiation source, according to an example embodiment.

FIG. 12A illustrates another example embodiment where the position of the radiation source in relation to the receiver is determined based on known properties of the calibration marker. Similarly to FIGS. 7A-7C, two images of the calibration marker 1222 and the object of interest (not shown) may be taken using radiation source 1200 positioned above receiver 1204. The first image may be taken with radiation source 1200 at position 1214, an unknown distance $d_1$ above the receiver 1204. The horizontal position, designated by line 1220, may also be unknown. Similarly, a second image may be taken with radiation source 1200 at position 1216, an unknown distance $d_2$ above the receiver 1204. The horizontal position, designated by line 1218, may also be unknown. As with the embodiment of FIG. 11, the position of the radiation source 1200 in relation to the radiation receiver 1204 may be unknown due to a lack of means for measuring the distance accurately, uncertainty in measurements of the position, and/or erroneous measurements of the position by a radiography technician. The calibration marker may be used to determine, verify, and/or validate the position of the radiation source 1200 in relation to receiver 1204. The calibration marker 1222 may have a known size m, a known height h, and may be placed at a known horizontal distance in relation to the radiation receiver 1204.

The distance $d_1$ may be determined based on the magnification of the marker of known size m. Specifically, $d_1$ may be derived from Equation (53), where ($e_1$) is the size of the first image (image taken from position 1214, not shown) and where Equation (53) is a combination of Equations (1) and (6).

$$M_1 = \frac{d_1}{d_1 - h} = \frac{e_1}{m} \quad (53)$$

The distance $d_1$ may be expressed according to Equation (54).

$$d_1 = \frac{e_1 h}{e_1 - m} \quad (54)$$

Likewise, $d_2$ may be derived from Equation (55), where $e_2$ is the size of the second image (image taken from position 1216, not shown) and where Equation (55) is a combination of Equations (2) and (8).

$$M_2 = \frac{d_2}{d_2 - h} = \frac{e_2}{m} \quad (55)$$

The distance $d_2$ may be expressed according to Equation (56).

$$d_2 = \frac{e_2 h}{e_2 - m} \quad (56)$$

Some embodiments may remove and/or account for image elongation via any of the methods previously discussed with respect to FIGS. 7A-7E.

The horizontal position of the radiation source 1200 at position 1214 may be derived based on triangles 1228 and 1230. Specifically, the angle $\alpha_1$ may be expressed according to Equation (57), where $x_1$ is the distance between the center of the image taken from position 1214 and the x-position of the calibration marker 1222.

$$\alpha_1 = \tan^{-1}\left(\frac{x_1}{h}\right) \quad (57)$$

The distance $y_1$, corresponding to the distance between the center of the first image taken from position 1214 and the x-position of the radiation source 1200 at position 1214 may be expressed according to Equation (58).

$$y_1 = d_1 \tan(\alpha_1) \quad (58)$$

Consequently, the spatial position of radiation source 1200 in relation to receiver 1204 may be determined based on known properties of the calibration marker. The analogous procedure may be carried out for triangles 1224 and 1226 to determine the distance $y_2$ according to Equation (59).

$$y_2 = d_2 \tan(\alpha_2) \quad (59)$$

With the spatial position of the radiation source 1200 in relation to receiver 1204 known at both positions 1214 and 1216, the magnification of the image of the object of interest (not shown) may be determined. The determined magnification may be used to scale the image of the object of interest in order to determine the actual physical size of the object of interest. The scaled image of the object of interest may subsequently be used with digital templating methods to determine a template closest in size to the actual physical size of the object of interest.

In some example embodiments, the calibration marker may be disposed upon or placed on a radiation receiver housing, instead of being placed directly on the radiation receiver itself. Alternatively, the calibration marker may be placed on a radiographic table next to or above the radiation receiver housing. In some example embodiments, the radiation receiver housing may have a feature or structure on or in which a calibration marker may be placed or attached. For example, some radiation systems may comprise a radiation receiver in the form of an X-ray cassette. The X-ray cassette may be held by or housed in a cassette holder. The calibration marker may be placed on the cassette holder. However, in some radiography systems, the radiation receiver might fit imprecisely in the radiation receiver housing. For example, the radiation receiver housing may be slightly bigger than the radiation receiver (e.g., the cassette holder may be bigger than the X-ray cassette). The imprecise fit may allow the radiation receiver to move around inside the radiation receiver housing. Consequently, since the calibration marker may be placed on the radiation receiver housing or on a radiographic table, the position of the calibration marker in relation to the radiation receiver may undesirably change between acquisitions of the first radiograph and the second radiograph.

For example, a first radiograph may be captured on a first X-ray cassette held in a cassette holder. The first X-ray cassette may be removed from the cassette holder. The radiation source may be moved to a second position and/or orientation with respect to the X-ray cassette and/or the cassette holder. A second X-ray cassette may be inserted into the cassette holder. However, due to an imprecise fit, the second cassette may be in a slightly different position inside the cassette holder than the first X-ray cassette. While the calibration marker may remain in the same position in relation to the radiation receiver housing, the calibration marker may be in a slightly different position in relation to the radiation receiver itself (the second X-ray cassette). Accordingly, calculations that assume that the calibration marker is in the same position in relation to the first radiation receiver (first X-ray cassette) and the second radiation receiver (second X-ray cassette) may produce results containing calculation errors.

In alternative embodiments, the radiation receiver may be an integral part of the radiation receiver housing. For example, in radiography systems where the radiation receiver is an electronic detector (e.g., sensor array), the radiation receiver might not need to be changed between acquisitions of successive images. In such embodiments, placement of the calibration marker on the radiation receiver housing, positioning of the calibration marker with respect to the radiation receiver housing, and/or attachment of the calibration marker to the radiation receiver housing may be equivalent to placement, positioning, and/or attachment of the calibration marker to the radiation receiver itself since the radiation receiver and the radiation receiver housing may be precisely and firmly fitted and/or connected together.

Alternatively, the calibration marker may be placed, positioned, and/or attached directly to the radiation receiver itself as opposed to the radiation receiver housing. For example, the calibration marker may be placed, positioned, and/or attached directly to the electronic detector as opposed to the housing of the detector. In embodiments utilizing X-ray film and/or X-ray cassettes, placement, positioning, and/or attachment of the calibration marker directly to the film or cassette may be impossible, impractical, or inaccurate. Accordingly, FIG. 12B illustrates an example embodiment that may be used to account for an imprecise fit of a radiation receiver inside of a radiation receiver housing.

Figure 12B:
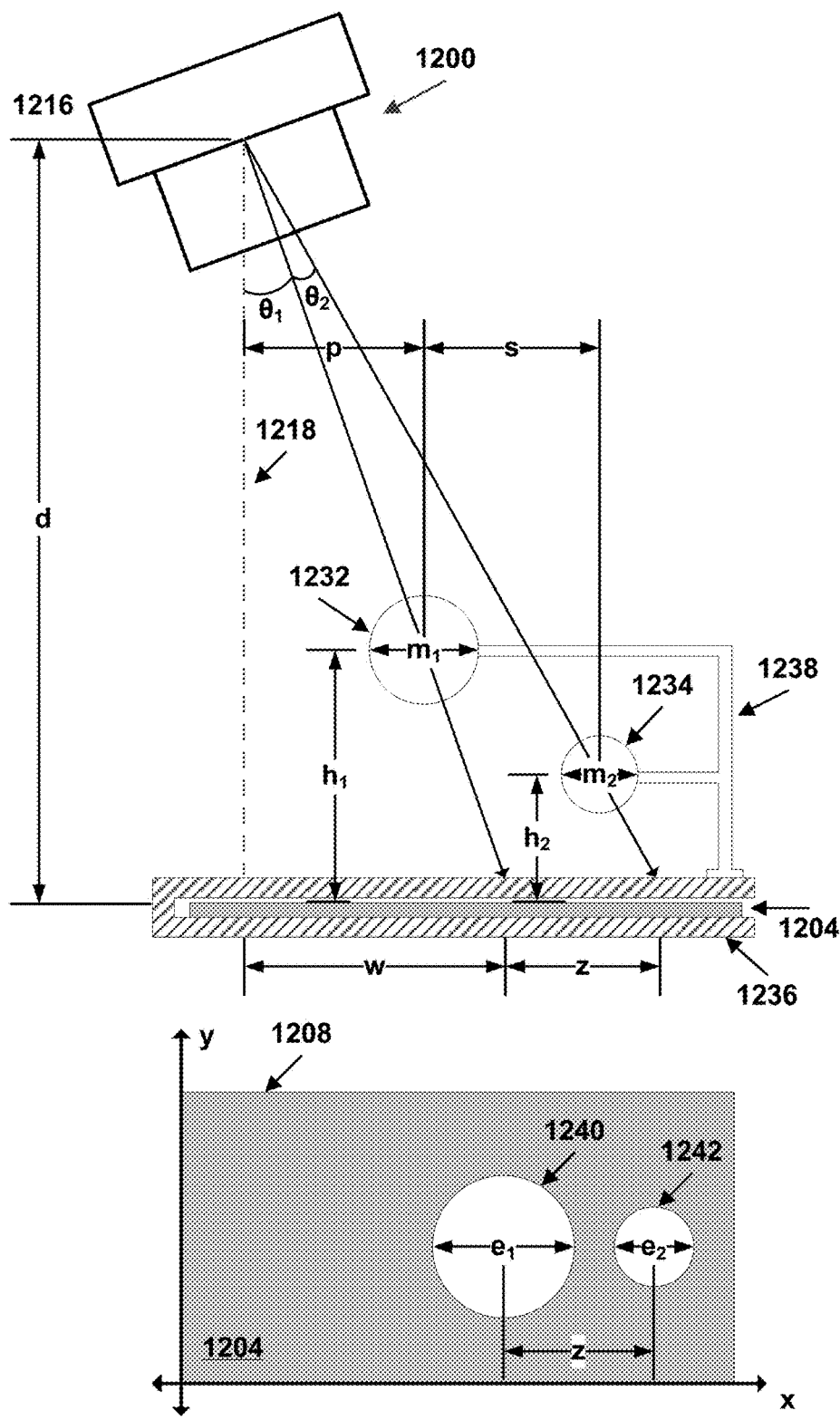
FIG. 12B illustrates yet another example of a calibration marker being used to determine the position of a radiation source, according to an example embodiment.

In particular, FIG. 12B illustrates a radiation source 1200 located at position 1216 above radiation receiver 1204. Position 1216 may be a distance d above the radiation receiver 1204 and may correspond to an x-coordinate position represented by line 1218. Radiation receiver 1204 may be housed in a radiation receiver housing 1236. The radiation receiver 1236 may also be called a radiation receiver holder (e.g., X-ray cassette holder). The radiation receiver 1204 may be smaller than radiation receiver housing 1236, resulting in an imprecise fit of the radiation receiver 1204 in the radiation receiver housing 1236. Accordingly, there may be variation in how different radiography technicians or medical professionals position the radiation receiver 1204 in radiation receiver housing 1236.

FIG. 12B additionally illustrates a first calibration marker 1232 and a second calibration marker 1234 attached to or retained by a calibration marker support structure 1238. The calibration marker support structure 1238 may be placed on, positioned with respect to, and/or attached to the radiation receiver housing 1236 at a known position. For example, radiation receiver housing 1236 may have a special slot specifically designed to retain and/or attach to the calibration marker support structure 1238. However, this is not required. The first calibration marker 1232 may have a known diameter $m_1$ and may be located at a known height $h_1$ above the radiation receiver. The second calibration marker 1234 may also have a known diameter $m_2$ and may be located at a known height $h_2$ above the radiation receiver. The calibration markers 1232 and 1234 may be separated from each other by a known horizontal distance s. The calibration markers 1232 and 1234 may produce corresponding images 1240 and 1242, respectively, as illustrated in the top view 1208 of radiation receiver 1204.

An x-y coordinate frame is shown attached to the top view 1208 of radiation receiver 1204. Variation in positioning of the radiation receiver 1204 inside of the radiation receiver housing 1236 may include a variation in the y-coordinate position of the radiation receiver 1204 and/or a variation in the x-coordinate position of the radiation receiver 1204. Since the calibration markers 1232 and 1234 are located in a known position with respect to the radiation receiver housing 1238, variation in the position of the radiation receiver 1204 inside the radiation receiver housing 1236 may change the relative position between the radiation receiver 1204 and the calibration markers 1232 and 1234. Under such conditions, an assumption or estimation of the location of the calibration markers 1232 and 1234 in relation to the radiation receiver 1204 may be inaccurate and/or incorrect and may lead to an inaccurate determination of the magnification of the corresponding images of an object of interest.

However, by using at least two calibration markers, as illustrated in FIG. 12B, the position of the radiation source 1200 in relation to the radiation receiver 1204 may be determined without assuming or estimating the position of the at least two calibration markers in relation to the radiation source 1204. Instead, determination of the position of the radiation source 1200 in relation to the radiation receiver 1204 may be based on the known distance s between the two calibration markers. Specifically, the height d of the radiation source 1200 above radiation receiver 1204 may be determined, as discussed previously, according to Equation (52) using either calibration marker 1232 and image 1240 or calibration marker 1234 and image 1242. Alternatively, some embodiments may perform a redundant calculation using both calibration markers 1232 and 1234 and corresponding images 1240 and 1242 in order to verify the results against each other.

Figure 12C:
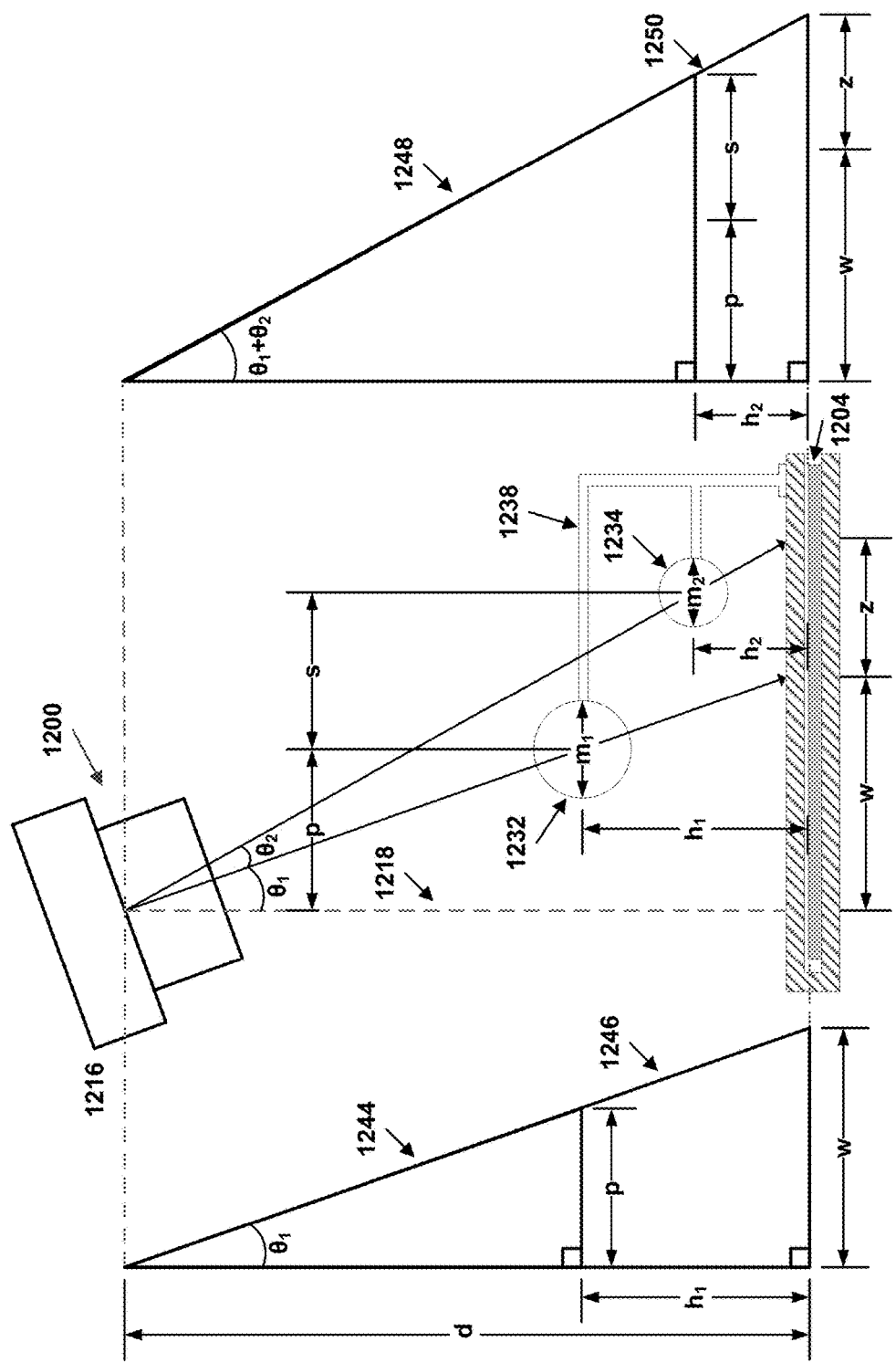
FIG. 12C illustrates a geometric model of FIG. 12B, according to an example embodiment.

The embodiment illustrated in FIG. 12B may be modeled as illustrated in FIG. 12C. The example model illustrated in FIG. 12C may be used to determine the position of radiation source 1200 in relation to radiation receiver 1204 and avoid any error resulting from imprecise positioning of the radiation receiver 1204 inside radiation receiver housing 1236. In particular, Equations (60) and (61) may be written based on triangles 1244 and 1246, respectively.

$$\tan(\theta_1) = \frac{p}{d - h_1} \qquad (60)$$

$$\tan(\theta_1) = \frac{w}{d} \qquad (61)$$

The distance z may be determined based on a radiograph containing the images 1240 and 1242 by measuring the distances between the centers of the respective images. Alternative embodiments may utilize a geometric model where the distance z may be determined between the edges of images 1240 and 1242. In some embodiments, the distance z may be determined by a computing device using known feature detection and image recognition algorithms such as, for example, the Hough circle transform. Equations (60) and (61) may be combined into Equation (62).

$$\frac{p}{d - h_1} = \frac{w}{d} \qquad (62)$$

Similarly, Equations (63) and (64) may be written based on triangles 1248 and 1250, respectively, where distance p is the distance between calibration marker 1232 and the line 1218 representing the x-coordinate of the radiation source 1200.

$$\tan(\theta_1 + \theta_2) = \frac{p + s}{d - h_2} \qquad (63)$$

$$\tan(\theta_1 + \theta_2) = \frac{w + z}{d} \qquad (64)$$

Equations (63) and (64) may be combined into Equation (65).

$$\frac{p + s}{d - h_2} = \frac{w + z}{d} \qquad (65)$$

Equations (62) and (65) may be combined and used to determine the distance w according to Equation (66).

$$w = \frac{z(d - h_2) - sd}{h_2 - h_1} \quad (66)$$

After determining d and w for the first orientation, a second radiograph may be acquired from a second orientation by changing the relative position between the radiation source 1200 and the radiation receiver 1204. The position of the radiation source 1200 in relation to radiation receiver 1204 in the second orientation may be determined in an analogous manner. The determined positions of the radiation source 1200 in relation to the radiation receiver 1204 in the two orientations may be used to determine a magnification of an image of an object of interest (not shown) by determining the height of the object of interest above the radiation receiver 1204 according to any of the embodiments described herein. For example, the magnification may be determined by measuring a size (e.g., dimension such as a diameter, width, length, etc.) of an image of an object of interest as discussed in detail with respect to FIGS. 6A-7E. Alternatively, the magnification may be determined by measuring a distance between an anchor point and a reference point on the image of the object of interest, as discussed in detail with respect to FIGS. 14C-14E.

FIGS. 13A and 13B illustrate how a calibration marker may be used to determine the height and magnification of an object of interest by determining a difference between a known height of a calibration marker and an unknown height of the object of interest. In FIG. 13A, radiation source 1300 is located at position 1314, an unknown distance $d_1$ above receiver 1304. Object of interest 1302, having an unknown size a and located at an unknown height h above the receiver 1304, may be exposed to radiation, producing image 1310 that has a known (measurable) diameter $i_1$, as illustrated in the top view 1308 of receiver 1304. Calibration marker 1322, having a known size m, may be positioned a known height b above the receiver 1304 using support structure 1326. Calibration marker 1322 may also be exposed to radiation, producing image 1324 that has a known (measurable) diameter $e_1$, as illustrated in the top view 1308 of receiver 1304.

Radiation source 1300 may subsequently be moved from position 1314 to position 1316, as indicated by arrow 1320 in FIG. 13B. Additionally, the receiver 1304 may also be rotated as from the position shown in FIG. 13A to the position shown in FIG. 13B. The radiation source 1300 may be separated from radiation receiver 1304 by an unknown distance $d_2$. The object of interest 1302 and calibration marker 1322 may be exposed to radiation, producing images 1312 and 1318, respectively. Image 1312 may have a known (measurable) diameter $i_2$. Similarly, image 1318 may have a known (measurable) diameter $e_2$. Coordinate systems (x-y in FIG. 13A and y-z in FIG. 13B) are shown attached to the top view 1308 to illustrate the 3D spatial relationship of the acquired images 1310, 1324, 1312, and 1318.

The distances $d_1$ and $d_2$ may be determined according to Equations (67) and (68). Some embodiments may account for image elongation as shown by the example illustrated with respect to FIGS. 7A-7E.

$$d_1 = \frac{e_1 b}{e_1 - m} \quad (67)$$

$$d_2 = \frac{e_2 b}{e_2 - m} \quad (68)$$

The vertical distance $\Delta d$ between the image 1312 and image 1318 may be determined by manual or automated measurements. The distance may be measured from the center of image 1312 to the center of image 1318, as illustrated. For example, a user may be prompted by a computing device to select (e.g., by clicking, pointing, touching, or dragging a marker) the centers of images 1312 and 1318. In some embodiments, the computing device may be programmed to automatically determine the centers of images 1312 and 1318 and measure the distance $\Delta d$. Alternatively, the distance may be measured from the bottom of image 1312 to the bottom of image 1318, provided that a meaningful height difference is determined.

Based on the vertical height difference $\Delta d$, the height h of the object of interest 1302 may be expressed according to Equation (69).

$$h = b + \Delta d \quad (69)$$

In the present embodiment, only the height b and the size m of the calibration marker 1322 need to be known in order to determine the magnification of the object of interest 1302. Alternative embodiments may produce elongated images of the object of interest and the calibration marker and may account for the elongation in a manner analogous to that previously discussed with respect to FIGS. 7A-7E. Regardless, with the height h now known, the magnification of the image 1310 of object of interest 1302 may be determined according to Equation (6). The image 1310 may be scaled to represent the actual physical size a of the object of interest, and the actual size a may be used in combination with digital templating techniques to select a template object closest in size to the object of interest.

Alternatively, the distance c between the calibration marker 1322 and receiver 1304 as positioned in FIG. 13B may be known. The distance $\Delta w$ may be determined and used to compute the distance f according to Equation (70).

$$f = c + \Delta w \quad (70)$$

The distance f may be used to determine the magnification $M_2$ of image 1312 according to Equation (71).

$$M_2 = \frac{d_2}{d_2 - f} \quad (71)$$

The determined magnification $M_2$ may be used to scale the image 1312 to represent the actual physical size of the object of interest 1302.

FIG. 14A illustrates an embodiment where a calibration marker may be attached to a radiation source or radiation source housing. The calibration marker may be used to correct for errors in radiographic technique by solving for the exact position of the radiation source relative to a radiation receiver. Radiation source 1400 is positioned at location 1414 above a radiation receiver 1404. The radiation beam projected by radiation source 1400 may be adjusted, automatically or manually, to a position directly perpendicular to radiation receiver 1404. Two calibration markers 1402 and 1406 are attached to the radiation source 1400. FIG. 14B illustrates a scaled geometric representation of the region surrounding the calibration markers 1402 and 1406. Specifically, FIG. 14B illustrates that both markers have a size m and are offset by a known height h and a known horizontal distance b from the radiation beam. The marker 1402 produces image 1408 having a size $e_1$ (not shown) and marker 1406 produces image 1410 also having a size $e_1$ (also not shown). The radiation source 1400 at position 1414 is an unknown distance $d_1$ above the radiation receiver. The distance $d_1$ may be unknown or uncertain for any of the reasons previously described herein.

The calibration markers 1402 and 1406 may be used to determine the distance $d_1$. Specifically, $d_1$ may be determined based on the trigonometric relations of Equations (72) and (73).

$$\tan(\alpha_1) = \frac{b}{h} \tag{72}$$

$$\tan(\alpha_1) = \frac{x_1}{d_1} \tag{73}$$

Using these equations, the distance $d_1$ may be expressed according to Equation (74), where h and b are known and $x_1$ may be determined based on the images 1408 and 1410.

$$d_1 = \frac{x_1 h}{b} \tag{74}$$

For example, an image representation of the entire radiation receiver 1404, including images 1408 and 1410, may be digitized and processed in software to measure the distances $x_1$, $x_2$, and $x_3$ using known image processing methods. Since the distance $x_1$ and the position $x_2$ of image 1408 relative to the radiation receiver 1404 are known, the relative position $x_1+x_2$ between the radiation source 1400 and the radiation receiver 1404 is also known.

The distance $d_1$ may alternatively be determined based on the magnification of images 1408 and 1410. Specifically, the magnification $M_1$ of image 1408 may be expressed according to Equation (75). Accordingly, the distance $d_1$ may be expressed according to Equation (76).

$$M_1 = \frac{d_1}{h} = \frac{e_1}{a} \tag{75}$$

$$d_1 = \frac{e_1 h}{a} \tag{76}$$

Some embodiments may carry out both calculations. Since both embodiments are expected to provide the same result (embodiments may account for image elongation), the redundant calculations may serve as a safety net to catch errors. Although not illustrated, an image of an object of interest may also be acquired at the same time as images 1408 and 1410 are acquired. Consequently, the determined position of radiation source 1400 in relation to radiation receiver 1404 may be used to determine the magnification or orientation of the object of interest via any of the embodiments described herein.

The radiation source 1400, radiation receiver 1404, and the calibration markers 1402 and 1406 may be configured such that images produced by the calibration markers 1402 and 1406 do not significantly overlap the image of the object of interest. Alternatively, the images of the calibration marker may be acquired during a first exposure of the calibration markers 1402 and 1406 to radiation from radiation source 1400. After the first exposure, the calibration marker may be moved out of the radiation field or removed from the radiation source 1400 entirely. The object of interest may subsequently be placed between the radiation source 1400 and the radiation receiver 1404 without changing the relative position of the radiation source 1400 and the radiation receiver 1404. The image of the object of interest may be acquired during a second exposure.

The radiation source 1400 may subsequently be translated from position 1414 to position 1416 by a distance v. The marker 1402 may now produce an image 1418 and marker 1406 may produce image 1420, separated from each other and from images 1408 and 1410 by distances $y_1$, $y_2$, and $x_3$ as shown in FIG. 14A. In a first embodiment, the distance v may be accurately determined via direct measurement. For example, the radiation source 1400 may include a ruler that can accurately track the horizontal position of radiation source 1400. Additionally, the vertical position of the radiation source 1400 may remain unchanged, resulting in the distance $d_2$ being equal to the distance $d_1$. Consequently, the relative position between the radiation source 1400 and radiation receiver 1404 may be determined via simple arithmetic. Specifically, with the relative position $x_1+x_2$ between the radiation source 1400 and receiver 1404 at position 1414 already known, the horizontal position of location 1416 may be determined by adding the distance v to the horizontal coordinate of position 1414 and may be expressed as $x_1+x_2+v$.

In a second embodiment, the distance v may be known but the distance $d_2$ may have changed; the distance $d_2$ may be different from the distance $d_1$. Accordingly, the distance $d_2$ may be determined based on the magnification of image 1418 of marker 1402 or the magnification of image 1420 of marker 1406 as previously described. Alternatively, the distance may be computed based on the trigonometric relation of Equation (77) and may be expressed according to Equation (78).

$$\tan(\beta + 2\alpha_1) = \frac{v - x_1 - x_3}{d_2} \tag{77}$$

$$d_2 = \frac{v - x_1 - x_3}{\tan(\beta + 2\alpha_1)} \tag{78}$$

In a third embodiment, distances $d_2$ and v may both be unknown. The distance $d_2$ may be determined based on the magnification of the image of either marker 1402 or 1406 as previously discussed. The distance v may be expressed by Equation (79), where $y_3$ is the only unknown quantity while all other variables can be determined explicitly based on the images 1408, 1410, 1418, and 1420 or as previously described herein.

$$v = y_3 + y_1 + y_2 + x_3 + x_1 \tag{79}$$

Accordingly, $y_3$ may be derived from Equation (80) and expressed according to Equation (81).

$$\tan(\beta + 2\alpha_1) = \frac{y_3 + y_1 + y_2}{d_2} \tag{80}$$

$$y_3 = d_2 \tan(\beta + 2\alpha_1) - y_1 - y_2 \tag{81}$$

Similarly to prior embodiments, the distance v may now be computed explicitly and added to the x-position of the radiation source 1400 at location 1414 to determine the x-position of the radiation source 1400 at location 1416 in relation to radiation receiver 1404. The now known relative position may be used by any of the methods described herein to determine the magnification and orientation of an object of interest. The image of the object of interest may be scaled and used in digital templating methods to determine a template object closest in size to the object of interest.

In general, more or fewer calibration markers may be used. For example, some embodiments may use three calibration markers attached to the radiation source 1400. Regardless of their number, the calibration makers may be arranged in a particular pattern that facilitates identification of the image corresponding to each calibration marker in a radiograph. Alternatively or additionally, the calibration markers may be arranged in a way that simplifies the computation and/or calculations involved in determining the relative position between radiation source 1400 and radiation receiver 1404. Some embodiments may use both calibration markers attached to the radiation source 1400 as well as calibration markers attached to the radiation receiver 1404.

Alternative embodiments may use multiple redundant calibration markers in order to reduce or eliminate errors by verifying and/or double-checking any calculations. An example embodiment may have a calibration marker attached in a known position relative to the radiation source 1400 and may determine the position of radiation source 1400 in relation to radiation receiver 1404 based on the image of the calibration marker in the corresponding radiograph. A second calibration marker may be attached in a known position relative to the radiation receiver 1404. The image of the second calibration marker may also be used to determine the position of radiation source 1400 in relation to radiation receiver 1404 based on the image of the second calibration marker in the corresponding radiograph. When the two calculations produce significantly different results, a medical professional and/or computing device may require or suggest that the radiographs be taken again in a more careful manner. Conversely, when the calculations produce the same result, the medical professional may be confident in the accuracy of the procedure.

Figure 14E:
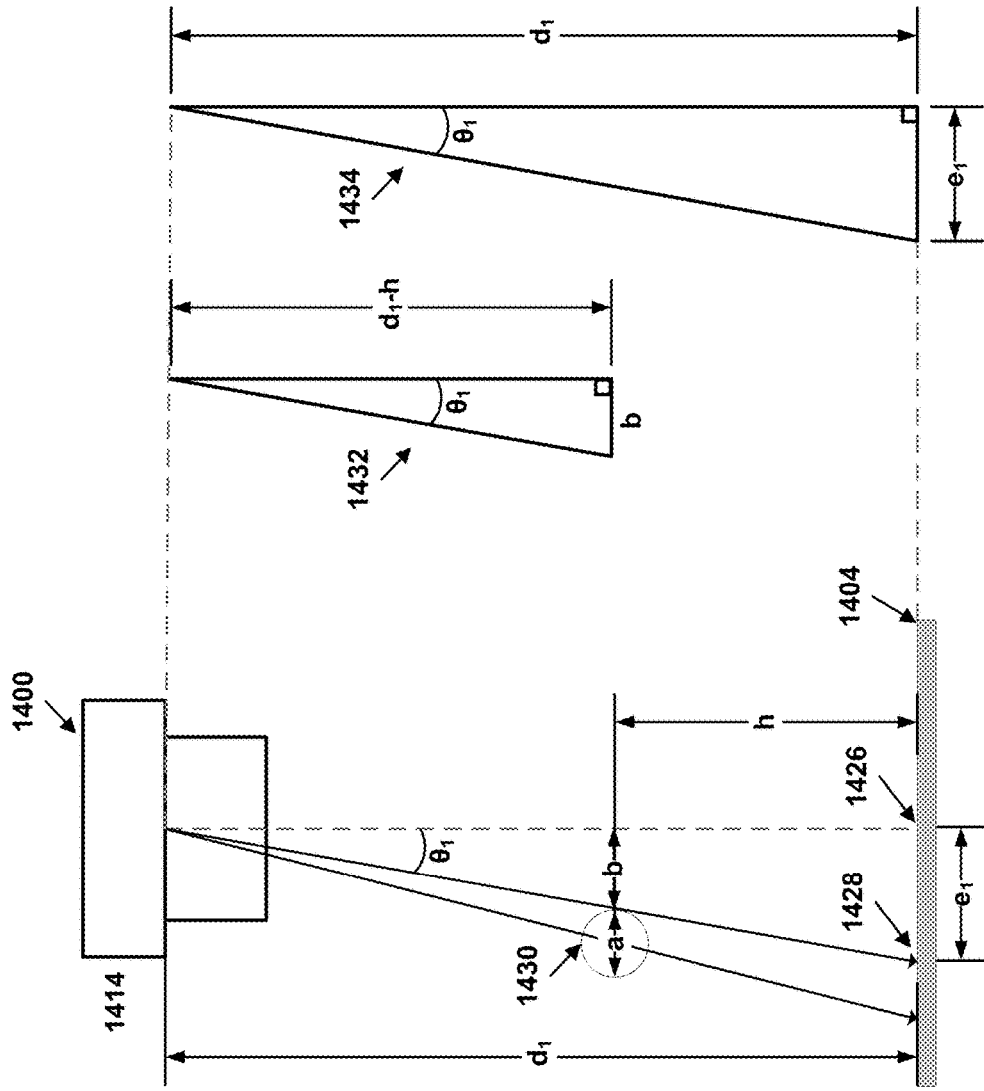

FIGS. 14C-14E illustrate an exemplary embodiment where a magnification of an object of interest is determined based on measurements of a distance between a reference point in an image of the object of interest and an anchor point (another reference point). Specifically, the magnification is based on a first distance between a first reference point of an image of the object of interest contained in a first radiograph and an anchor point in the first radiograph and further based on a second distance between the first reference point of an image of the object of interest contained in a second radiograph and the anchor point in the second radiograph. The anchor point may be another reference point but is referred to herein as an anchor point in order to differentiate it from a reference point in an image of the object of interest. The distinction will be made clear by way of the following example.

FIG. 14C illustrates a radiation source 1400 positioned at position 1414, a distance $d_1$ above a radiation receiver 1404. Two calibration markers, 1402 and 1406, may be attached to the radiation source 1400. The calibration markers 1402 and 1406 may create corresponding calibration markers images 1408 and 1410. As shown in FIG. 14D, the images 1408 and 1410 (shown surrounded by dotted circles for emphasis) may be contained in radiograph 1422 acquired using radiation source 1400 at position 1414 in relation to radiation receiver 1404. A computing device may locate images 1408 and 1410 in the representation of radiograph 1422 by, for example, comparing the color and/or brightness of the pixels in the representation. For circular images, the computing device may look for groups of pixels that fit a model of a circle using the Hough Circle Transform algorithm. The images may 1408 and 1410 may be separated by a distance $2x_1$. Line 1424 connecting the images 1408 and 1410 may be determined. A midpoint 1426 of the line may be determined and may subsequently be used as an anchor point in determining the magnification of the object of interest, according to the present example embodiment.

A distance $e_1$ may be determined or measured between center point (anchor point) 1426 and a reference point 1428 on the image 1427 of the object of interest. The object of interest may be a femoral calcar, as shown in FIG. 14D. In some embodiments, the object of interest may be another anatomical feature. FIG. 14E illustrates a different view of FIG. 14C (some elements not shown for clarity). Specifically, object of interest 1430 (illustrated in FIG. 14C as the femoral calcar) is shown positioned a vertical distance h above radiation receiver 1404. Reference point 1428 and anchor point 1426 are separated by a distance $e_1$.

The distance $d_1$ may be known from a position feedback mechanism of the radiography system that includes the radiation source 1400 and radiation receiver 1404. Alternatively, the distance $d_1$ may be determined based on the calibration marker images 1408 and 1410, as described with respect to FIG. 14A. The distance $e_1$ shown in FIGS. 14C and 14E may be used in the same manner as the diameter and/or size of the image of the object of interest as described in any of the other embodiments described herein. The distance $e_1$ may be used to determine a height of the object of interest and, based on the height, determine the magnification of the image of the object of interest.

Specifically, by way of example, the magnification of the image 1427 contained in radiograph 1422 and/or a second image of the object of interest contained in a second radiograph (not shown) may be determined. The second image may be acquired from a second orientation where the second orientation is achieved by moving the radiation source 1400 up or down from position 1414 into a second position, as discussed with respect to FIGS. 6A-6D. In the second orientation, the radiation source 1400 may be located a distance $d_2$ above the radiation receiver 1404.

Calibration markers 1402 and 1406 may produce corresponding images and a line may be determined connecting the images. The line may have a length $2x_2$ and a midpoint of the line may be used as an anchor point in the second radiograph. The anchor point in radiograph 1422 and the anchor point in the second radiograph may coincide with the same underlying anatomical feature depicted in the radiographs. Accordingly, the anchor point may be a stationary reference point that does not move relative to radiograph 1422 and the second radiograph. A second distance $e_2$ (not shown) may be measured between the anchor point in the second radiograph and the reference point 1427 (reference anatomical feature) of the second image of the object of interest contained in the second radiograph. Due to vertical movement of the radiation source in relation to the radiation receiver, the magnification of the second image of the object of interest and the position of the second image of the object of interest will be different in the second radiograph than in the first radiograph 1422. Accordingly, analogously to FIGS. 6A and 6B, the distances $e_1$ and $e_2$ will be different.

The height h of the object of interest 1430 may be determined based on triangles 1432 and 1434 illustrated in FIG. 14E. Specifically, based on triangles 1432 and 1434, the tangent of the angle $\theta_1$ may be expressed as Equations (82) and (83) respectively.

$$\tan(\theta_1) = \frac{b}{d_1 - h} \quad (82)$$

$$\tan(\theta_1) = \frac{e_1}{d_1} \quad (83)$$

Equations (82) and (83) may be combined into Equation (84) to solve for b, where b is the distance between the edge (reference point) of object of interest 1430 and a line projecting from the radiation source 1400 to anchor point 1426. The magnification $M_1$ of the image 1427 contained in radiograph 1422 may be expressed according to Equation (6).

$$\frac{b}{d_1 - h} = \frac{e_1}{d_1} \quad (84)$$

$$b = \frac{e_1(d_1 - h)}{d_1}$$

An equivalent procedure may be carried out for the second image acquired with the radiation source at the second position, as described with respect to FIGS. 6A-6D. Based on the second image contained in the second radiograph, the distance b may also be expressed according to Equation (85) and the magnification $M_2$ of the image 612 may be expressed by Equation (8).

$$b = \frac{e_2(d_2 - h)}{d_2} \quad (85)$$

In order to determine the magnification of either image 1427 or the second image contained in the second radiograph, example embodiments may determine the height h of the object 1430 by combining Equations (84) and (85), resulting in Equation (86).

$$\frac{e_1(d_1 - h)}{d_1} = \frac{e_2(d_2 - h)}{d_2} \quad (86)$$

$$e_1 d_2 (d_1 - h) = e_2 d_1 (d_2 - h)$$

$$h = \frac{d_1 d_2 (e_2 - e_1)}{d_1 e_2 - d_2 e_1}$$

The height h may now be used with Equations (6) and (8) to determine the magnifications $M_1$ and $M_2$. The determined magnifications may be used to scale the corresponding images in order to determine the actual physical size of the object of interest 1430. In general, any of the embodiments described herein may use a distance between an anchor point (stationary reference point) and a reference point in an image of an object of interest in place of a diameter, size, or other dimension of the object of interest when determining a height of the object of interest and/or a magnification of an image of the object of interest. The reference point and/or anchor point may be any identifiable point in the radiograph and is not limited to the examples provided herein. The elements of the embodiment described with respect to FIGS. 14C-14E may be combined with any of the other embodiments described, illustrated, or otherwise contemplated herein. Likewise, elements of all other embodiments described herein may be combined with the embodiment illustrated in FIGS. 14C-14E. The operations of the embodiment described with respect to FIGS. 14C-14E may be carried out by a computing device.

VIII. EXAMPLE USER INTERFACE IMPLEMENTATIONS

The embodiments described herein may be implemented on a computing device. The computing device may be a computer executing program instructions stored in a non-transitory computer readable medium or it may be a device where the functions are implemented directly in hardware circuitry. In one embodiment, the computing device may also execute instructions in order to provide a graphical user interface. Among other features, the graphical user interface may instruct a user to place a virtual marker at the position of the object of interest.

Figure 15:
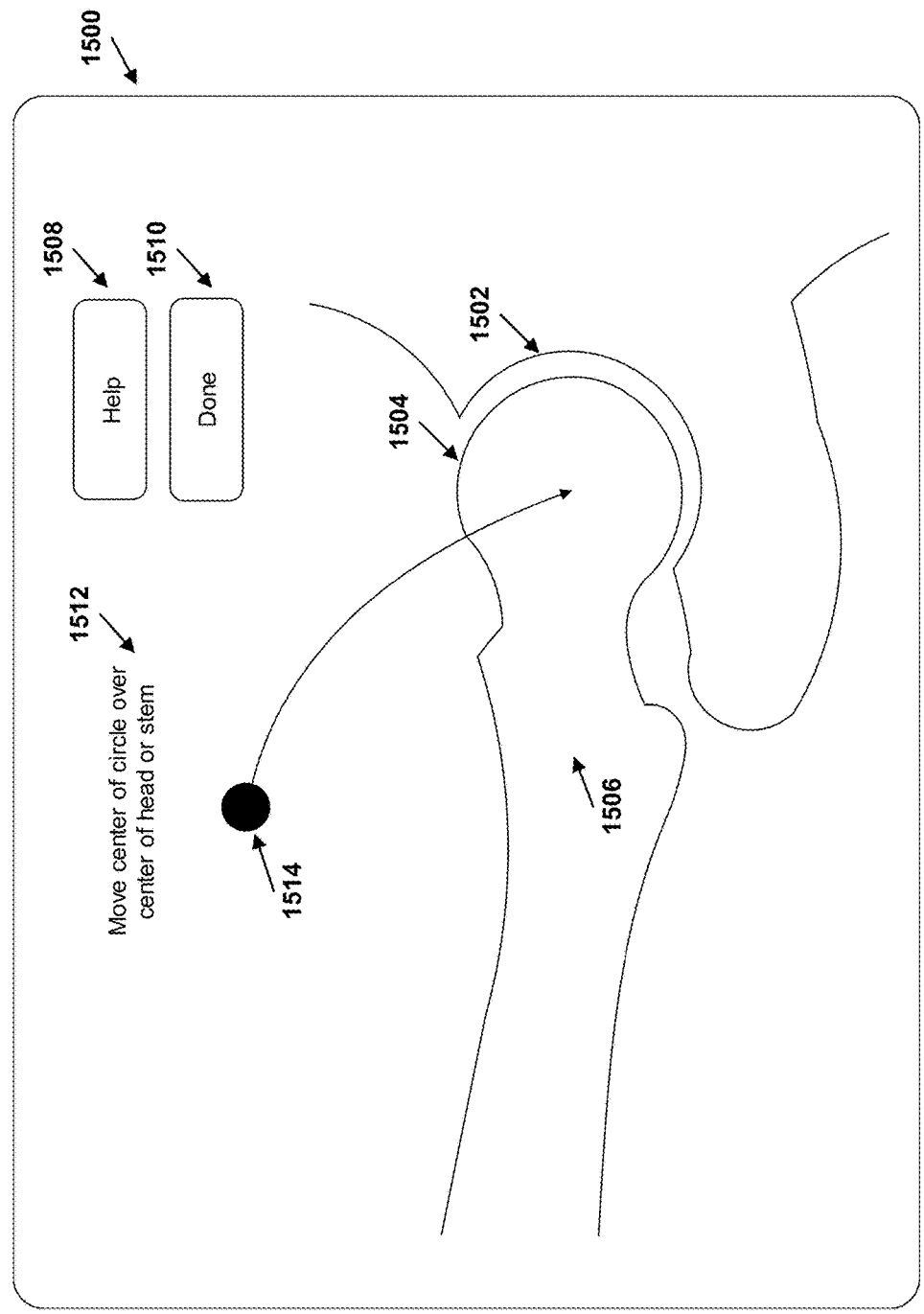
FIG. 15 illustrates an example user interface being used to identify objects of interest, according to an example embodiment.

FIG. 15 depicts example user interface 1500 displaying a lateral radiograph of a human hip comprising acetabulum image 1502, femoral head image 1504, and femoral calcar image 1506. The user interface 1500 provides instructions 1512 to move the circle 1514 over the center of the femoral head image 1504. The example user interface may additionally include buttons 1508 and 1450. For example, button 1510 may be used to inform the software that the circle 1514 has been placed over the femoral head 1504. The user interface may subsequently prompt the user to identify other objects of interest, such as the femoral calcar image 1506 or a calibration marker (not shown) if a calibration marker was used.

Alternatively, the program instructions may cause the computing device to automatically identify all objects of interest via known feature (e.g., geometric feature) recognition algorithms. The automatic identification of objects of interest may be indicated to a user via virtual markers overlaid on top of the displayed radiograph. For example, circular marker 1514 may be shown overlaid atop the femoral head image 1504 when the automatic identification of objects of interest has been completed. The graphical user interface may prompt a user to verify and/or correct any errors committed by the automatic identification process. The process of identifying the objects of interest may be repeated for all available radiographs.

The computing device may subsequently determine the height of the objects of interest and the magnification corresponding to each object of interest. If more than one object of interest is identified, the computing device may determine the spatial orientation of the objects of interest relative to each other. The computing device may scale the portions of the radiograph representing images of the objects of interest by the level of magnification corresponding to each object of interest. The scaled images may subsequently be used with digital templating in order to determine a template closest in size to the actual physical size of the object of interest. For example, the acetabulum image 1502 in radiograph 1500 may be scaled according to the level of magnification determined to correspond to the acetabulum image 1502. Since the femoral head is at the same height as the acetabulum (the femoral head is centered in the acetabulum and the two share the same center point), templates representing replacement acetabular prostheses may be overlaid on top of the scaled acetabulum image 1502 to find a replacement prosthesis closest in size and shape to the actual physical size of the acetabulum represented by acetabulum image 1502.

Alternative embodiments may scale the template objects instead of scaling the image of the object of interest. For example, a plurality of template objects may represent a plurality of available replacement hip prostheses. Instead of scaling the image of the object of interest in order to represent the actual physical size of the object of interest, the plurality of template objects may be scaled by the determined levels of magnification of the objects of interest. The portion of the template corresponding to the femoral calcar image 1506 may be magnified by the magnification corresponding to the femoral calcar and the portion of the template corresponding to the femoral head image 1504 may be magnified by the magnification corresponding to the femoral head. Alternatively, since the femoral head and the acetabulum form a concentric ball-and-socket joint having the same center point, the two are located at the same height. Accordingly, the magnification determined to correspond to the femoral head image 1504 may, in this particular example, also be used to scale the image of acetabulum 1502. Templates may be chosen from the plurality of templates that correspond to the degree of rotation of the hip depicted in the radiograph. The rotation of the hip may be determined as previously described with respect to FIGS. 9A-9D. Consequently, the template object closest in size and shape to the object of interest may be determined regardless of whether the image or template is scaled.

Figure 16A:
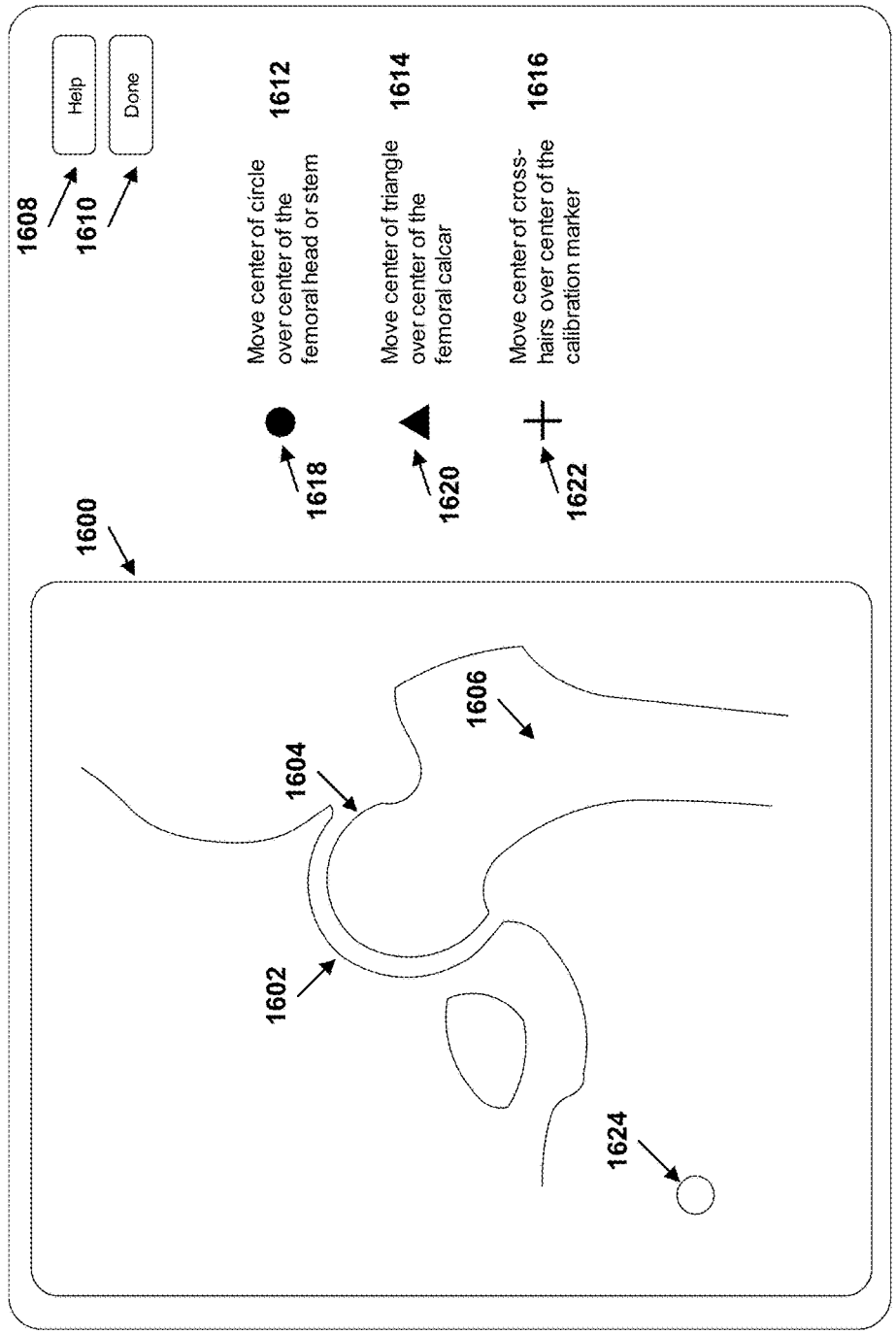
FIGS. 16A and 16B illustrate a user interface being used to identify multiple objects of interest, according to an example embodiment.
Figure 16B:
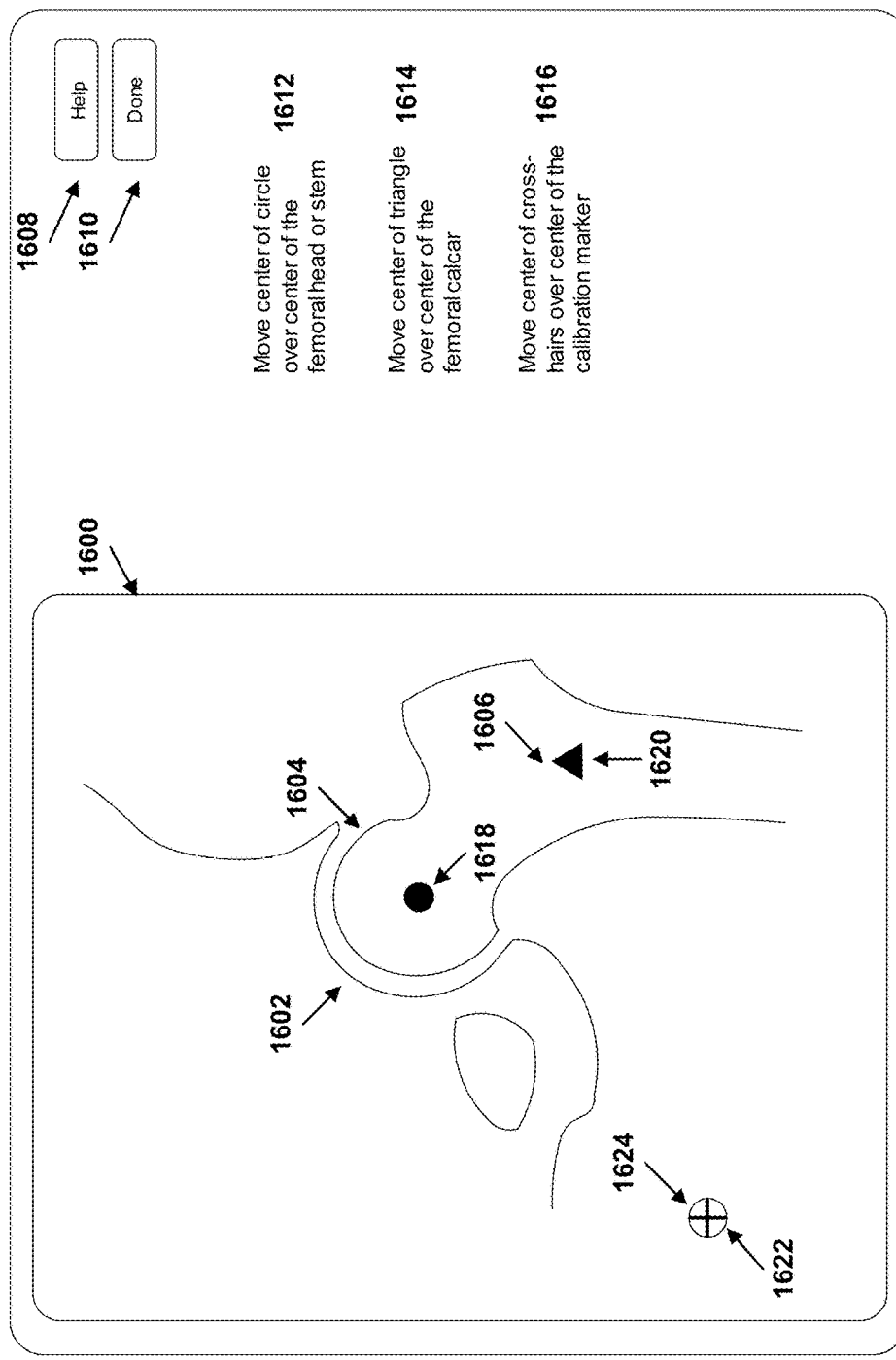

FIGS. 16A and 16B illustrate another embodiment of a user interface. The user interface may display a radiograph 1600 of a human hip. The radiograph 1600 may comprise acetabulum image 1602, femoral head image 1604, and femoral calcar image 1606. Included in the radiograph may be a calibration marker image 1624. The user interface may display prompts 1612-1616 requesting the placement of circle 1618 over the center of the femoral head image 1604, triangle 1620 over the center of the femoral calcar image 1606, and cross-hairs 1622 over the center of the calibration marker image 1624. The shapes 1618-1622 may be varied among implementations. The user interface may additionally include a plurality of buttons associated with different functions, such as, for example, button 1608 configured to cause the software to display additional helpful information and/or button 1610 configured to indicate to the software that the tasks indicated by prompts 1612-1616 have been completed.

FIG. 16B illustrates an example state of the user interface from FIG. 16A after the shapes 1618-1622 have been moved to their respective positions, as requested by prompts 1612-1616. Alternatively, the software instructions may cause the computing device to move the shapes 1618-1622 to their respective locations without user input. The software instructions may cause the computing device to detect features of interest such as acetabulum image 1602, femoral head image 1604, and femoral calcar image 1606 as well as calibration marker image 1624. The anatomical feature images 1602, 1604, and 1606 may be detected using known feature detection algorithms.

The computing device may subsequently proceed to determine the magnification of the images of objects of interest 1602, 1604 and 1606, scale the images of the objects of interest 1602, 1604, and 1606 according to the determined magnification, and/or determine the orientation of the femur relative to the pelvis (hip angle). The hip angle may be determined based on the height of the femoral head and the femoral calcar, as discussed with respect for FIGS. 9A-9D.

The determined hip angle may be displayed on the user interface. The determined magnifications corresponding to hip feature images 1602, 1604, and 1606 as well as the determined hip angle may be used to find, via templating techniques, a prosthesis closest in size and shape to the anatomical features of the hip illustrated in radiograph 1600.

The templating process may comprise selecting a 2D template from a plurality of templates. The plurality of templates may represent 2D images and/or cross-sections of replacement hip prostheses of different sizes and in different spatial orientations. The selected 2D template may correspond to the determined spatial orientation (hip angle) of the femur in radiograph 1600 and may represent a prosthesis closest in size to the physical size of the anatomical features represented by images 1602, 1604, and 1606 of the hip shown in radiograph 1600. Alternatively, a 3D template of the prosthesis may be rotated into the same orientation as the femur and may be used to template the hip or portions thereof. Some embodiments may use a 3D template to generate a plurality of 2D templates. The template, portions of the template, radiograph, portions of the radiograph representing the objects of interest, or a combination thereof may be scaled according to the level of magnification corresponding to the objects of interest in order to determine a template closest in size to the actual physical size of the object or objects of interest.

IX. EXAMPLE OPERATIONS

Figure 17:
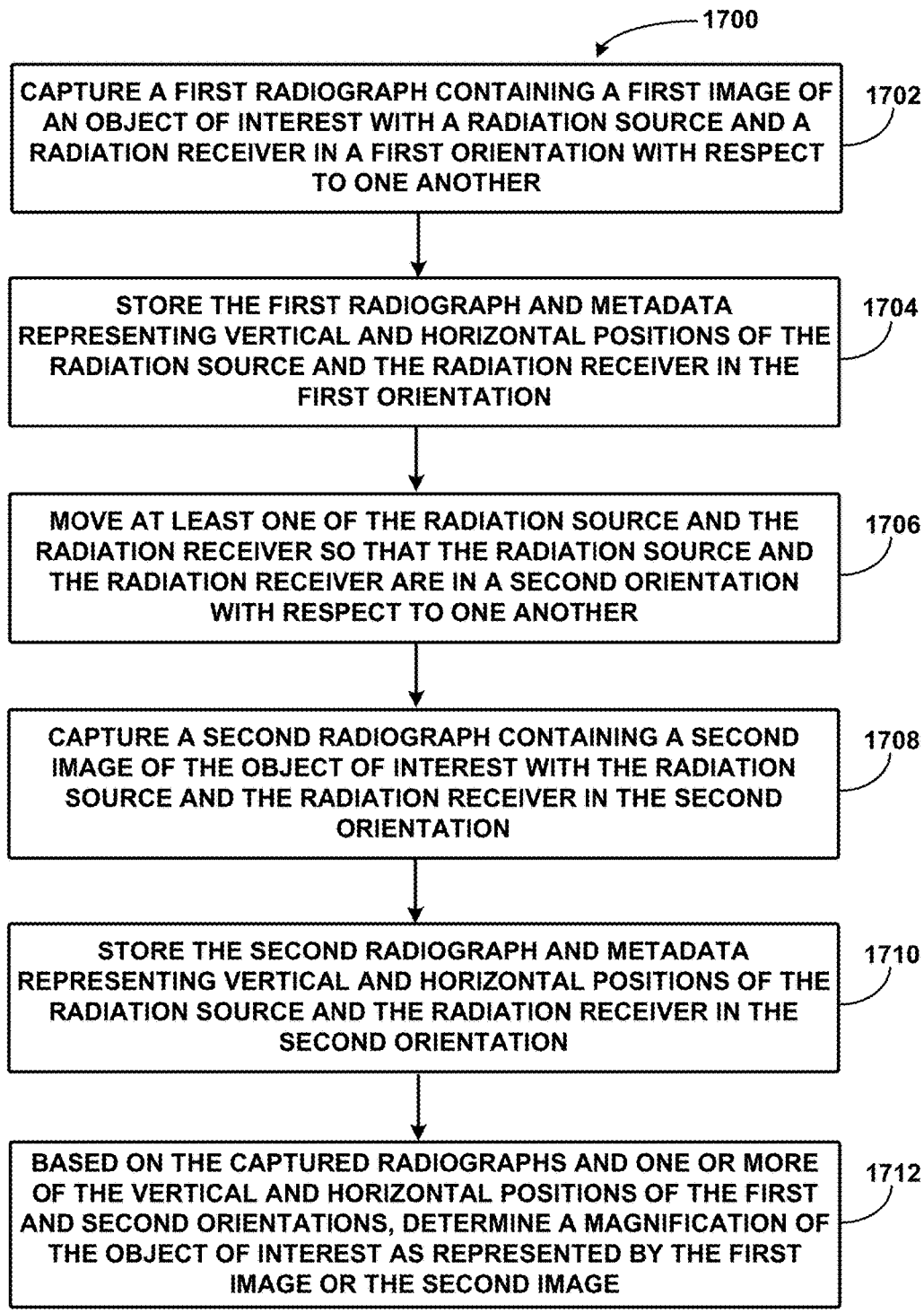
FIG. 17 illustrates a flow chart, according to an example embodiment.

FIG. 17 illustrates an example flow chart 1700. In block 1702, a first radiograph, containing a first image of an object of interest may be captured. The first radiograph may have been captured by a radiographic device with a radiation source and a radiation receiver in a first orientation with respect to one another.

The radiograph may be in the form of a film (e.g., X-ray film) when acquired using traditional radiography equipment. Alternatively, the radiograph may be a file or digital representation when acquired using a radiography system utilizing a digital radiation detector in place of film. The representation of the radiograph may be the radiograph itself, a physical image copy of the radiograph, a digital image file, and/or a temporary display of the radiograph on a screen. For example, the radiograph may be represented and/or stored as a Joint Photographic Experts Group file format (JPEG), Tagged Image File Format (TIFF), Graphics Interchange Format (GIF), Bitmap file format (BMP), Portable Network Graphics file format (PNG), or any number of other file types or file formats. The object of interest may be a joint, a bone, a bone feature, or any other object. For example, the object of interest may be the head of a femur. The image of the object of interest may be an image created on the radiation receiver when the object of interest is exposed to radiation from the radiation source.

In block 1704, the first radiograph may be stored along with metadata representing vertical and horizontal positions of the radiation source and the radiation receiver in the first orientation. The metadata may be associated with the representation of the radiograph. For example, the metadata may be stored as part of the file containing a representation of the radiograph. Alternatively, the metadata may be a separate file that is linked to or associated with the file storing the representation of the radiograph.

In block 1706, at least one of the radiation source and the radiation receiver may be moved so that the radiation source and the radiation receiver are in a second orientation with respect to one another. For example, the radiation source may be translated horizontally, translated vertically, and/or rotated with respect to the radiation receiver. Alternatively, the radiation receiver may be moved with respect to the radiation source. It may also be possible to move both the radiation source and the radiation receiver relative to one another in order to place them in the second orientation.

In block 1708, a second radiograph, containing a second image of the object of interest may be captured or obtained. The second radiograph may be captured by a radiographic device with the radiation source and the radiation receiver in the second orientation.

The first orientation may comprise, for example, position 614 of radiation source 600 in relation to radiation receiver 604, as depicted in FIG. 6A. Similarly, the second orientation may comprise position 616 of radiation source 600 in relation to radiation receiver 604, as depicted in FIG. 6B. An alternative example of the first orientation may be position 716 of radiation source 700 in relation to radiation receiver 704, as depicted in FIG. 7B. Similarly, the second orientation may alternatively comprise position 714 of radiation source 700 in relation to radiation receiver 704, as depicted in FIG. 7A. The first and second orientations may also be achieved according to any of the other example embodiments described herein. Additional orientations are possible.

In block 1710, the second radiograph may be stored along with metadata representing vertical and horizontal positions of the radiation source and the radiation receiver in the second orientation.

In block 1712, a magnification of the object of interest as represented by the first image or the second image may be determined. The determined magnification may be based on the captured radiographs and one or more of the vertical and horizontal positions of the first and second orientations. The magnification may be determined according to any of the example embodiments described herein. The operations of flow chart 1700 may be carried out by a computing device, a radiographic system, or a combination thereof.

Determining a magnification of the object of interest according to block 1712 may include determining a first width, dimension, and/or size of the first image and determining a second width, dimension, and/or size of the second image. Determining the magnification may also involve determining a vertical distance of the object of interest above the radiation receiver based on the first width, the second width, and one or more of the vertical and horizontal positions of the first and second orientations.

The object of interest may be, in general, any object, article, item, or feature of interest. For example, the object of interest may be a bone or bone feature of a human body. The magnification determined in block 1712 may be used to determine an unmagnified size of the object of interest. For example, the image of the object of interest contained in a radiograph or representation of a radiograph may be scaled and the scaled version may be saved, stored, and/or displayed. The unmagnified size of the object of interest may be approximately equal to an actual physical size of the object of interest. Based on the unmagnified size, a surgical template closest in size to the unmagnified size of the object of interest may be selected from a plurality of surgical templates of different sizes. For example, the surgical template may represent a hip prosthesis that most closely matches the size and shape of a patient's anatomical features of the hip. The plurality of surgical templates may represent a range of the prostheses available off the shelf from different prosthesis manufacturers. The prosthesis represented by the selected surgical template may subsequently be surgically implanted to replace anatomical features of the patient.

In some embodiments, at least one of the first radiograph of block 1702 and the second radiograph of block 1708 may additionally contain an image of at least one calibration marker having at least on known dimension (e.g., width, diameter, height above or below the radiation source or radiation receiver, position relative to the radiation source or radiation receiver). At least one of the vertical and horizontal positions of the first orientation and vertical and horizontal positions of the second orientation may be determined based on the image of the at least one calibration marker and the at least one known property of the at least one calibration marker. This determination may be done in accordance with any of the embodiments described with respect to FIGS. 11-14B.

Figure 18:
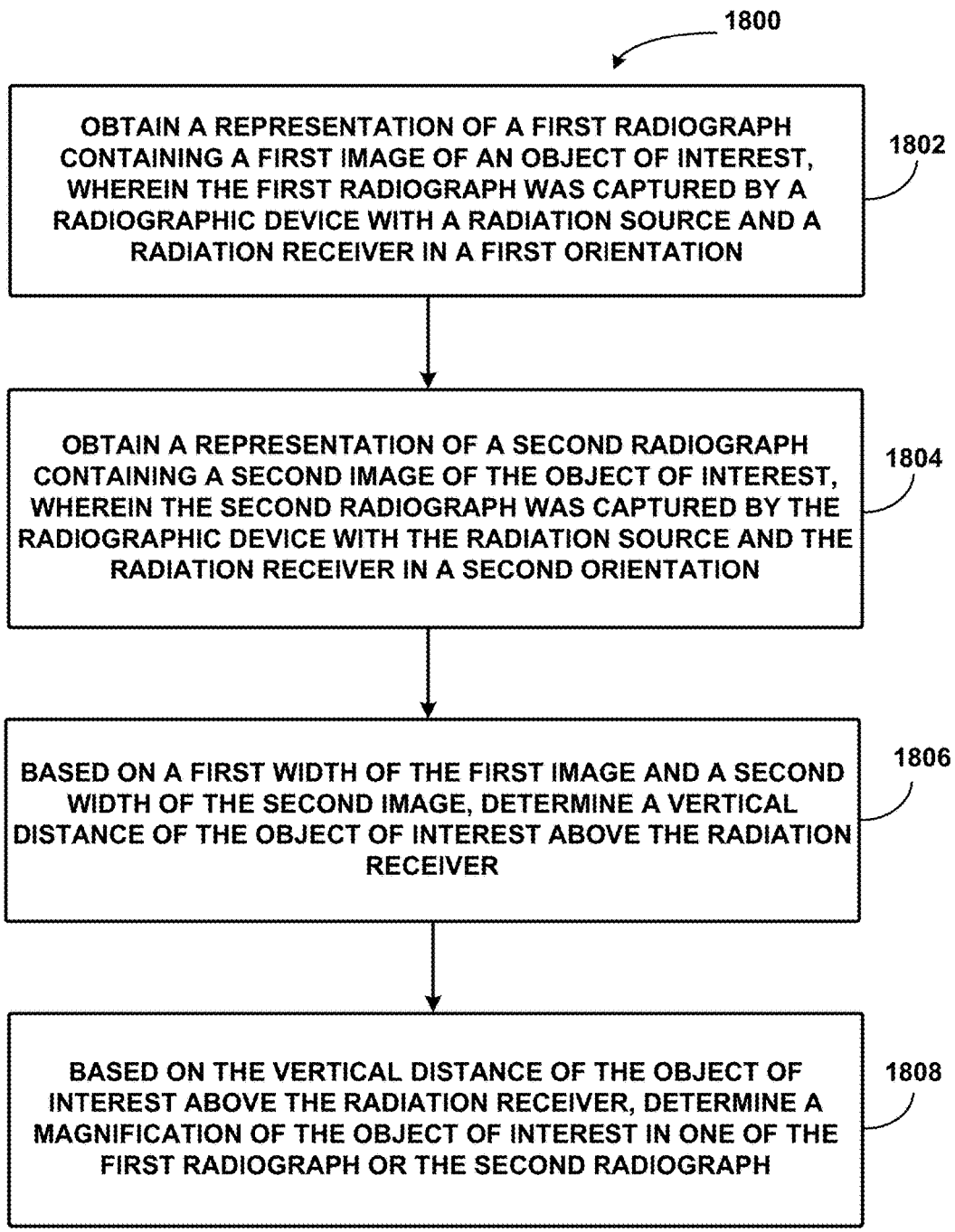
FIG. 18 illustrates another flow chart, according to an example embodiment.

FIG. 18 illustrates another example flow chart 1800. In block 1802, a representation of a first radiograph, containing a first image of an object of interest may be obtained. The first radiograph may have been captured by a radiographic device with a radiation source and a radiation receiver in a first orientation. The radiograph may be stored and/or represented in any of the formats previously discussed. The radiograph or representation of the radiograph may be associated with metadata indicating the positions of the radiation receiver and the radiation source.

In block 1804, a representation of a second radiograph, containing a second image of the object of interest may be obtained. The second radiograph may have been captured by a radiographic device with the radiation source and the radiation receiver in a second orientation. The first and second orientations may be achieved according to any of the example embodiments described herein. Additional orientations are possible.

In block 1806, a vertical distance of the object of interest above the radiation receiver may be determined. The vertical distance may be determined based on a first width of the first image of the object of interest and a second width of the second image of the object of interest. The width may be any dimension of the image that is representative of the size of the object or a portion thereof. For example, in the case of a circular object, the width may be a diameter of the circular image produced by the circular object. The vertical distance of the object of interest above the radiation receiver may be determined according to any of the examples described herein.

In the first orientation, the radiation source and radiation receiver may be at a first vertical distance and a particular lateral distance from one another. In the second orientation, the radiation source and the radiation receiver may be at a second vertical distance and at the particular lateral distance from one another. The vertical distance of the object of interest above the radiation receiver may also be based on the first vertical distance and the second vertical distance. Determination of the vertical distance of the object of interest above the radiation receiver may be done in accordance with the example embodiment of FIGS. 6A-6D.

The first vertical distance may be stored in first metadata associated with the representation of the first radiograph. Likewise, the second vertical distance may be stored in second metadata associated with the representation of the second radiograph. The determination of the vertical distance of the object of interest above the radiation source may further include obtaining the first vertical distance from the first metadata, obtaining the second vertical distance from the second metadata, obtaining the first width of the first image of the object of interest from the representation of the first radiograph, and obtaining the second width of the second image of the object of interest from the representation of the second radiograph.

In an alternative embodiment, the radiation source and radiation receiver may be at a first vertical distance and a first lateral distance from one another in the first orientation. In the second orientation, the radiation source and the radiation receiver may be at a second vertical distance and at a second lateral distance from one another. The vertical distance of the object of interest above the radiation receiver may also be based on the first vertical distance, the first lateral distance, the second vertical distance, and the second lateral distance. Determination of the vertical distance of the object of interest above the radiation receiver may be done in accordance with the example embodiment of FIGS. 7A-7E.

In some embodiments, at least one of the first radiograph of block 1802 and the second radiograph of block 1804 may additionally contain an image of at least one calibration marker having at least on known dimension (e.g., width, diameter, height above or below the radiation source or radiation receiver, position relative to the radiation source or radiation receiver). At least one of the first vertical distance in the first orientation, the first lateral distance in the first orientation, the second vertical distance in the second orientation, and the second lateral distance in the second orientation may be determined based on the image of the at least one calibration marker and the at least one known dimension of the at least one calibration marker. This determination may be done in accordance with any of the embodiments described with respect to FIGS. 11-14B. Alternatively or additionally, the vertical distance of the object of interest may be determined based on the image of the at least one calibration marker and the at least one known dimension of the calibration marker.

In additional embodiments, the vertical distance of the object of interest above the radiation receiver may also be based on the angles of a triangle. The triangle may be formed by a first point within the object of interest, a second point in the first image of the object of interest that is based on a first projection of the radiation source through the first point when the radiation source and the radiation receiver are in the first orientation, and a third point in the second image of the object of interest that is based on a second projection of the radiation source through the first point when the radiation source and the radiation receiver are in the second orientation. Triangle 732 illustrated in FIG. 7D may be an example of such triangle.

In further embodiments, the radiation source may be above and approximately centered with respect to the radiation receiver in the first orientation. The radiation source may be off-center with respect to the radiation receiver by several centimeters (e.g., 5 centimeters), provided that this offset away from the center is accounted for in any calculations of magnification or object height above the radiation receiver. In the second orientation, the radiation source and the radiation receiver may be at the same horizontal level. The second orientation may be achieved by rotation the radiation source and the radiation receiver by about 90 degrees from the first orientation. For example, the radiation source and the radiation receiver may be rotated by anywhere from 80 degrees to 100 degrees. This range may be larger or smaller provided that any calculations of magnification account for (include in the geometric model and associated calculations) the effect of the particular degree of rotation. This process may be done in accordance with the embodiments described with respect to FIGS. 8A, 8B, 13A, and 13B.

In block 1808, a magnification of the object of interest in one of the first radiograph or the second radiograph may be determined. The determined magnification may be based on the vertical distance of the object of interest above the radiation receiver. The magnification may be determined according to any of the example embodiments described herein. The operations of flow chart 1800 may be carried out by a computing device, a radiographic system, or a combination thereof.

The determined magnification may be used to perform templating operations. For example, the object of interest may be a bone feature. Based on the determined magnification, an unmagnified size of the bone feature may be determined. A surgical template may be selected from a plurality of surgical templates of different sizes. The selected template may be closest in size to the unmagnified size of the bone feature.

The object of interest may be a first of many objects of interest represented by the radiograph. The first radiograph may additionally contain a third image of a second object of interest. Likewise, the second radiograph may additionally contain a fourth image of the second object of interest. Based on the representation of the first radiograph, a horizontal distance between the first object of interest and the second object of interest may be determined in a plane of the first radiograph. A vertical distance of the second object of interest above the radiation receiver may be determined based on a third width of the third image and a fourth width of the fourth image. A height difference between the first object of interest and the second object of interest may be determined based on the vertical distance of the first object of interest above the radiation receiver and the vertical distance of the second object of interest above the second radiation receiver. A three-dimensional relationship between the first object of interest and the second object of interest may be determined based on the horizontal distance and the height difference between the first object of interest and the second object of interest.

In some embodiments, the first object of interest may be a first bone feature of a bone and the second object of interest may be a second bone feature of the bone. For example, the bone may be a femur. The first bone feature may be the head of the femur and the second bone feature may be the femoral calcar. Determining the three-dimensional relationship between the first bone feature and the second bone feature may involve determining a degree of rotation of the bone. For example, the degree of rotation of the bone may be a degree of anteversion of the femur measured with respect to the pelvis. The determination of the degree of rotation of the bon may be done in accordance with the embodiment described with respect to FIGS. 9A-9D.

Based on the degree of rotation of the bone, a surgical template may be selected from a plurality of surgical templates. The plurality of surgical templates may have a plurality of different sizes and may represent a plurality of three-dimensional orientations of replacement prostheses. For example, the plurality of surgical templates may represent multiple two-dimensional cross-sections of a three-dimensional prosthesis. Each cross-section may correspond to a different orientation of the three-dimensional prosthesis. Selecting a surgical template may involve selecting a cross-section of the prosthesis that represents the prosthesis in approximately the same three-dimensional orientation as the three-dimensional orientation of the bone at the time of capturing of the radiograph. The selected surgical template may be closest in size to a physical size of at least one of the first and second objects of interest. The selected surgical template may also be closest in shape to the anatomical features of the bone and/or bone features.

In further embodiments, a particular image of the first image and the second image may be an elongated representation of the object of interest. Determining the magnification of the object of interest may include determining a first magnification for at least a first portion of the particular image and determining a second magnification for at least a second portion of the particular image. Based on the determined first and second magnifications, an unmagnified size of the object of interest may be determined. A surgical template may be selected from a plurality of surgical templates of different sizes. The selected surgical template may be closest in size to the unmagnified size of the object of interest. The first and second magnifications may be determined in accordance with the embodiments described with respect to FIGS. 7A-7E.

Figure 19:
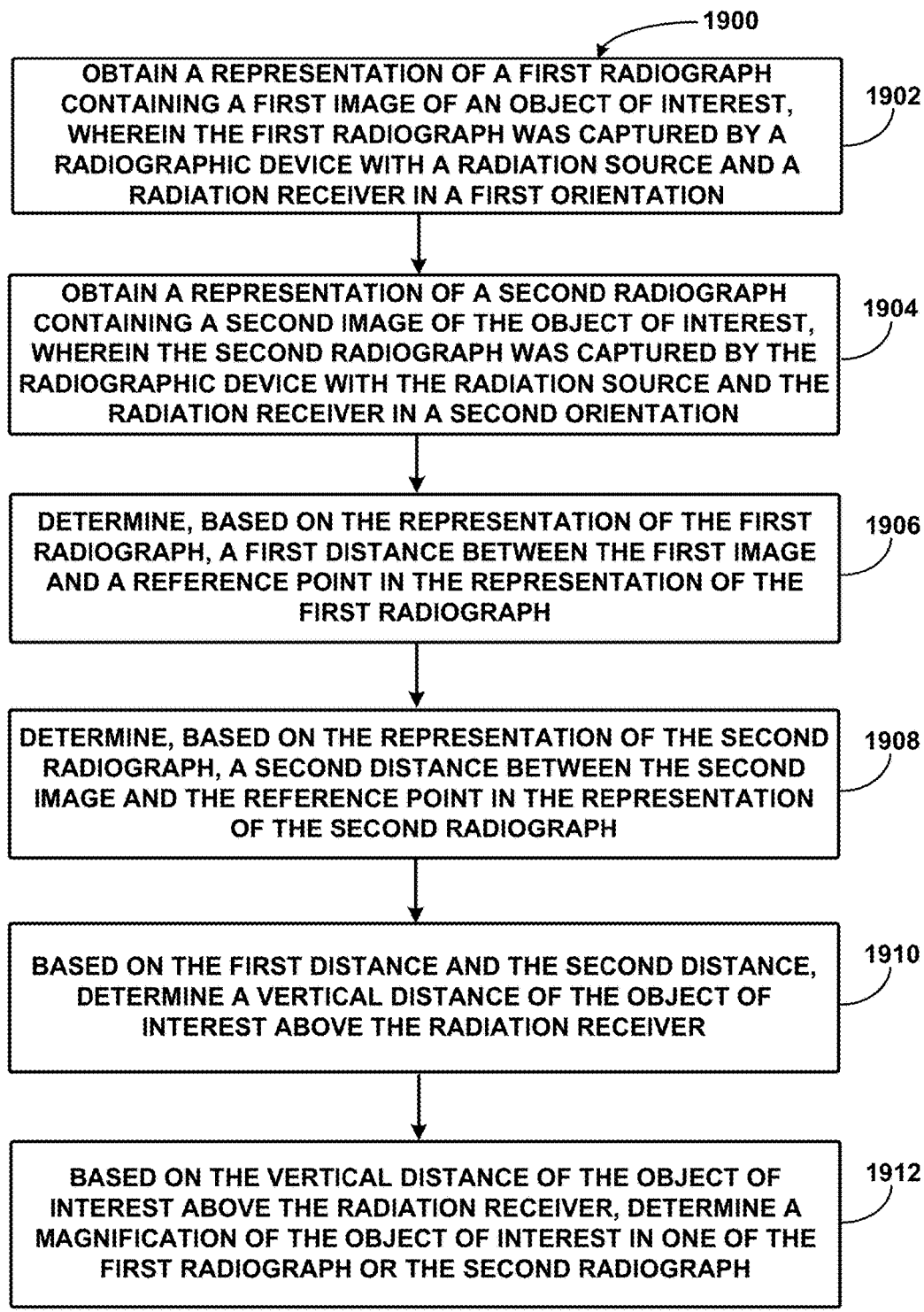
FIG. 19 illustrates yet another flow chart, according to an example embodiment.

FIG. 19 illustrates another example flow chart 1900. Specifically, in block 1902 a representation of a first radiograph containing a first image of an object of interest may be obtained. The first radiograph may have been captured by a radiographic device with a radiation source and a radiation receiver in a first orientation. In block 1904, a representation of a second radiograph containing a second image of an object of interest may be obtained. The second radiograph may have been captured by a radiographic device with a radiation source and a radiation receiver in a second orientation.

In block 1906, a first distance between the first image and a reference point in the representation of the first radiograph may be determined based on the representation of the first radiograph. In block 1908, a second distance between the second image and the reference point in the representation of the second radiograph may be determined based on the representation of the second radiograph. The operations of block 1906 and 1908 may be carried out according the example embodiment described with respect to FIGS. 14C-14E.

In block 1910, a vertical distance of the object of interest above the radiation receiver may be determined. The determination of the vertical distance may be based on the first distance and the second distance. In block 1912, a magnification of the object of interest may be determined in one of the first radiograph or the second radiograph based on the vertical distance of the object of interest. The determined magnification may be used to scale the corresponding image in order to accurately represent the actual physical size of the object of interest. Alternatively or additionally, the determined magnification may be used in order to select a template object closest in size and/or shape to the size and shape of the object of interest.

Flow charts 1700, 1800, and 1900 may be combined with any features, aspects, and/or implementations disclosed herein or in the accompanying drawings.

X. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A radiographic system comprising:
    a radiation source;
    a radiation receiver, wherein at least one of the radiation source and the radiation receiver is movable with respect to one another;
    a processor;
    a memory; and
    program instructions stored in the memory that, when executed by the processor, cause the radiographic system to perform operations comprising:
        capturing a first radiograph containing a first image of a first object of interest with the radiation source and the radiation receiver in a first orientation with respect to one another;
        storing, in the memory, the first radiograph and metadata representing vertical and horizontal positions of the radiation source and the radiation receiver in the first orientation;
        moving at least one of the radiation source and the radiation receiver so that the radiation source and the radiation receiver are in a second orientation with respect to one another;
        capturing a second radiograph containing a second image of the first object of interest with the radiation source and the radiation receiver in the second orientation;
        storing, in the memory, the second radiograph and metadata representing vertical and horizontal positions of the radiation source and the radiation receiver in the second orientation;
        based on the captured radiographs and one or more of the vertical and horizontal positions of the first and second orientations, determining a magnification of the first object of interest as represented by the first image or the second image, wherein the first radiograph additionally contains a third image of a second object of interest, and wherein the second radiograph additionally contains a fourth image of the second object of interest;
        determining, based on the first radiograph, a horizontal distance between the first object of interest and the second object of interest in a plane of the first radiograph;
        based on a third width of the third image and a fourth width of the fourth image, determining a vertical distance of the second object of interest above the radiation receiver;
        determining, based on a vertical distance of the first object of interest above the radiation receiver and the vertical distance of the second object of interest above the radiation receiver, a height difference between the first object of interest and the second object of interest; and
        determining, based on the horizontal distance and the height difference between the first object of interest and the second object of interest, a three-dimensional relationship between the first object of interest and the second object of interest.

2. The radiographic system of claim 1, wherein determining the magnification of the first object of interest comprises:
    determining a first width of the first image;
    determining a second width of the second image; and
    determining the vertical distance of the first object of interest above the radiation receiver based on the first width, the second width, and one or more of the vertical and horizontal positions of the first and second orientations.

3. The radiographic system of claim 1, wherein the first object of interest is a bone feature, and wherein the program instructions further cause the radiographic system to perform operations comprising:
    based on the magnification of the first object of interest, determining an unmagnified size of the first object of interest; and
    selecting, from a plurality of surgical templates of different sizes, a surgical template closest in size to the unmagnified size of the first object of interest.

4. The radiographic system of claim 1, wherein at least one of the first radiograph and the second radiograph additionally contains an image of at least one calibration marker having at least one known dimension, and wherein the program instructions further cause the radiographic system to perform operations comprising:
    determining, based on the image of the at least one calibration marker and the at least one known dimension of the at least one calibration marker, the vertical and horizontal positions of the radiation source and the radiation receiver in the first orientation and the vertical and horizontal positions of the radiation source and the radiation receiver in the second orientation.

5. A method comprising:
    obtaining, by a computing device, a representation of a first radiograph containing a first image of a first object of interest, wherein the first radiograph was captured by a radiographic device with a radiation source and a radiation receiver in a first orientation;
    obtaining, by the computing device, a representation of a second radiograph containing a second image of the first object of interest, wherein the second radiograph was captured by the radiographic device with the radiation source and the radiation receiver in a second orientation;
    based on a first width of the first image and a second width of the second image, determining, by the computing device, a vertical distance of the first object of interest above the radiation receiver;
    based on the vertical distance of the first object of interest above the radiation receiver, determining, by the computing device, a magnification of the first object of interest in one of the first radiograph or the second radiograph, wherein the first radiograph additionally contains a third image of a second object of interest, and wherein the second radiograph additionally contains a fourth image of the second object of interest;
    determining, based on the representation of the first radiograph, a horizontal distance between the first object of interest and the second object of interest in a plane of the first radiograph;

based on a third width of the third image and a fourth width of the fourth image, determining a vertical distance of the second object of interest above the radiation receiver;

determining, based on the vertical distance of the first object of interest above the radiation receiver and the vertical distance of the second object of interest above the radiation receiver, a height difference between the first object of interest and the second object of interest; and determining, based on the horizontal distance and the height difference between the first object of interest and the second object of interest, a three-dimensional relationship between the first object of interest and the second object of interest.

6. The method of claim 5, wherein the radiation source and the radiation receiver are at a first vertical distance and a particular lateral distance from one another in the first orientation, wherein the radiation source and the radiation receiver are at a second vertical distance and the particular lateral distance from one another in the second orientation, and wherein the vertical distance of the first object of interest above the radiation receiver is also based on the first vertical distance and the second vertical distance.

7. The method of claim 6, wherein the first vertical distance is stored in first metadata associated with the representation of the first radiograph, wherein the second vertical distance is stored in second metadata associated with the representation of the second radiograph, and wherein determining the vertical distance of the first object of interest above the radiation receiver comprises:

obtaining the first vertical distance from the first metadata;

obtaining the second vertical distance from the second metadata;

obtaining the first width from the representation of the first radiograph; and obtaining the second width from the representation of the second radiograph.

8. The method of claim 5, wherein the first object of interest is a bone feature, the method further comprising:

based on the magnification of the first object of interest, determining an unmagnified size of the first object of interest; and selecting, from a plurality of surgical templates of different sizes, a surgical template closest in size to the unmagnified size of the first object of interest.

9. The method of claim 5, wherein the radiation source and the radiation receiver are at a first vertical distance and a first lateral distance from one another in the first orientation, wherein the radiation source and the radiation receiver are at a second vertical distance and a second lateral distance from one another in the second orientation.

10. The method of claim 9, and wherein the vertical distance of the first object of interest above the radiation receiver is also based on the first vertical distance, the second vertical distance, the first lateral distance, and the second lateral distance.

11. The method of claim 9, wherein the vertical distance of the first object of interest above the radiation receiver is also based on the angles of a triangle formed by (i) a first point within the first object of interest, (ii) a second point in the first image of the first object of interest that is based on a first projection of the radiation source through the first point, the radiation source and the radiation receiver in the first orientation, and (iii) a third point in the second image of the first object of interest that is based on a second projection of the radiation source through the first point, the radiation source and the radiation receiver in the second orientation.

12. The method of claim 5, wherein the first object of interest is a first bone feature of a bone, wherein the second object of interest is a second bone feature of the bone, and wherein determining the three-dimensional relationship comprises determining a degree of rotation of the bone.

13. The method of claim 12, further comprising:

based on the degree of rotation of the bone, selecting, from a plurality of surgical templates having different sizes and representing a plurality of three-dimensional orientations, at least one surgical template closest in size to a physical size of at least one of the first and second objects of interest.

14. The method of claim 5, wherein the radiation source is above and approximately centered with respect to the radiation receiver in the first orientation, wherein the radiation source and the radiation receiver are at the same horizontal level in the second orientation, and wherein the second orientation is achieved by rotating the radiation source and the radiation receiver by about 90 degrees from the first orientation.

15. The method of claim 5, wherein at least one of the first radiograph and the second radiograph additionally contains an image of at least one calibration marker having at least one known dimension, wherein the radiation source and the radiation receiver are at a first vertical distance and a first lateral distance from one another in the first orientation, wherein the radiation source and the radiation receiver are at a second vertical distance and a second lateral distance from one another in the second orientation, and the method further comprising:

determining, based on the image of the at least one calibration marker and the at least one known dimension of the at least one calibration marker, at least one of the first vertical distance in the first orientation, the first lateral distance in the first orientation, the second vertical distance in the second orientation, and the second lateral distance in the second orientation.

16. The method of claim 15, wherein the at least one known dimension is a width of the at least one calibration marker, a vertical distance of the at least one calibration marker above the radiation receiver, a vertical distance of the at least one calibration marker below the radiation source, a lateral distance between the at least one calibration marker and an edge of the radiation receiver, or a lateral distance between the at least one calibration marker and a center of the radiation source.

17. The method of claim 5, wherein at least one of the first radiograph and the second radiograph additionally contains an image of at least one calibration marker having at least one known dimension, and wherein the vertical distance of the first object of interest above the radiation receiver is further based on the image of the at least one calibration marker and the at least one known dimension of the at least one calibration marker.

18. The method of claim 5, wherein a particular image of the first image and the second image is an elongated representation of the first object of interest, and wherein determining the magnification of the first object of interest comprises (i) determining a first magnification for at least a first portion of the particular image and (ii) determining a second magnification for at least a second portion of the particular image, wherein the method further comprises:

based on the first and second magnifications, determining an unmagnified size of the first object of interest; and selecting, from a plurality of surgical templates of different sizes, a surgical template closest in size to the unmagnified size of the first object of interest.

19. A non-transitory computer readable medium having stored thereon instructions that, when executed by a processor, cause the processor to perform operations comprising:

obtaining a representation of a first radiograph containing a first image of a first object of interest, wherein the first radiograph was captured by a radiographic device with a radiation source and a radiation receiver in a first orientation;

obtaining a representation of a second radiograph containing a second image of the first object of interest, wherein the second radiograph was captured by the radiographic device with the radiation source and the radiation receiver in a second orientation;

determining, based on the representation of the first radiograph, a first distance between the first image and a reference point in the representation of the first radiograph;

determining, based on the representation of the second radiograph, a second distance between the second image and the reference point in the representation of the second radiograph;

based on the first distance and the second distance, determining a vertical distance of the first object of interest above the radiation receiver;

based on the vertical distance of the first object of interest above the radiation receiver, determining a magnification of the first object of interest in one of the first radiograph or the second radiograph, wherein the first radiograph additionally contains a third image of a second object of interest, and wherein the second radiograph additionally contains a fourth image of the second object of interest;

determining, based on the first radiograph, a horizontal distance between the first object of interest and the second object of interest in a plane of the first radiograph;

based on (i) a third distance between the third image and the reference point in the representation of the first radiograph and (ii) a fourth distance between the fourth image and the reference point in the representation of the second radiograph, determining a vertical distance of the second object of interest above the radiation receiver;

determining, based on a vertical distance of the first object of interest above the radiation receiver and the vertical distance of the second object of interest above the radiation receiver, a height difference between the first object of interest and the second object of interest; and determining, based on the horizontal distance and the height difference between the first object of interest and the second object of interest, a three-dimensional relationship between the first object of interest and the second object of interest.

* * * * *